(12) United States Patent
DeYoung et al.

(10) Patent No.: US 11,850,333 B2
(45) Date of Patent: *Dec. 26, 2023

(54) COATINGS CONTAINING MULTIPLE DRUGS

(71) Applicant: MT Acquisition Holdings LLC, Pine Plains, NY (US)

(72) Inventors: James P. DeYoung, Dallas, TX (US); Charles Douglas Taylor, Franklinton, NC (US); James B. McClain, Ocracoke, NC (US); Clint Smoke, Raleigh, NC (US); Mike Cole, Raleigh, NC (US)

(73) Assignee: Micell Medtech Inc., Pine Plains, NY (US)

( * ) Notice: Subject to any disclaimer, the term of this patent is extended or adjusted under 35 U.S.C. 154(b) by 118 days.

This patent is subject to a terminal disclaimer.

(21) Appl. No.: 17/243,769

(22) Filed: Apr. 29, 2021

(65) Prior Publication Data

US 2021/0244861 A1 Aug. 12, 2021

Related U.S. Application Data

(63) Continuation of application No. 16/223,552, filed on Dec. 18, 2018, now Pat. No. 11,007,307, which is a continuation of application No. 15/591,287, filed on May 10, 2017, now abandoned, which is a continuation of application No. 14/969,884, filed on Dec. 15, 2015, now Pat. No. 9,737,645, and a continuation of application No. 14/473,741, filed on Aug. 29, 2014, now Pat. No. 9,415,142, said application No. 14/969,884 is a continuation of application No. 14/473,741, filed on Aug. 29, 2014, now Pat. No. 9,415,142, which is a continuation of application No. 12/298,459, filed as application No. PCT/US2007/010227 on Apr. 26, 2007, now Pat. No. 8,852,625.

(60) Provisional application No. 60/912,394, filed on Apr. 17, 2007, provisional application No. 60/745,731, filed on Apr. 26, 2006, provisional application No. 60/745,733, filed on Apr. 26, 2006.

(51) Int. Cl.
  *A61L 31/16* (2006.01)
  *A61L 31/10* (2006.01)
  *A61L 31/14* (2006.01)
  *A61F 2/90* (2013.01)
  *A61L 31/06* (2006.01)

(52) U.S. Cl.
  CPC ............ *A61L 31/16* (2013.01); *A61F 2/90* (2013.01); *A61L 31/06* (2013.01); *A61L 31/10* (2013.01); *A61L 31/148* (2013.01); *A61F 2210/0004* (2013.01); *A61F 2250/0067* (2013.01); *A61L 2300/20* (2013.01); *A61L 2300/216* (2013.01); *A61L 2300/236* (2013.01); *A61L 2300/416* (2013.01); *A61L 2300/42* (2013.01); *A61L 2300/426* (2013.01); *A61L 2300/602* (2013.01); *A61L 2300/608* (2013.01); *A61L 2300/61* (2013.01); *A61L 2420/02* (2013.01); *A61L 2420/06* (2013.01); *A61L 2420/08* (2013.01)

(58) Field of Classification Search
  CPC .......... A61L 31/16; A61L 31/06; A61L 31/10; A61L 31/148; A61L 2300/20; A61L 2300/216; A61L 2300/236; A61L 2300/416; A61L 2300/42; A61L 2300/426; A61L 2300/602; A61L 2300/608; A61L 2300/61; A61L 2420/02; A61L 2420/06; A61L 2420/08; A61F 2/90; A61F 2210/0004; A61F 2250/0067
  See application file for complete search history.

(56) References Cited

U.S. PATENT DOCUMENTS

| | | | |
|---|---|---|---|
| 3,087,860 A | 4/1963 | Endicott et al. |
| 3,123,077 A | 3/1964 | Alcamo |
| 3,457,280 A | 7/1969 | Schmitt et al. |
| 3,597,449 A | 8/1971 | Deprospero et al. |
| 3,737,337 A | 6/1973 | Schnoring et al. |
| 3,773,919 A | 11/1973 | Boswell et al. |
| 3,929,992 A | 12/1975 | Sehgal et al. |
| 4,000,137 A | 12/1976 | Dvonch et al. |
| 4,188,373 A | 2/1980 | Krezanoski |
| 4,285,987 A | 8/1981 | Ayer et al. |
| 4,326,532 A | 4/1982 | Hammar |
| 4,336,381 A | 6/1982 | Nagata et al. |

(Continued)

FOREIGN PATENT DOCUMENTS

| | | |
|---|---|---|
| CA | 2237466 A1 | 11/1998 |
| CA | 2589761 A1 | 6/2006 |

(Continued)

OTHER PUBLICATIONS

PCT/EP2000/004658 International Search Report from dated Sep. 15, 2000.

(Continued)

*Primary Examiner* — David J Blanchard
*Assistant Examiner* — Thurman Wheeler
(74) *Attorney, Agent, or Firm* — Lerner David LLP

(57) ABSTRACT

A method for depositing a coating comprising a polymer and at least two pharmaceutical agents on a substrate, comprising the following steps: providing a stent framework; depositing on said stent framework a first layer comprising a first pharmaceutical agent; depositing a second layer comprising a second pharmaceutical agent; Wherein said first and second pharmaceutical agents are selected from two different classes of pharmaceutical agents.

20 Claims, 31 Drawing Sheets

(56) References Cited

U.S. PATENT DOCUMENTS

| | | |
|---|---|---|
| 4,389,330 A | 6/1983 | Tice et al. |
| 4,474,572 A | 10/1984 | McNaughton et al. |
| 4,474,751 A | 10/1984 | Haslam et al. |
| 4,478,822 A | 10/1984 | Haslam et al. |
| 4,530,840 A | 7/1985 | Tice et al. |
| 4,582,731 A | 4/1986 | Smith |
| 4,606,347 A | 8/1986 | Fogarty et al. |
| 4,617,751 A | 10/1986 | Johansson |
| 4,655,771 A | 4/1987 | Wallsten |
| 4,675,189 A | 6/1987 | Kent et al. |
| 4,733,665 A | 3/1988 | Palmaz |
| 4,734,227 A | 3/1988 | Smith |
| 4,734,451 A | 3/1988 | Smith |
| 4,758,435 A | 7/1988 | Schaaf |
| 4,762,593 A | 8/1988 | Youngner |
| 4,931,037 A | 6/1990 | Wetterman |
| 4,950,239 A | 8/1990 | Gahara et al. |
| 4,985,625 A | 1/1991 | Hurst |
| 5,000,519 A | 3/1991 | Moore |
| 5,090,419 A | 2/1992 | Palestrant |
| 5,096,848 A | 3/1992 | Kawamura |
| 5,102,417 A | 4/1992 | Palmaz |
| 5,104,404 A | 4/1992 | Wolff |
| 5,106,650 A | 4/1992 | Hoy et al. |
| 5,125,570 A | 6/1992 | Jones |
| 5,158,986 A | 10/1992 | Cha et al. |
| 5,185,776 A | 2/1993 | Townsend |
| 5,195,969 A | 3/1993 | Wang et al. |
| 5,243,023 A | 9/1993 | Dezern |
| 5,270,086 A | 12/1993 | Hamlin |
| 5,288,711 A | 2/1994 | Mitchell et al. |
| 5,320,634 A | 6/1994 | Vigil et al. |
| 5,324,049 A | 6/1994 | Mistrater et al. |
| 5,340,614 A | 8/1994 | Perman et al. |
| 5,342,621 A | 8/1994 | Eury |
| 5,350,361 A | 9/1994 | Tsukashima et al. |
| 5,350,627 A | 9/1994 | Nemphos et al. |
| 5,356,433 A | 10/1994 | Rowland et al. |
| 5,360,403 A | 11/1994 | Mische |
| 5,362,718 A | 11/1994 | Skotnicki et al. |
| 5,366,504 A | 11/1994 | Andersen et al. |
| 5,368,045 A | 11/1994 | Clement et al. |
| 5,372,676 A | 12/1994 | Lowe |
| 5,385,776 A | 1/1995 | Maxfield et al. |
| 5,387,313 A | 2/1995 | Thoms |
| 5,403,347 A | 4/1995 | Roby et al. |
| 5,470,603 A | 11/1995 | Staniforth et al. |
| 5,494,620 A | 2/1996 | Liu et al. |
| 5,500,180 A | 3/1996 | Anderson et al. |
| 5,545,208 A | 8/1996 | Wolff et al. |
| 5,556,383 A | 9/1996 | Wang et al. |
| 5,562,922 A | 10/1996 | Lambert |
| 5,569,463 A | 10/1996 | Helmus et al. |
| 5,570,537 A | 11/1996 | Black et al. |
| 5,578,709 A | 11/1996 | Woiszwillo |
| 5,599,576 A | 2/1997 | Opolski |
| 5,607,442 A | 3/1997 | Fischell et al. |
| 5,609,629 A | 3/1997 | Fearnot et al. |
| 5,626,611 A | 5/1997 | Liu et al. |
| 5,626,862 A | 5/1997 | Brem et al. |
| 5,632,772 A | 5/1997 | Alcime et al. |
| 5,669,932 A | 9/1997 | Fischell et al. |
| 5,674,192 A | 10/1997 | Sahatjian et al. |
| 5,674,242 A | 10/1997 | Phan et al. |
| 5,674,286 A | 10/1997 | D'Alessio et al. |
| 5,725,570 A | 3/1998 | Heath |
| 5,733,303 A | 3/1998 | Israel et al. |
| 5,766,158 A | 6/1998 | Opolski |
| 5,800,511 A | 9/1998 | Mayer |
| 5,807,404 A | 9/1998 | Richter |
| 5,811,032 A | 9/1998 | Kawai et al. |
| 5,824,049 A | 10/1998 | Ragheb et al. |
| 5,837,313 A | 11/1998 | Ding et al. |
| 5,843,120 A | 12/1998 | Israel et al. |
| 5,871,436 A | 2/1999 | Eury |
| 5,873,904 A | 2/1999 | Ragheb et al. |
| 5,876,426 A | 3/1999 | Kume et al. |
| 5,913,895 A | 6/1999 | Burpee et al. |
| 5,924,631 A | 7/1999 | Rodrigues et al. |
| 5,948,020 A | 9/1999 | Yoon et al. |
| 5,957,975 A | 9/1999 | Lafont et al. |
| 5,981,568 A | 11/1999 | Kunz et al. |
| 5,981,719 A | 11/1999 | Woiszwillo et al. |
| 6,013,855 A | 1/2000 | McPherson et al. |
| 6,036,978 A | 3/2000 | Gombotz et al. |
| 6,039,721 A | 3/2000 | Johnson et al. |
| 6,068,656 A | 5/2000 | Von Oepen |
| 6,071,308 A | 6/2000 | Ballou et al. |
| 6,077,880 A | 6/2000 | Castillo et al. |
| 6,090,925 A | 7/2000 | Woiszwillo et al. |
| 6,099,562 A | 8/2000 | Ding et al. |
| 6,129,755 A | 10/2000 | Mathis et al. |
| 6,143,037 A | 11/2000 | Goldstein et al. |
| 6,143,314 A | 11/2000 | Chandrashekar et al. |
| 6,146,356 A | 11/2000 | Wang et al. |
| 6,146,404 A | 11/2000 | Kim et al. |
| 6,147,135 A | 11/2000 | Yuan et al. |
| 6,153,252 A | 11/2000 | Hossainy et al. |
| 6,171,327 B1 | 1/2001 | Daniel et al. |
| 6,190,699 B1 | 2/2001 | Luzzi et al. |
| 6,193,744 B1 | 2/2001 | Ehr et al. |
| 6,206,914 B1 | 3/2001 | Soykan et al. |
| 6,217,608 B1 | 4/2001 | Penn et al. |
| 6,231,599 B1 | 5/2001 | Ley |
| 6,231,600 B1 | 5/2001 | Zhong |
| 6,245,104 B1 | 6/2001 | Alt |
| 6,248,127 B1 | 6/2001 | Shah et al. |
| 6,248,129 B1 | 6/2001 | Froix |
| 6,251,980 B1 | 6/2001 | An et al. |
| 6,268,053 B1 | 7/2001 | Woiszwillo et al. |
| 6,273,913 B1 | 8/2001 | Wright et al. |
| 6,284,758 B1 | 9/2001 | Egi et al. |
| 6,299,635 B1 | 10/2001 | Frantzen |
| 6,309,669 B1 | 10/2001 | Setterstrom et al. |
| 6,319,541 B1 | 11/2001 | Pletcher et al. |
| 6,325,821 B1 | 12/2001 | Gaschino et al. |
| 6,336,934 B1 | 1/2002 | Gilson et al. |
| 6,342,062 B1 | 1/2002 | Suon et al. |
| 6,344,055 B1 | 2/2002 | Shukov |
| 6,355,691 B1 | 3/2002 | Goodman |
| 6,358,556 B1 | 3/2002 | Ding et al. |
| 6,361,819 B1 | 3/2002 | Tedeschi et al. |
| 6,362,718 B1 | 3/2002 | Patrick et al. |
| 6,364,903 B2 | 4/2002 | Tseng et al. |
| 6,368,658 B1 | 4/2002 | Schwarz et al. |
| 6,372,246 B1 | 4/2002 | Wei et al. |
| 6,387,121 B1 | 5/2002 | Alt |
| 6,409,716 B1 | 6/2002 | Sahatjian et al. |
| 6,414,050 B1 | 7/2002 | Howdle et al. |
| 6,416,779 B1 | 7/2002 | D'Augustine et al. |
| 6,448,315 B1 | 9/2002 | Lidgren et al. |
| 6,458,387 B1 | 10/2002 | Scott et al. |
| 6,461,380 B1 | 10/2002 | Cox |
| 6,461,644 B1 | 10/2002 | Jackson et al. |
| 6,488,703 B1 | 12/2002 | Kveen et al. |
| 6,495,163 B1 | 12/2002 | Jordan |
| 6,497,729 B1 | 12/2002 | Moussy et al. |
| 6,506,213 B1 | 1/2003 | Mandel et al. |
| 6,511,748 B1 | 1/2003 | Barrows |
| 6,517,860 B1 | 2/2003 | Roser et al. |
| 6,521,258 B1 | 2/2003 | Mandel et al. |
| 6,524,698 B1 | 2/2003 | Schmoock |
| 6,530,951 B1 | 3/2003 | Bates et al. |
| 6,537,310 B1 | 3/2003 | Palmaz et al. |
| 6,541,033 B1 | 4/2003 | Shah |
| 6,572,813 B1 | 6/2003 | Zhang et al. |
| 6,602,281 B1 | 8/2003 | Klein |
| 6,610,013 B1 | 8/2003 | Fenster et al. |
| 6,627,246 B2 | 9/2003 | Mehta et al. |
| 6,649,627 B1 | 11/2003 | Cecchi et al. |
| 6,660,176 B2 | 12/2003 | Tepper et al. |
| 6,669,785 B2 | 12/2003 | DeYoung et al. |
| 6,669,980 B2 | 12/2003 | Hansen |
| 6,670,407 B2 | 12/2003 | Howdle et al. |

(56) References Cited

U.S. PATENT DOCUMENTS

| | | |
|---|---|---|
| 6,682,757 B1 | 1/2004 | Wright |
| 6,706,283 B1 | 3/2004 | Appel et al. |
| 6,710,059 B1 | 3/2004 | Labrie et al. |
| 6,720,003 B2 | 4/2004 | Chen et al. |
| 6,723,913 B1 | 4/2004 | Barbetta |
| 6,726,712 B1 | 4/2004 | Raeder-Devens et al. |
| 6,736,996 B1 | 5/2004 | Carbonell et al. |
| 6,743,505 B2 | 6/2004 | Antal et al. |
| 6,749,902 B2 | 6/2004 | Yonker et al. |
| 6,755,871 B2 | 6/2004 | Damaso et al. |
| 6,756,084 B2 | 6/2004 | Fulton et al. |
| 6,767,558 B2 | 7/2004 | Wang |
| 6,780,475 B2 | 8/2004 | Fulton et al. |
| 6,794,902 B2 | 9/2004 | Becker et al. |
| 6,800,663 B2 | 10/2004 | Asgarzadeh et al. |
| 6,815,218 B1 | 11/2004 | Jacobson et al. |
| 6,821,549 B2 | 11/2004 | Jayaraman |
| 6,837,611 B2 | 1/2005 | Kuo |
| 6,838,089 B1 | 1/2005 | Carlsson et al. |
| 6,838,528 B2 | 1/2005 | Zhao |
| 6,858,598 B1 | 2/2005 | McKearn et al. |
| 6,860,123 B1 | 3/2005 | Uhlin |
| 6,868,123 B2 | 3/2005 | Uhlin |
| 6,884,377 B1 | 4/2005 | Burnham et al. |
| 6,884,823 B1 | 4/2005 | Pierick et al. |
| 6,897,205 B2 | 5/2005 | Beckert et al. |
| 6,905,555 B2 | 6/2005 | DeYoung et al. |
| 6,908,624 B2 | 6/2005 | Hossainy et al. |
| 6,916,800 B2 | 7/2005 | McKearn et al. |
| 6,923,979 B2 | 8/2005 | Fotland et al. |
| 6,936,270 B2 | 8/2005 | Watson et al. |
| 6,939,569 B1 | 9/2005 | Green et al. |
| 6,973,718 B2 | 12/2005 | Sheppard, Jr. et al. |
| 7,056,591 B1 | 6/2006 | Pacetti et al. |
| 7,094,256 B1 | 8/2006 | Shah et al. |
| 7,148,201 B2 | 12/2006 | Stern et al. |
| 7,152,452 B2 | 12/2006 | Kokish |
| 7,160,592 B2 | 1/2007 | Rypacek et al. |
| 7,163,715 B1 | 1/2007 | Kramer |
| 7,169,404 B2 | 1/2007 | Hossainy et al. |
| 7,171,255 B2 | 1/2007 | Holupka et al. |
| 7,201,750 B1 | 4/2007 | Eggers et al. |
| 7,201,940 B1 | 4/2007 | Kramer |
| 7,229,837 B2 | 6/2007 | Chen |
| 7,278,174 B2 | 10/2007 | Villalobos |
| 7,279,174 B2 | 10/2007 | Pacetti et al. |
| 7,282,020 B2 | 10/2007 | Kaplan |
| 7,308,748 B2 | 12/2007 | Kokish |
| 7,323,454 B2 | 1/2008 | De Nijs et al. |
| 7,326,734 B2 | 2/2008 | Zi et al. |
| 7,329,383 B2 | 2/2008 | Stinson |
| 7,378,105 B2 | 5/2008 | Burke et al. |
| 7,419,696 B2 | 9/2008 | Berg et al. |
| 7,429,378 B2 | 9/2008 | Serhan et al. |
| 7,444,162 B2 | 10/2008 | Hassan |
| 7,455,658 B2 | 11/2008 | Wang |
| 7,455,688 B2 | 11/2008 | Furst et al. |
| 7,456,151 B2 | 11/2008 | Li et al. |
| 7,462,593 B2 | 12/2008 | Cuttitta et al. |
| 7,485,113 B2 | 2/2009 | Varner et al. |
| 7,498,042 B2 | 3/2009 | Gaki et al. |
| 7,524,865 B2 | 4/2009 | D'Amato et al. |
| 7,537,610 B2 | 5/2009 | Reiss |
| 7,537,785 B2 | 5/2009 | Loscalzo et al. |
| 7,553,827 B2 | 6/2009 | Attawia et al. |
| 7,713,538 B2 | 5/2010 | Lewis et al. |
| 7,727,275 B2 | 6/2010 | Betts et al. |
| 7,745,566 B2 | 6/2010 | Chattopadhyay et al. |
| 7,763,277 B1 | 7/2010 | Canham et al. |
| 7,771,468 B2 | 8/2010 | Whitbourne et al. |
| 7,837,726 B2 | 11/2010 | Von Oepen et al. |
| 7,842,312 B2 | 11/2010 | Burgermeister et al. |
| 7,919,108 B2 | 4/2011 | Reyes et al. |
| 7,955,383 B2 | 6/2011 | Krivoruchko et al. |
| 7,967,855 B2 | 6/2011 | Furst et al. |
| 7,972,661 B2 | 7/2011 | Pui et al. |
| 8,070,796 B2 | 12/2011 | Furst et al. |
| 8,295,565 B2 | 10/2012 | Gu et al. |
| 8,298,565 B2 | 10/2012 | Taylor et al. |
| 8,333,803 B2 | 12/2012 | Park et al. |
| 8,377,356 B2 | 2/2013 | Huang et al. |
| 8,535,372 B2 | 9/2013 | Fox et al. |
| 8,709,071 B1 | 4/2014 | Huang et al. |
| 8,753,659 B2 | 6/2014 | Lewis et al. |
| 8,753,709 B2 | 6/2014 | Hossainy et al. |
| 8,758,429 B2 | 6/2014 | Taylor et al. |
| 8,795,762 B2 | 8/2014 | Fulton et al. |
| 8,834,913 B2 | 9/2014 | Shaw et al. |
| 8,852,625 B2 | 10/2014 | DeYoung et al. |
| 8,900,651 B2 | 12/2014 | McClain et al. |
| 9,090,029 B2 | 7/2015 | Prevost |
| 9,433,516 B2 | 9/2016 | McClain et al. |
| 2001/0026804 A1 | 10/2001 | Boutignon |
| 2001/0034336 A1 | 10/2001 | Shah et al. |
| 2001/0044629 A1 | 11/2001 | Stinson |
| 2001/0049551 A1 | 12/2001 | Tseng et al. |
| 2002/0007209 A1 | 1/2002 | Scheerder et al. |
| 2002/0051485 A1 | 5/2002 | Bottomley |
| 2002/0051845 A1 | 5/2002 | Mehta et al. |
| 2002/0058019 A1 | 5/2002 | Berenson et al. |
| 2002/0082679 A1 | 6/2002 | Sirhan et al. |
| 2002/0082680 A1 | 6/2002 | Shanley et al. |
| 2002/0091433 A1 | 7/2002 | Ding et al. |
| 2002/0099332 A1 | 7/2002 | Slepian et al. |
| 2002/0125860 A1 | 9/2002 | Schworm et al. |
| 2002/0133072 A1 | 9/2002 | Wang et al. |
| 2002/0144757 A1 | 10/2002 | Craig et al. |
| 2003/0001830 A1 | 1/2003 | Wampler et al. |
| 2003/0004563 A1 | 1/2003 | Jackson et al. |
| 2003/0028244 A1 | 2/2003 | Bates et al. |
| 2003/0031699 A1 | 2/2003 | Van Antwerp |
| 2003/0077200 A1 | 4/2003 | Craig et al. |
| 2003/0088307 A1 | 5/2003 | Shulze et al. |
| 2003/0125800 A1 | 7/2003 | Shulze et al. |
| 2003/0143315 A1 | 7/2003 | Pui et al. |
| 2003/0170305 A1 | 9/2003 | O'Neil et al. |
| 2003/0180376 A1 | 9/2003 | Dalal et al. |
| 2003/0185964 A1 | 10/2003 | Weber et al. |
| 2003/0204238 A1 | 10/2003 | Tedeschi |
| 2003/0222017 A1 | 12/2003 | Fulton et al. |
| 2003/0222018 A1 | 12/2003 | Yonker et al. |
| 2003/0232014 A1 | 12/2003 | Burke et al. |
| 2004/0013792 A1 | 1/2004 | Epstein et al. |
| 2004/0018228 A1 | 1/2004 | Fischell et al. |
| 2004/0022400 A1 | 2/2004 | Magrath |
| 2004/0022853 A1 | 2/2004 | Ashton et al. |
| 2004/0044397 A1 | 3/2004 | Stinson |
| 2004/0059290 A1 | 3/2004 | Palasis |
| 2004/0102758 A1 | 5/2004 | Davila et al. |
| 2004/0106982 A1 | 6/2004 | Jalisi |
| 2004/0122205 A1 | 6/2004 | Nathan |
| 2004/0126542 A1 | 7/2004 | Fujiwara et al. |
| 2004/0143317 A1 | 7/2004 | Stinson et al. |
| 2004/0144317 A1 | 7/2004 | Chuman et al. |
| 2004/0147904 A1 | 7/2004 | Hung et al. |
| 2004/0148007 A1 | 7/2004 | Jackson et al. |
| 2004/0157789 A1 | 8/2004 | Geall |
| 2004/0170685 A1 | 9/2004 | Carpenter et al. |
| 2004/0181278 A1 | 9/2004 | Tseng et al. |
| 2004/0193177 A1 | 9/2004 | Houghton et al. |
| 2004/0193262 A1 | 9/2004 | Shadduck |
| 2004/0220660 A1 | 11/2004 | Shanley et al. |
| 2004/0224001 A1 | 11/2004 | Pacetti et al. |
| 2004/0234748 A1 | 11/2004 | Stenzel |
| 2004/0236416 A1 | 11/2004 | Falotico |
| 2004/0260000 A1 | 12/2004 | Chaiko |
| 2005/0003074 A1 | 1/2005 | Brown et al. |
| 2005/0004661 A1 | 1/2005 | Lewis et al. |
| 2005/0010275 A1 | 1/2005 | Sahatjian et al. |
| 2005/0015046 A1 | 1/2005 | Weber et al. |
| 2005/0019747 A1 | 1/2005 | Anderson et al. |
| 2005/0033414 A1 | 2/2005 | Zhang et al. |
| 2005/0038498 A1 | 2/2005 | Dubrow et al. |
| 2005/0048121 A1 | 3/2005 | East et al. |

(56) References Cited

U.S. PATENT DOCUMENTS

| | | |
|---|---|---|
| 2005/0049694 A1 | 3/2005 | Neary |
| 2005/0053639 A1 | 3/2005 | Shalaby |
| 2005/0055078 A1 | 3/2005 | Campbell |
| 2005/0060028 A1 | 3/2005 | Horres et al. |
| 2005/0069630 A1 | 3/2005 | Fox et al. |
| 2005/0070989 A1 | 3/2005 | Lye et al. |
| 2005/0070990 A1 | 3/2005 | Stinson |
| 2005/0074479 A1 | 4/2005 | Weber et al. |
| 2005/0075714 A1 | 4/2005 | Cheng et al. |
| 2005/0079199 A1 | 4/2005 | Heruth et al. |
| 2005/0079274 A1 | 4/2005 | Palasis et al. |
| 2005/0084533 A1 | 4/2005 | Howdle et al. |
| 2005/0095267 A1 | 5/2005 | Campbell et al. |
| 2005/0131008 A1 | 6/2005 | Betts et al. |
| 2005/0131513 A1 | 6/2005 | Myers |
| 2005/0147734 A1 | 7/2005 | Seppala et al. |
| 2005/0159704 A1 | 7/2005 | Scott et al. |
| 2005/0166841 A1 | 8/2005 | Robida |
| 2005/0175772 A1 | 8/2005 | Worsham et al. |
| 2005/0176678 A1 | 8/2005 | Horres et al. |
| 2005/0177223 A1 | 8/2005 | Palmaz |
| 2005/0191491 A1 | 9/2005 | Wang et al. |
| 2005/0196424 A1 | 9/2005 | Chappa |
| 2005/0208102 A1 | 9/2005 | Schultz |
| 2005/0209244 A1 | 9/2005 | Prescott et al. |
| 2005/0209680 A1 | 9/2005 | Gale et al. |
| 2005/0216075 A1 | 9/2005 | Wang et al. |
| 2005/0220839 A1 | 10/2005 | DeWitt et al. |
| 2005/0222676 A1 | 10/2005 | Shanley et al. |
| 2005/0233061 A1 | 10/2005 | Schwarz |
| 2005/0238829 A1 | 10/2005 | Motherwell et al. |
| 2005/0245637 A1 | 11/2005 | Hossainy et al. |
| 2005/0255327 A1 | 11/2005 | Chaney et al. |
| 2005/0260186 A1 | 11/2005 | Bookbinder et al. |
| 2005/0268573 A1 | 12/2005 | Yan |
| 2005/0288481 A1 | 12/2005 | DesNoyer et al. |
| 2005/0288629 A1 | 12/2005 | Kunis |
| 2006/0001011 A1 | 1/2006 | Wilson et al. |
| 2006/0002974 A1 | 1/2006 | Pacetti et al. |
| 2006/0020325 A1 | 1/2006 | Burgermeister et al. |
| 2006/0030652 A1 | 2/2006 | Adams et al. |
| 2006/0045901 A1 | 3/2006 | Weber |
| 2006/0067974 A1 | 3/2006 | Labrecque et al. |
| 2006/0073329 A1 | 4/2006 | Boyce et al. |
| 2006/0089705 A1 | 4/2006 | Ding et al. |
| 2006/0093771 A1 | 5/2006 | Rypacek et al. |
| 2006/0094744 A1 | 5/2006 | Maryanoff et al. |
| 2006/0106455 A1 | 5/2006 | Furst et al. |
| 2006/0116755 A1 | 6/2006 | Stinson |
| 2006/0121080 A1 | 6/2006 | Lye et al. |
| 2006/0121089 A1 | 6/2006 | Michal et al. |
| 2006/0134168 A1 | 6/2006 | Chappa et al. |
| 2006/0134211 A1 | 6/2006 | Lien et al. |
| 2006/0136041 A1 | 6/2006 | Schmid et al. |
| 2006/0147698 A1 | 7/2006 | Carroll et al. |
| 2006/0153729 A1 | 7/2006 | Stinson et al. |
| 2006/0160455 A1 | 7/2006 | Sugyo et al. |
| 2006/0188547 A1 | 8/2006 | S. Bezwada |
| 2006/0193886 A1 | 8/2006 | Owens et al. |
| 2006/0193890 A1 | 8/2006 | Owens et al. |
| 2006/0198868 A1 | 9/2006 | DeWitt et al. |
| 2006/0210638 A1 | 9/2006 | Liversidge et al. |
| 2006/0216324 A1 | 9/2006 | Stucke et al. |
| 2006/0222756 A1 | 10/2006 | Davila et al. |
| 2006/0228415 A1 | 10/2006 | Oberegger et al. |
| 2006/0228453 A1 | 10/2006 | Cromack et al. |
| 2006/0235505 A1 | 10/2006 | Oepen et al. |
| 2006/0235506 A1 | 10/2006 | Ta et al. |
| 2006/0276877 A1 | 12/2006 | Owens et al. |
| 2006/0287611 A1 | 12/2006 | Fleming |
| 2007/0009564 A1 | 1/2007 | McClain et al. |
| 2007/0009664 A1 | 1/2007 | Fallais et al. |
| 2007/0026042 A1 | 2/2007 | Narayanan |
| 2007/0032864 A1 | 2/2007 | Furst et al. |
| 2007/0038227 A1 | 2/2007 | Massicotte et al. |
| 2007/0038289 A1 | 2/2007 | Nishide et al. |
| 2007/0043434 A1 | 2/2007 | Meerkin et al. |
| 2007/0059350 A1 | 3/2007 | Kennedy et al. |
| 2007/0065478 A1 | 3/2007 | Hossainy |
| 2007/0078513 A1 | 4/2007 | Campbell |
| 2007/0110888 A1 | 5/2007 | Radhakrishnan et al. |
| 2007/0123973 A1 | 5/2007 | Roth et al. |
| 2007/0123977 A1 | 5/2007 | Cottone et al. |
| 2007/0128274 A1 | 6/2007 | Zhu et al. |
| 2007/0148251 A1 | 6/2007 | Hossainy et al. |
| 2007/0154513 A1 | 7/2007 | Atanasoska et al. |
| 2007/0154554 A1 | 7/2007 | Burgermeister et al. |
| 2007/0196242 A1 | 8/2007 | Boozer et al. |
| 2007/0196423 A1 | 8/2007 | Ruane et al. |
| 2007/0198081 A1 | 8/2007 | Castro et al. |
| 2007/0200268 A1 | 8/2007 | Dave |
| 2007/0203569 A1 | 8/2007 | Burgermeister et al. |
| 2007/0219579 A1 | 9/2007 | Paul |
| 2007/0225795 A1 | 9/2007 | Granada et al. |
| 2007/0250157 A1 | 10/2007 | Nishide et al. |
| 2007/0250159 A1 | 10/2007 | Davis |
| 2007/0259017 A1 | 11/2007 | Francis |
| 2007/0280992 A1 | 12/2007 | Margaron et al. |
| 2008/0030066 A1 | 2/2008 | Mercier et al. |
| 2008/0051866 A1 | 2/2008 | Chen et al. |
| 2008/0065192 A1 | 3/2008 | Berglund |
| 2008/0071347 A1 | 3/2008 | Cambronne |
| 2008/0071358 A1 | 3/2008 | Weber et al. |
| 2008/0071359 A1 | 3/2008 | Thornton et al. |
| 2008/0075753 A1 | 3/2008 | Chappa |
| 2008/0077232 A1 | 3/2008 | Nishide |
| 2008/0085880 A1 | 4/2008 | Viswanath et al. |
| 2008/0095919 A1 | 4/2008 | McClain et al. |
| 2008/0097575 A1 | 4/2008 | Cottone |
| 2008/0097591 A1 | 4/2008 | Savage et al. |
| 2008/0098178 A1 | 4/2008 | Veazey et al. |
| 2008/0107702 A1 | 5/2008 | Jennissen |
| 2008/0118543 A1 | 5/2008 | Pacetti et al. |
| 2008/0124372 A1 | 5/2008 | Hossainy et al. |
| 2008/0138375 A1 | 6/2008 | Yan et al. |
| 2008/0206304 A1 | 8/2008 | Lindquist et al. |
| 2008/0213464 A1 | 9/2008 | O'Connor |
| 2008/0233267 A1 | 9/2008 | Berglund |
| 2008/0255510 A1 | 10/2008 | Wang |
| 2008/0269449 A1 | 10/2008 | Chattopadhyay et al. |
| 2008/0286325 A1 | 11/2008 | Reyes et al. |
| 2008/0292776 A1 | 11/2008 | Dias et al. |
| 2008/0300669 A1 | 12/2008 | Hossainy |
| 2008/0300689 A1 | 12/2008 | Mc Kinnon et al. |
| 2009/0043379 A1 | 2/2009 | Prescott |
| 2009/0062909 A1 | 3/2009 | Taylor et al. |
| 2009/0068266 A1 | 3/2009 | Raheja et al. |
| 2009/0076446 A1 | 3/2009 | Dubuclet, IV et al. |
| 2009/0082855 A1 | 3/2009 | Borges et al. |
| 2009/0098178 A1 | 4/2009 | Hofmann et al. |
| 2009/0105687 A1 | 4/2009 | Deckman et al. |
| 2009/0105809 A1 | 4/2009 | Lee et al. |
| 2009/0110711 A1 | 4/2009 | Trollsas et al. |
| 2009/0111787 A1 | 4/2009 | Lim et al. |
| 2009/0123515 A1 | 5/2009 | Taylor et al. |
| 2009/0123521 A1 | 5/2009 | Weber et al. |
| 2009/0186069 A1 | 7/2009 | DeYoung et al. |
| 2009/0202609 A1 | 8/2009 | Keough et al. |
| 2009/0216317 A1 | 8/2009 | Cromack et al. |
| 2009/0227949 A1 | 9/2009 | Knapp et al. |
| 2009/0231578 A1 | 9/2009 | Ling et al. |
| 2009/0263460 A1 | 10/2009 | McDonald |
| 2009/0285974 A1 | 11/2009 | Kerrigan et al. |
| 2009/0292351 A1 | 11/2009 | McClain et al. |
| 2009/0292776 A1 | 11/2009 | Nesbitt et al. |
| 2009/0297578 A1 | 12/2009 | Trollsas et al. |
| 2009/0300689 A1 | 12/2009 | Conte et al. |
| 2010/0000328 A1 | 1/2010 | Mahmoud |
| 2010/0006358 A1 | 1/2010 | Ishikawa |
| 2010/0015200 A1 | 1/2010 | McClain et al. |
| 2010/0030261 A1 | 2/2010 | McClain |
| 2010/0042206 A1 | 2/2010 | Yadav et al. |
| 2010/0055145 A1 | 3/2010 | Betts et al. |
| 2010/0055294 A1 | 3/2010 | Wang et al. |

(56) References Cited

U.S. PATENT DOCUMENTS

| | | | |
|---|---|---|---|
| 2010/0063570 A1 | 3/2010 | Pacetti et al. |
| 2010/0063580 A1 | 3/2010 | McClain et al. |
| 2010/0074934 A1 | 3/2010 | Hunter |
| 2010/0131044 A1 | 5/2010 | Patel |
| 2010/0137491 A1 | 6/2010 | Rose et al. |
| 2010/0155496 A1 | 6/2010 | Stark et al. |
| 2010/0166869 A1 | 7/2010 | Desai et al. |
| 2010/0196482 A1 | 8/2010 | Radovic-Moreno et al. |
| 2010/0198330 A1 | 8/2010 | Hossainy et al. |
| 2010/0198331 A1 | 8/2010 | Rapoza et al. |
| 2010/0211164 A1 | 8/2010 | McClain et al. |
| 2010/0228348 A1 | 9/2010 | McClain et al. |
| 2010/0233332 A1 | 9/2010 | King et al. |
| 2010/0239635 A1 | 9/2010 | McClain et al. |
| 2010/0241220 A1 | 9/2010 | McClain et al. |
| 2010/0256746 A1 | 10/2010 | Taylor et al. |
| 2010/0256748 A1 | 10/2010 | Taylor et al. |
| 2010/0262224 A1 | 10/2010 | Kleiner |
| 2010/0272775 A1 | 10/2010 | Cleek et al. |
| 2010/0272778 A1 | 10/2010 | McClain et al. |
| 2010/0285085 A1 | 11/2010 | Stankus et al. |
| 2010/0298928 A1 | 11/2010 | McClain et al. |
| 2010/0303881 A1 | 12/2010 | Hoke et al. |
| 2010/0305689 A1 | 12/2010 | Venkatraman et al. |
| 2011/0009953 A1 | 1/2011 | Luk et al. |
| 2011/0034422 A1 | 2/2011 | Kannan et al. |
| 2011/0159069 A1 | 6/2011 | Shaw et al. |
| 2011/0160751 A1 | 6/2011 | Granja Filho |
| 2011/0172763 A1 | 7/2011 | Ndondo-Lay |
| 2011/0190864 A1 | 8/2011 | McClain et al. |
| 2011/0223212 A1 | 9/2011 | Taton et al. |
| 2011/0238161 A1 | 9/2011 | Fulton et al. |
| 2011/0257732 A1 | 10/2011 | McClain et al. |
| 2011/0264190 A1 | 10/2011 | McClain et al. |
| 2011/0301697 A1 | 12/2011 | Hoffmann et al. |
| 2012/0064124 A1 | 3/2012 | McClain et al. |
| 2012/0064143 A1 | 3/2012 | Sharp et al. |
| 2012/0065723 A1 | 3/2012 | Drasler et al. |
| 2012/0101566 A1 | 4/2012 | Mews et al. |
| 2012/0150275 A1 | 6/2012 | Shaw-Klein |
| 2012/0160408 A1 | 6/2012 | Clerc et al. |
| 2012/0172787 A1 | 7/2012 | McClain et al. |
| 2012/0177742 A1 | 7/2012 | McClain et al. |
| 2012/0231037 A1 | 9/2012 | Levi et al. |
| 2012/0239161 A1 | 9/2012 | Datta et al. |
| 2012/0271396 A1 | 10/2012 | Zheng et al. |
| 2012/0280432 A1 | 11/2012 | Chen et al. |
| 2012/0290075 A1 | 11/2012 | Mortisen et al. |
| 2012/0323311 A1 | 12/2012 | McClain et al. |
| 2013/0006351 A1 | 1/2013 | Taylor et al. |
| 2013/0035754 A1 | 2/2013 | Shulze et al. |
| 2013/0087270 A1 | 4/2013 | Hossainy et al. |
| 2013/0110138 A1 | 5/2013 | Hurtado et al. |
| 2013/0172853 A1 | 7/2013 | McClain et al. |
| 2013/0291476 A1 | 11/2013 | Broughton, Jr. et al. |
| 2014/0343667 A1 | 11/2014 | McClain |
| 2014/0350522 A1 | 11/2014 | McClain et al. |
| 2014/0371717 A1 | 12/2014 | McClain et al. |
| 2015/0024116 A1 | 1/2015 | Matson et al. |
| 2015/0025620 A1 | 1/2015 | Taylor et al. |
| 2016/0095726 A1 | 4/2016 | McClain et al. |

FOREIGN PATENT DOCUMENTS

| | | |
|---|---|---|
| CA | 2615452 A1 | 1/2007 |
| CA | 2650590 A1 | 11/2007 |
| CA | 2679712 A1 | 7/2008 |
| CA | 2684482 A1 | 10/2008 |
| CA | 2721832 A1 | 12/2009 |
| CN | 2423899 Y | 3/2001 |
| CN | 1465410 A | 1/2004 |
| CN | 1575860 A | 2/2005 |
| CN | 1649551 A | 8/2005 |
| CN | 1684641 A | 10/2005 |
| CN | 101161300 A | 4/2008 |
| CN | 102481195 A | 5/2012 |
| DE | 4336209 A1 | 3/1995 |
| DE | 29702671 U1 | 4/1997 |
| DE | 29716476 U1 | 12/1997 |
| DE | 19633901 A1 | 2/1998 |
| DE | 29716467 U1 | 2/1998 |
| DE | 19740506 A1 | 3/1998 |
| DE | 19754870 A1 | 8/1998 |
| DE | 19822157 A1 | 11/1999 |
| DE | 69611186 T2 | 5/2001 |
| EP | 0335341 | 10/1989 |
| EP | 0604022 A1 | 6/1994 |
| EP | 800801 A1 | 10/1997 |
| EP | 0876806 A1 | 11/1998 |
| EP | 0982041 A1 | 3/2000 |
| EP | 1195822 A2 | 4/2002 |
| EP | 1325758 A2 | 7/2003 |
| EP | 1327422 A1 | 7/2003 |
| EP | 1454677 A2 | 9/2004 |
| EP | 1502655 A2 | 2/2005 |
| EP | 1810665 A1 | 7/2007 |
| EP | 1909973 A2 | 4/2008 |
| EP | 2197070 A1 | 6/2010 |
| EP | 2293357 A1 | 3/2011 |
| EP | 2293366 A1 | 3/2011 |
| FR | 2758253 A1 | 7/1998 |
| JP | 698902 | 4/1994 |
| JP | H06218063 A | 8/1994 |
| JP | H08206223 A | 8/1996 |
| JP | H0956807 A | 3/1997 |
| JP | H10295824 A | 2/1998 |
| JP | H10151207 A | 6/1998 |
| JP | 110314313 A | 12/1998 |
| JP | H1157018 A | 3/1999 |
| JP | 2000316981 A | 11/2000 |
| JP | 2001521503 A | 11/2001 |
| JP | 2003205037 A | 7/2003 |
| JP | 2003533286 A | 11/2003 |
| JP | 2003533492 A | 11/2003 |
| JP | 2003533493 A | 11/2003 |
| JP | 2004512059 A | 4/2004 |
| JP | 2004173770 A | 6/2004 |
| JP | 2004518458 A | 6/2004 |
| JP | 2004528060 A | 9/2004 |
| JP | 2004529674 A | 9/2004 |
| JP | 2005505318 | 2/2005 |
| JP | 2005519080 A | 6/2005 |
| JP | 2005523119 A | 8/2005 |
| JP | 2005523332 A | 8/2005 |
| JP | 2005296690 A | 10/2005 |
| JP | 2006506191 A | 2/2006 |
| JP | 2006512175 A | 4/2006 |
| JP | 2007502281 A | 2/2007 |
| JP | 2009501566 A | 1/2009 |
| WO | 9409010 A1 | 4/1994 |
| WO | 9506487 A2 | 3/1995 |
| WO | 9616691 A1 | 6/1996 |
| WO | 9620698 A2 | 7/1996 |
| WO | 9632907 A1 | 10/1996 |
| WO | 9641807 A1 | 12/1996 |
| WO | 9745502 A1 | 12/1997 |
| WO | 9802441 A2 | 1/1998 |
| WO | 9908729 A1 | 2/1999 |
| WO | 9915530 A1 | 4/1999 |
| WO | 9917680 A1 | 4/1999 |
| WO | 99016388 A1 | 4/1999 |
| WO | 0006051 A1 | 2/2000 |
| WO | 0025702 A1 | 5/2000 |
| WO | 00032238 A1 | 6/2000 |
| WO | 0114387 A1 | 3/2001 |
| WO | 2001054662 | 8/2001 |
| WO | 0187345 A1 | 11/2001 |
| WO | 0187368 A1 | 11/2001 |
| WO | 0187372 A1 | 11/2001 |
| WO | 01087371 A2 | 11/2001 |
| WO | 0240702 | 5/2002 |
| WO | 0243799 | 6/2002 |
| WO | 02055122 A1 | 7/2002 |
| WO | 02074194 A2 | 9/2002 |

(56) References Cited

FOREIGN PATENT DOCUMENTS

| | | | |
|---|---|---|---|
| WO | 02090085 A1 | 11/2002 |
| WO | 02100456 A1 | 12/2002 |
| WO | 03039553 A1 | 5/2003 |
| WO | 03082368 A1 | 10/2003 |
| WO | 03090684 A2 | 11/2003 |
| WO | 03101624 A1 | 12/2003 |
| WO | 2004009145 A1 | 1/2004 |
| WO | 2004028406 A1 | 4/2004 |
| WO | 2004028589 A2 | 4/2004 |
| WO | 2004043506 A1 | 5/2004 |
| WO | 2004045450 A2 | 6/2004 |
| WO | 04098574 A1 | 11/2004 |
| WO | 2004101017 A2 | 11/2004 |
| WO | 05042623 A1 | 5/2005 |
| WO | 2005063319 A1 | 7/2005 |
| WO | 05069889 A2 | 8/2005 |
| WO | 2005117942 A2 | 12/2005 |
| WO | 2006014534 A2 | 2/2006 |
| WO | 2006052575 A2 | 5/2006 |
| WO | 2006063021 A2 | 6/2006 |
| WO | 2006063430 A1 | 6/2006 |
| WO | 2006065685 A2 | 6/2006 |
| WO | 06083796 A2 | 8/2006 |
| WO | 2006099276 A2 | 9/2006 |
| WO | 07002238 A2 | 1/2007 |
| WO | 2007011707 A2 | 1/2007 |
| WO | 2007011708 A2 | 1/2007 |
| WO | 2007017707 A2 | 1/2007 |
| WO | 2007017708 A3 | 1/2007 |
| WO | 07092179 A2 | 8/2007 |
| WO | 2007127363 A2 | 11/2007 |
| WO | 07143609 A2 | 12/2007 |
| WO | 08046641 A2 | 4/2008 |
| WO | 08046642 A2 | 4/2008 |
| WO | 2008042909 A2 | 4/2008 |
| WO | 2008052000 A2 | 5/2008 |
| WO | 2008070996 A1 | 6/2008 |
| WO | 2008086369 A1 | 7/2008 |
| WO | 2008131131 A1 | 10/2008 |
| WO | 2008148013 A1 | 12/2008 |
| WO | 09039553 A1 | 4/2009 |
| WO | 09051614 A1 | 4/2009 |
| WO | 2009051780 A1 | 4/2009 |
| WO | 2009146209 A1 | 12/2009 |
| WO | 2010009335 A1 | 1/2010 |
| WO | 10075590 A2 | 7/2010 |
| WO | 2010086863 A2 | 8/2010 |
| WO | 2010111196 A2 | 9/2010 |
| WO | 2010111232 A2 | 9/2010 |
| WO | 2010111238 A2 | 9/2010 |
| WO | 2010120552 A2 | 10/2010 |
| WO | 2010121187 A2 | 10/2010 |
| WO | 10136604 A1 | 12/2010 |
| WO | 2011009096 A1 | 1/2011 |
| WO | 2011097103 A1 | 8/2011 |
| WO | 11119762 A1 | 9/2011 |
| WO | 2011119159 A1 | 9/2011 |
| WO | 11130448 A1 | 10/2011 |
| WO | 11133655 A1 | 10/2011 |
| WO | 12009684 A2 | 1/2012 |
| WO | 12034079 A2 | 3/2012 |
| WO | 2012078955 A1 | 6/2012 |
| WO | 2012082502 A1 | 6/2012 |
| WO | 12092504 A2 | 7/2012 |
| WO | 12142319 A1 | 10/2012 |
| WO | 12166819 A1 | 12/2012 |
| WO | 2013012689 A1 | 1/2013 |
| WO | 2013025535 A1 | 2/2013 |
| WO | 13059509 A1 | 4/2013 |
| WO | 13177211 A1 | 11/2013 |
| WO | 2013173657 A1 | 11/2013 |
| WO | 2014063111 A1 | 4/2014 |
| WO | 2014165264 A1 | 10/2014 |
| WO | 2014186532 A1 | 11/2014 |
| WO | 2015181826 A1 | 12/2015 |

OTHER PUBLICATIONS

PCT/US06/27321 Written Opinion dated Oct. 16, 2007.

Machtle and Borger, Analytical Ultracentrifugation of Polymers and Nanoparticles, W. Machtle and L. Borger, (Springer) 2006, p. 41.

Lewis, D. H., "Controlled Release of Bioactive Agents from Lactides/Glycolide Polymers" in Biodegradable Polymers as Drug Delivery Systems, Chasin, M. and Langer, R., eds., Marcel Decker (1990).

Luzzi, L.A.,, Microencapsulation, J. Pharm. Sciences, vol. 59, No. 10, Oct. 1970, pp. 1367-1376.

Park et al., Mechanisms of Mucoadhesion of Poly(acrylic Acid) Hydrogels, Pharm. Res. (1987) vol. 4, No. 6, pp. 457-464.

PCT/US11/33225 International Search Report and Written Opinion dated Jul. 7, 2011.

Ji, et al., "96-Wellliquid-liquid extraction liquid chromatographytandem mass spectrometry method for the quantitative determination of ABT-578 in human blood samples" Journal of Chromatography B. 805:67-75 (2004).

Levit, et al., "Supercritical C02 Assisted Electrospinning" J. of Supercritical Fluids, 329-333, vol. 31, Issue 3, (Nov. 2004).

Handschumacher, R.E. and Cheng, Y-C., Purine and Pyrimidine Antimetabolites, In: Cancer Medicine, pp. 712-732, Ch. XV1-2, 3rd Edition, Edited by J. Holland and E. Frei III (eds.), Lea and Febiger, 1992.

Higuchi, Rate of Release of Medicaments from Ointment Bases Containing Drugs in Suspension, Journal of Pharmaceutical Sciences, vol. 50, No. 10, p. 874, Oct. 1961.

David Grant, Crystallization Impact on the Nature and Properties of the Crystalline Product, 2003, SSCI, http://www.ssci-inc.com/Information/RecentPublications/ApplicationNotes/CrystallizationImpact/tabid/138/Default.aspx.

Extended European Search Report for Application No. 14797966.0 dated Dec. 19, 2016.

Search Report from Singapore Application No. 2013054127 dated Jul. 26, 2017, 5 pages.

Datenblatt NIRflex®der Firma Medinol, NIRFlex TM Premounted Coronary Stent System, Instructions for Use, Medinol Ingenuity for Life, Doc #912000012 Draft F, Oct. 8, 2003, 18 pages.

Stoeckel et al., "A survey of stent designs", Minimally Invasive Therapy & Allied Technologies, Jan. 2002, 11 (4), Seite 137-147.

Stent: Medline Plus Medical Encyclopedia, National Institutes of Health / U.S. National Library of Medicine, last updated Mar. 23, 2020 <https://medlineplus.gov/ency/article/002303.htm>, 4 pages.

Medtronic, "EverFlex Self-expanding Peripheral Stent / Vascular Stenting", last updated Nov. 2017, <https://www.medtronic.com/us-en/healthcareprofessionals/products/cardiovascular/peripheral-biliary-stents/everflex.html>, 6 pages.

Medtronic, "IntraStent DoubleStrut LD Biliary Stents", last updated Nov. 2017, <https://www.medtronic.com/us-en/healthcareprofessionals/products/ cardiovascular/peripheral-biliary-stents/intrastentdoublestrut-Id-biliary-stent.html>, 4 pages.

Medtronic, "Indications, Safety, and Warnings / IntraStent DoubleStrut LD Biliary Stents", <https://www.medtronic.com/us-en/healthcareprofessionals/products/cardiovascular/peripheral-biliary-stents/intrastentdoublestrut-Id-biliarv-stent/indicationssafety-warnings.html>, last updated Nov. 2017, 2 pages.

"Guidance for Industry / Coronary Drug-Eluting Stents Nonclinical and Clinical Studies", U.S. Department of Health and Human Services Food Drug Adminstration Center for Devices and Radiological Health (CDRH), Center for Drug-Evaluation and Research (CDER), Mar. 2008, <https://www.fda.gov/media/71521/download>, 89 pages.

U.S. Department of Health and Human Services Food and Drug Administration Center for Devices and Radiological Health, "Metal Expandable Biliary Stents—Premarket Notificarion (510(k)) Submissions / Guidance for Industry and Food and Drug Administration Staff", Document issued on Jul. 27, 2019, <https://www.fda.gov/media/72693/download>, 27 pages.

Choi, Jiyeon, et al. "Effect of solvent on drug release and a spray-coated matrix of a sirolimus-eluting stent coated with poly (lactic-co-glycolic acid)." Langmuir 30.33, Publication dated Aug. 4, 2014, pp. 10098-10106.

(56) References Cited

OTHER PUBLICATIONS

Medinol Ingenuity for Life, "X-Suit NIR / Bilinary Metallic Stent", Copyright 2017, <https://www.medinol.com/us/products/x-suit-nir/>, 5 pages.
Balakrishnan, Brinda, et al. "Intravascular drug release kinetics dictate arterial drug deposition, retention, and distribution." Journal of Controlled Release 123.2, Nov. 6, 2007, pp. 100-108.
Minami, Yoshiyasu et al., "Endothelial dysfunction following drug-eluting stent implantation: a systematic review of the literature. International Journal of Cardiology", 165(2), May 10, 2013, pp. 222-228.
Chinese Search Report for Application No. 201910361865.3, dated Apr. 1, 2021, 11 pages.
Schmidt et al., "Trackability, Crossability, and Pushability of Coronary Stent Systems—An Experimental Approach," Biomed Techn 47 (2002), Erg. 1, S. 124-126.
Schmidt et al., "In vitro measurement of quality parameters of stent-catheter systems," Biomed Techn 50 (SI):1505-1506 (2005).
Szabadits et al., "Flexibility and trackability of laser cut coronary stent systems," Acta of Bioengineering and Biomechanics 11 (3 ): 11-18 (2009).
PCT/US10/28195 Search Report and Written Opinion dated Jan. 21, 2011.
PCT/US10/31470 Search Report and Written Opinion dated Jan. 28, 2011.
PCT/US10/29494 Search Report and Written Opinion dated Feb. 7, 2011.
PCT/US11/22623 Search Report and Written Opinion dated Mar. 28, 2011.
Di Mario, C. et al., "Drug-Eluting Bioabsorbable Magnesium Stent," J. Interventional Cardiology 16(6):391-395 (2004).
PCT/US09/41045 International Search Report dated Aug. 11, 2009.
PCT/US08/64732 International Search Report dated Sep. 4, 2008.
PCT/US08/60671 International Search Report dated Sep. 5, 2008.
Ong and Serruys, "Technology Insight: an overview of research in drug-eluting stents," Nat. Clin. Parct. Cardiovas. Med. 2(12):647 (2005).
Cohen et al., "Sintering Technique for the Preparation of Polymer Matrices for the Controlled Release of Macromolecules", Journal of Pharmaceutical Sciences, vol. 73, No. 8, 1984, p. 1034-1037.
Colombo et al. "Selection of Coronary Stents," Journal of the American College of Cardiology, vol. 40, No. 6, 2002, p. 1021-1033.
CRC Handbook of chemistry and physics. 71st ed. David R. Lide, Editor-in-Chief. Boca Raton, Fl, CRC Press; 1990; 6-140.
Matsumoto, D, et al. Neointimal Coverage of Sirolimus-Eluting Stents at 6-month Follow-up: Evaluated by Optical Coherence Tomography, European Heart Journal, Nov. 29, 2006; 28:961-967.
PCT/US06/27321 International Preliminary Report on Patentability dated Jan. 16, 2008.
PCT/US06/27322 International Preliminary Report on Patentability dated Jan. 16, 2008.
PCT/US07/10227 International Preliminary Report on Patentability dated Oct. 28, 2008.
PCT/US07/80213 International Preliminary Report on Patentability dated Apr. 7, 2009.
PCT/US08/11852 International Preliminary Report on Patentability dated Apr. 20, 2010.
PCT/US08/50536 International Preliminary Report on Patentability dated Jul. 14, 2009.
PCT/US08/60671 International Preliminary Report on Patentability dated Oct. 20, 2009.
PCT/US08/64732 International Preliminary Report on Patentability dated Dec. 1, 2009.
PCT/US09/41045 International Preliminary Report on Patentability dated Oct. 19, 2010.
PCT/US09/69603 International Preliminary Report on Patentability dated Jun. 29, 2011.
PCT/US10/28265 International Report on Patentability dated Sep. 27, 2011.
PCT/US10/29494 International Preliminary Report on Patentability dated Oct. 4, 2011.
PCT/US10/31470 International Preliminary Report on Patentability dated Oct. 18, 2011.
PCT/US11/32371 International Report on Patentability dated Oct. 16, 2012.
PCT/US11/51092 International Search Report dated Mar. 27, 2012.
PCT/US11/51092 Written Opinion dated Mar. 27, 2012.
PCT/US11/22623 International Preliminary Report on Patentability dated Aug. 7, 2012.
PCT/US11/29667 International Search Report and Written Opinion dated Jun. 1, 2011.
CT/US12/33367 International Preliminary Report on Patentability dated Oct. 15, 2013.
PCT/US13/41466 International Search Report and Written Opinion dated Oct. 17, 2013.
PCT/US13/42093 International Search Report and Written Opinion dated Oct. 24, 2013.
PCT/US12/60896 International Search Report and Written Opinion dated Dec. 28, 2012.
PCT/US13/65777 International Search Report and Written Opinion dated Jan. 29, 2014.
Putkisto, K. et al. "Polymer Coating of Paper Using Dry Surface Treatment—Coating Structure and Performance", ePlace newsletter, 2004 (Apr. 12), vol. 1, No. 8, pp. 1-20.
Sahajanand Medical Technologies, Pledged to Save Millions, Supralimus Core Sirolimus Eluting Coronary Stent: Sahajanand, Jul. 6, 2008.
Zilberman et al., Drug-Eluting bioresorbable steuts for various applications, Annu Rev Biomed Eng,., 2006;8: 158-180.
Chlopek et al., "The influence of carbon fibres on the resorption time and mechanical properties of the lactide glycolide copolymer", J. Biomater. Sci. Polymer Edn. vol. 18, No. 11, pp. 1355-1368 (2007).
Koh et al., "A novel nanostructured poly(lactic-co-glycolic-acid) multi-walled carbon nanotube composite for blood-contacting application. Thrombogenicity studies", Acta Biomaterials 5 (2009): 3411-3422.
Latella et al., "Nanoindentation hardness. Young's modulus, and creep behavior of organic-inorganic silica-based sol-gel thin films on copper," J Mater Res 23(9): 2357-2365 (2008).
PCT/US06/24221 International Search Report mailed with a completion date of Jan. 3, 2007.
Schmidt et al., "A Comparison of the Mechanical Performance Characteristics of Seven Drug-Eluting Stent Systems," Catheterization and Cardiovascular Interventions 73:350-360 (2009).
Shekunov et al., "Crystallization Processes in Pharmaceutical Technology and Drup Delivery Design", Journal of Crystal Growth 211 (2000), pp. 122-136.
Wu et al., "Study on the preparation and characterization of biodegradable polylactide/multi-walled carbon nanotubes nanocomposites", Polymer 48 (2007) 4449-4458.
PCT/US10/28253 Search Report and Written Opinion dated Dec. 6, 2010.
PCT/US10/28195 International Preliminary Report on Patentability dated Sep. 27, 2011.
PCT/US11/51092 International Preliminary Report on Patentability dated Mar. 12, 2013.
PCT/US11/67921 International Preliminary Report on Patentability dated Jul. 2, 2013.
Akoh et al., "One-Stage Synthesis of Raffinose Fatty Acid Polyesters." Journal Food Science (1987) 52:1570.
Albert et al., "Antibiotics tor preventing recurrent urinary tract infection in nonpregnant women,"Cochrane Database System Rev. 3, CD001209 (2004).
Au et al., "Methods to improve efficacy of intravesical mitomycin C: Results of a randomized phase III trial," Journal of the National Cancer Institute, 93 (8 ), 597-604 (2001).
Balss et al., "Quantitative spatial distribution of sirolumus and polymers in drugeluting stents using confocal Raman microscopy," J. of Biomedical Materials Research Part A, 258-270 (2007).
Belu el al., "Three-Dimensional Compositional Analysis of Drug Eluting Stent Coatings Using Cluster Secondary loan Mass Spectrometry," Anal. Chem. 80:624-632 (2008).

(56) References Cited

OTHER PUBLICATIONS

Belu, et al., "Chemical imaging of drug eluting coatings: Combining surface analysis and confocal Rama microscopy" J. Controlled Release 126: 111-121 (2008).
Boneff, "Topical Treatment of Chronic Prostatitis and Premature Ejaculation," International Urology and Nephrology 4(2):183-186 (1971).
Bookbinder et al., "A recombinant human enzyme for enhanced interstitial transport of therapeutics," Journal of Controlled Release 114:230-241 (2006).
Borchert et al., "Prevention and treatment of urinary tract infection with probiotics: Review and research perspective," Indian Journal Urol. 24(2): 139-144 (2008).
Brunstein et al., "Histamine, a vasoactive agent with vascular disrupting potential, improves tumour response by enhancing local drug delivery," British Journal of Cancer 95:1663-1669 (2006).
Bugay et al., "Raman Analysis of Pharmaceuticals," in "Applications of Vibrational Spectroscopy in Pharmaceutical Research and Development," Edited by Pivonka, D.E., Chalmers, J.M., Griffiths, P.R. (2007) Wiley and Sons.
Channon et al., "Nitric Oxide Synthase in Atherosclerosis and Vascular Injury: Insights from Experimental Gene Therapy," Arteriosclerosis, Thrombosis and Vascular Biology, 20(8):1873-1881 (2000).
Clair and Burks, "Thermoplastic/Melt-Processable Polyimides," NASA Conf. Pub. #2334 (1984), pp. 337-355.
Cyrus et al., "Intramural delivery of rapamycin with alphavbeta3-targeted paramagnetic nanoparticles inhibits stenosis after balloon injury," Arterioscler Thromb Vasc Biol 2008; 28:820-826. Abstracting 2004003077; Jan. 8, 2004; 3 pages.
Di Stasi et al., "Percutaneous sequential bacillus Calmette-Guerin and mitomycin C for panurothelial carcinomatosis," Can. J. Urol. 12(6):2895-2898 (2005).
Domb and Langer, "Polyanhydrides. I. Preparation of High Molecular Weight Polyanhydrides. "J. Polym Sci. 25:3373-3386 (1987).
Dzik-Jurasz, "Molecular imaging in vivo: an introduction," The British Journal of Radiology, 76:S98-S109 (2003).
Electrostatic Process, Wiley Encyclopedia of Electrical and Electronics Engineering, John Wiley & Sons, Inc. 1999; 7:15-39.
Eltze et al., "Imidazoquinolinon, imidazopyridine, and isoquinolindione derivatives as novel and potent inhibitors ofthe poly (ADP-ribose) polymerase (PARP): a comparison with standard PARP inhibitors," Mol. Pharmacal 74(6):1587-1598 (2008).
Ettmayer et al. Lessons learned from marketed and investigational prodrugs. J Med Chem. May 6, 2004;47 (10):2393-404.
Fleischmann et al., "High Expression of Gastrin-Releasing Peptide Receptors in the Vascular bed of Urinary Tract Cancers: Promising Candidates for Vascular Targeting Applications." Jun. 2009, Endocr. Relat. Cancer 16(2):623-33.
Fujiwara et al., "Insulin-like growth factor 1 treatment via hydrogels rescues cochlear hair cells from ischemic injury," Oct. 29, 2008, NeuroReport 19(16):1585-1588.
Green et al., "Simple conjugated polymer nanoparticles as biological labels," Proc Roy Soc A. published online Jun. 24, 2009 doi:10.1098/rspa.2009.0181.
Griebenow et al., "On Protein Denaturation in Aqueous-Organic Mixtures but not in Pure Organic Solvents," J. Am Chem Soc., vol. 118. No. 47, 11695-11700 (1996).
Hamilos et al., "Ditlerential etlects ofDmg-Eluting Stents on Local Endothelium-Dependent Coronary Vasomotion." JACC vol. 51, No. 22,2008, Endothelium and DES Jun. 3, 2008:2123-9.
Hartmann et al., "Tubo-ovarian abscess in virginal adolescents: exposure or the underlying etiology," J. Pediatr Adolesc Gynecol, 22(3):313-16 (2009).
Hasegawa et al., "Nylong 6/Na-montmorillonite nanocomposites prepared by compounding Nylon 6 with Na-montmorillonite slurry," Polymer 44 (2003) 2933-2937.

Hinds, WC. Aerosol Technology, Properties, Behavior and Measurement of Airbome Particles, Department of Environmental Health Sciences, Harvard University School of Public Health, Boston, Massachusetts. 1982; 283-314.
Hladik et al., "Can a topical microbicide prevent rectal HIV transmission?" PLoS Med. 5(8):e167 (2008).
Iconomidou et al., "Secondary Structure of Chorion Proteins ofthe Teleosatan Fish Dentex dentex by ATR FR-IR and FT-Raman Spectroscopy," J. of Structural Biology, 132, 112-122(2000).
Jackson et al., "Characterization of perivascular poly(lactic-co-glycolic acid) films containing paclitaxel" Int. J. ofPhannaceutics, 283:97-109 (2004), incorporated in its entirety herein by reference.
Jensen et al., Neointimal hyperplasia after sirollmus-eluting and paclitaxel-eluting stend implantation in diabetic patients: the randomized diabetes and dmg eluting stent (DiabeDES) intravascular ultrasound trial. European heartjoumal (29), pp. 2733-2741. Oct. 2, 2008. Retrieved from the Internet. Retrieved on [ Jul. 17, 2012]. URL: <http :/ /eurheartj .oxfordjournals.org/ content/2 9/22/2 73 3. full. pdf> entire document.
Jewell, et al., "Release ofPlasmid DNA from Intravascular Stents Coated with Ultrathin Multilayered Polyelectrolyte Films" Biomacromolecules. 7: 2483-2491 (2006).
Johns, H.E, J.R.Cunningham, Thomas, Charles C., Publisher, "The Physics of Radiology, "1983, Springfield, IL, pp. 133-143.
Joner et al. "Site-specific targeting of nanoparticle prednisolone reduces in-stent restenosis in a rabbit model of established atheroma," Arterioscler Thromb Vase Biol.2008 ;28: 1960-1966.
Mei et al., "Local Delivery of Modified Paclitaxel-Loaded Poly(£-caprolactone)/Pluronic F68 Nanoparticles for Long-Term Inhibition of Hyperplasia," Journal of Pharmaceutical Sciences, vol. 98, No. 6, Jun. 2009.
Jovanovic et al. "Stabilization of Proteins in Dry Powder Formulations Using Supercritical Fluid Technology," Pharm. Res. 2004; 21(11).
Kazemi et al., "The effect ofbetamethasone gel in reducing sore throat, cough, and hoarseness after laryngo-tracheal intubation," Middle East J. Anesthesiol. 19(1):197-204 (2007).
Kehinde et al., "Bacteriology of urinary tract infection associated with indwelling J ureteral stents," J. Endourol. 18 (9):891-896 (2004).
Kelly et al., "Double-balloon trapping technique for embolization of a large widenecked superior cerebellar artery aneurysm: case report," Neurosurgery 63(4 Suppl 2):291-292 (2008).
Khan et al., Cyclic Acetals of 4,1',6'-Trichloro-4, 1',6',-Trideoxy-Trideoxy-galacto-Sucrose and their Conversion into Methyl Ether Derivatives. Carb. ResCarb. Res. (1990) 198:275-283.
Khan et al., "Chemistry and the new uses or Sucrose: How Important?" Pur and Appl. Chem (1984) 56:833-844.
Khan et al., "Enzymic Regioselective Hydrolysis of Peracctylated Reducing Disaccharides, Specifically at the Anomeric Centre: Intermediates for the Synthesis of Oligosaccharides." Tetrahedron Letters (1933) 34:7767.
Khayankarn et al., "Adhesion and Permeability of Polyimide-Clay Nanocomposite Films for Protective Coatings," Journal of Applied Polymer Science, vol. 89,2875-2881 (2003).
Kurt et al., "Tandem oral, rectal and nasal administrations of Ankaferd Blood Stopper to control profuse bleeding leading to hemodynamic instability," Am J. Emerg. Med. 27(5):631, e1-2 (2009).
Labhasetwar et al., "Arterial uptake of biodegradable nanoparticles: effect of surface modifications," Journal of Pharmaceutical Sciences, vol. 87, No. 10, Oct. 1998; 1229-1234.
Lamm et al., "Bladder Cancer: Current Optimal Intravesical Treatment: Pharmacologic Treatment," Urologic Nursing 25 (5):323-6, 331-2 (Oct. 26, 2005).
Lawrance et al., "Rectal tacrolimus in the treatment of resistant ulcerative proctitis," Aliment. Pharmacol Ther. 28 (10):1214-20 (2008).
Lee et al., "Novel therapy for hearing loss: delivery of insulin-like growth factor 1 to the cochlea using gelatin hydrogel," Otol. Neurotol. 28(7):976-81 (2007).

(56) References Cited

OTHER PUBLICATIONS

Lehmann et al., "Drug treatment of nonviral sexually transmitted diseases: specific issues in adolescents," Paediatr Drugs 3(7):481-494 (2001).
Mahoney et al., "Three-Dimensional Compositional Analysis ofDrug Eluting Stent Coatings Using Cluster Secondary on mass Spectrometry," Anal. Chem. , 80, 624-632 (2008).
Mehik et al., "Alfuzosin treatment for chronic prostatitis/chronic pelvic pain syndrome: a prospecitve, randomized, double-blind, placebo-controlled, pilot study," Urology 62(3):425-429 (2003).
Melonakos et al., Treatment of low-grade bulbar transitional cell carcinoma with urethral instillation ormitmnycin C, Oct. 28, 2008, Adv. Urol., 173694 Epub.
Merrett et al., "Interaction of corneal cells with transforming growth factor beta2-modified poly dimethyl siloxane surfaces," Journal of Biomedical Materials Research, Part A, vol. 67A, No. 3, pp. 981-993 (2003).
Middleton and Tipton, Synthetic biodegradable polymers as orthopedic devises. Biomaterials 2000; 21:2335-46.
Minchin, "Nanomedicine: sizing up targets with nanoparticles," Nature Nanotechnology, vol. 33, Jan. 2008, 12-13.
Minoque et al., "Laryngotracheal topicalization with lidocaine before intubation decreases the incidence of coughing on emergence from general anesthesia," Anesth. Analg. 99(4):1253-1257 (2004).
Mishima et al. "Microencapsulation of Proteins by Rapid Expansion orSupercritical Solution with a Nonsolvent," AIChE J. 2000;46(4):857-65.
Mocco et al., "Pharos neurovascular intracranail stent: Elective use for a symptomatic stenosis refractory to medical therapy," Catheter Cardiovasc. Interv. (epub) (Mar. 2009).
Mollen et al., "Prevalence oftubo-ovarian abcess in adolescents diagnosed with pelvice inflammatory disease in a pediatric emergency department," Pediatr. Emerg. Care, 22(9): 621-625 (2006).
Muhlen et al., "Magnetic Resonance Imaging Contrast Agent Targeted Toward Activated Platelets Allows in Vivo Detection of Thrombosis and Monitoring of Thrombolysis Circulation," 118:258-267 (2008).
Murphy et al., "Chronic prostatitis: management strategies," Drugs 69(1): 71-84 (2009).
O'Neil et al., "Extracellular matrix binding mixed micelles for drug delivery applications," Journal of Controlled Release 137 (2009) 146-151.
O'Donnell et al., "Salvage intravesical therapy with interferon-alpha 2b plus low dose bacillus Calmette-Guerin is effective in patients with superficial bladder cancer in whom bacillus calmette-guerin alone previously failed," Journ. Urology, 166(4): 1300-1304 (2001).
Olbert et al., "In vitro and in vivo effects of CpG-Oligodeoxynucleotides (CpG-ODN) on murine transitional cell carcinoma and on the native murine urinary bladder wall," Anticancer Res. 29(6):2067-2076 (2009).
PCT/US12/46545 International Search Report dated Nov. 20, 2012.
PCT/US12/40040 International Search Report dated Sep. 7, 2012.
Perry et al., Chemical Engineer's Handbook, 5th Edition, McGraw-Hill, New York, 1973; 20-106.
Torchlin, "Micellar Nanocarriers: Pharmaecutial Perspectives," Pharmaceutical Research, vol. 24, No. 1, Jan. 2007.
Plas et al., "Tubers and tumors: rapamycin therapy for benign and malignant tumors", Curr Opin Cell Bio 21:230-236, (2009).
Poling et al., The Properties of Gases and Liquids. McGraw-Hill. 2001; 9:1-9.97.
Pontari, "Inflammation and anti-inflammatory therapy in chronic prostatits," Urology 60(6Suppl):29-33 (2002).
Ranganath et al., "Hydrogel matrix entrapping PLGA-paclitaxel microspheres: drug delivery with near zero-order release and implantability advantages for malignant brain tumour chemotherapy," Pharm Res (Epub) Jun. 20, 2009).
Ranade et al., "Physical characterization of controlled release of paclitaxel from the TAXUS Express2 drug-eluting stent," J. Biomed Mater. Res. 71 (4):625-634 (2004).
Reddy et al., "Inhibition of apoptosis through localized delivery of rapamycin-loaded nanoparticles prevented heointimal hyperplasia and reendothelialized injured artery," Circ Cardiovasc Interv 2008;1 ;209-216.
Ristikankare et al., "Sedation, topical pharnygeal anesthesia and cardiorespiratory safety during gastroscopy," J. Clin Gastorenterol. 40(1 ):899-905 (2006).
Salo et al., "Biofilm formation by *Escherichia coli* isolated from patients with urinary tract infections," Clin Nephrol. 71 (5):501-507 (2009).
Saxena et al., "Haemodialysis catheter-related bloodstream infections: current treatment options and strategies for prevention," Swiss Med Wkly 135:127-138 (2005).
Schetsky, L. McDonald, "Shape Memory Alloys", Encyclopedia of Chemical Technology (3d Ed), John Wiley & Sons 1982, vol. 20 pp. 726-736.
Scheufler et al., "Crystal Structure of Human Bone Morphogenetic Protein-2 at 2.7 Angstrom resolution," Journal of Molecular Biology, vol. 287, Issue 1, Mar. 1999, pp. 103-115.
Sen et al., "Topical heparin: A promising agent for the prevention of tracheal stenosis in airway surgery," J. Surg. Res (Epub ahead of print) Feb. 21, 2009.
Simpson et al., "Hyaluronan and hyaluronidase in genitourinary tumors."Front Biosci. 13:5664-5680.
Smith et al., "Mitomycin C and the endoscopic treatment of laryngotracheal stenosis: Are two applications better than one?" Laryngoscope 119(2):272-283 (2009).
Sumathi et al., "Controlled comparison between betamethasone gel and lidocaine jelly applied over tracheal tube to reduce postoperative sore throat, cough, and hoarseness of voice," Br. J. Anaesth. 100(2):215-218 (2008).
Testa, B., "Prodrug research: futile or fertile?", Biochem. Pharmacal. Dec. 1, 2004;68(11):2097-2106.
Thalmann et al., "Long-term experience with bacillus Calmette-Guerin therapy of upper urinary tract transitional cell carcinoma in patients not eligible for surgery," J Urol. 168(4 Pt 1):1381-1385 (2002).
Merriam-Webster Online Dictionary, obtained online at: <http://www.merriamwebster.com/dictionay/derivative>, downloaded Jan. 23, 2013.
Unger et al., "Poly(ethylene carbonate): A thermoelastic and biodegradable biomaterial for drug eluting stent coatings?" Journal to Controlled Release, vol. 117, Issue 3, 312-321 (2007).
Verma et al., "Effect of surface properties on nanoparticle-cell interactions," Small 2010,6,No. 1, 12-21.
Wagenlehner et al., "A pollen extract (Cemilton) in patients with inflammatory chronic prostatitis/chronic pelvic pain syndrome: a multicentre, randomized, prospective, double-blind, placebo-controlled phase 3 study," Eur Urol 9 (Epub) (Jun. 3, 2009).
Wang, X.; Venkatraman, S.S.; Boey, F.Y.C .; Loo, J.S.C.; Tan, L.P. "Controlled release of sirolimus from a multilayered PLGA stent matrix" Biomaterials 2006, 27, 5588-5595.
Wang et al., "Treatment with melagatran alone or in combination with thrombolytic therapy reduced ischemic brain Injury," Exp. Neuro. 213(1):171-175 (2008).
Warner et al., "Mitomycin C and airway surgery: how well does it work?" Ontolaryngol Head Neck Surg. 138 (6):700-709 (2008).
Wermuth, CG, "Similarity in drugs: reflections on analogue design", Drug Discov Today. Apr. 2006. 11(7-8):348-54.
Witjes et al., "Intravesical pharmacotherapy for non-muscle-invasive bladder cancer: a critical analysis of currently available drugs, treatment schedules, and long-term results," Eur. Urol. 53(1):45-52.
Xu et al., "Biodegradation of poly(L-lactide-co-glycolide) tube stents in bile", Polymer Degradation and Stability. 93:811-817 (2008).
Xue et al., "Spray-as-you-go airway topical anesthesia in patients with a difficult airway: a randomized, double-blind comparison of2% and 4% lidocaine," Anesth. blind comparison of 2% and 4% lidocaine, Anesth. Analg. 108(2): 536-543 (2009).
Yepes et al., "Tissue-type plasminogen activator in the ischemic brain: more than a thrombolytic," Trends Neurosci. 32(1):48-55 (2009).

(56) References Cited

OTHER PUBLICATIONS

Yousuf et al., "Resveratrol exerts its neuroprotective effect by modulating mitochondrial dysfunction and associated cell death during cerebral ischemia", Brain Res. 1250:242-253 (2009).
Zhou, S .; Deng, X .; Li, X .; Jia, W .; Liu, L. "Synthesis and Characterization of Biodegradable Low Molecular Weight Aliphatic Polyesters and Their Use in Protein-Delivery Systems" J. Appl. Polym. Sci. 2004, 91, 1848-1856.
PCT/US11/44263 International Preliminary Report on Patentability dated Jan. 22, 2013.
PCT/US07/82775 International Preliminary Report on Patentablity dated May 5, 2009.
PCT/US09/69603 International Search Report dated Nov. 5, 2010.
PCT/US09/50883 International Preliminary Report on Patentability dated Jan. 18, 2011.
PCT/US10/28253 International Preliminary Report on Patentability dated Sep. 27, 2011.
PCT/US12/33367 International Search Report dated Aug. 1, 2012.
PCT/US10/42355 International Preliminary Report on Patentability dated Jan. 17, 2012.
PCT/US11/67921 Search Report and Written Opinion dated Jun. 22, 2012.
Domingo, C., et al., "Precipication of ultrafine organic crystals from the rapid expansion of supercritical solutions ove a capillary and a frit nozzle", J. Supercritical Fluids 10:39-55 (1997).
McAlpine, J.B et al., "Revised NMR Assignments for Rapamycine," J. Antibiotics 44:688-690 (1991).
PCT/US09/50883 International Search Report dated Nov. 17, 2009.
Schreiber, S.L. et al., "Atomic Structure of the Rapamycin Human Immunophilin FKBP-12 Complex," J. Am. Chern. Soc. 113:7433-7435 (1991).
Serruys, Patrick et al., Comparison of Coronary-Artery Bypass Surgery and Stenting for the Treatment of Multivessel Disease, N. Engl. J. Med., 2001, vol. 344, No. 15, pp. 1117-1124.
Schmidt et al., "New aspects of in vitro testing of arterial stents based on the new European standard," EN 14299, [online] (2009), [retrieved on Mar. 10, 2001] <http://www.libOev .de/pl/pdf/EN14 299. pdf> (2009).
PCT/US10/42355 Search Report dated Sep. 2, 2010.
PCT/US10/28265 Search Report and Written Opinion dated Dec. 13, 2010.
PCT/US06/24221 International Preliminary Report on Patentability dated Dec. 24, 2007.
Abreu Filho et al., "Influence of metal alloy and the profile of coronary stents in patients with multivessel coronary disease," CLINICS 2011 ;66(6):985-989.
Cadieux et al., "Use of triclosan-eluting ureteral stents in patients with long-term stents," J. Endourol (Epub) (Jun. 19, 2009).
Chen et al. Immobilization of heparin on a silicone surface through a heterobifunctional PEG spacer. Biomaterials. Dec. 2005;26(35):7418-24.

Fibbi et al., "Chronic inflammation in the pathogenesis of benign prostatic hyperplasia," Int J Androl. Jun. 1, 2010;33 (3):475-88.
Froehlich et al., "Conscious sedation for gastroscopy: patient tolerance and cardiorespiratory parameters," Gastroenterology 108(3):697-704 (1995).
Fulton et al. Thin Fluoropolymer films and nanoparticle coatings from the rapid expansion of supercritical carbon dioxide solutions with electrostatic collection, Polymer Communication. 2003; 2627-3632.
Moroni et al., "Post-ischemic brain damage:targeting PARP-1 within the ischemic neurovaschular units as a realistic avenue to stroke treatment," FEBS J. 276(1 ):36-45 (2009).
PCT/US06/27321 International Search Report dated Oct. 16, 2007.
PCT/US06/27322 International Search Report dated Apr. 25, 2007.
PCT/US07/10227 International Search Report dated Aug. 8, 2008.
PCT/US07/80213 International Search Report dated Apr. 16, 2008.
PCT/US07/82275 International Search Report dated Apr. 18, 2008.
PCT/US08/11852 International Search Report dated Dec. 19, 2008.
PCT/US08/50536 International Search Report dated Jun. 2, 2008.
Pontari, "Chronic prostatitis/chronic pelvic pain syndrome in elderly men: toward better understanding and treatment," Drugs Aging 20(15): 1111-1115 (2003).
PCT/US11/32371 International Search Report dated Jul. 7, 2011.
PCT/US11/44263 International Search Report and Written Opinion dated Feb. 9, 2012.
PCT/US14/25017 International Search Report and Written Opinion dated Jul. 7, 2014.
Han, et al., "Studies of a Novel Human Thrombomodulin Immobilized Substrate: Surface Characterization and Anticoagulation Activity Evaluation." J. Biomater. Sci. Polymer Edn, 2001, 12 (10), 1075-1089.
PCT/US14/38117 International Search Report and Written Opinion dated Oct. 7, 2014.
Greco et al., Polymer Melting and Polymer Powder Sintering by Thermal Analysis, (Journal of Thermal Analysis and Calorimetry, vol. 72 (2003) 1167-1174.).
PCT/US13/42093 International Preliminary Report on Patentability dated Nov. 25, 2014.
Finn et al. Differential Response of Delayed Healing ... Circulation vol. 112 (2005) 270-8.
Wang et al. "Synthesis, characterization, biodegradation, and drug delivery application of biodegradable lactic/glycolic acid polymers: I. Synthesis and characterization" J. Biomater. Sci. Polymer Edn. 11(3):301-318 (2000).
PCT/US13/41466 International Preliminary Report on Patentability dated Nov. 18, 2014.
Ju, et al., Drug Release from Hydrophilic Matrices. 1. New Scaling Laws for Predicting Polymer and Drug Release Based on the Polymer Disentanglement Concentration and the Diffusion Layer, J. Pharm. Sci. vol. 84, No. 12, 1455-1463, Dec. 1995.
PCT/US12/50408 International Search Report dated Oct. 16, 2012.
European International Search Report of PCT/EP01/05736 dated Oct. 24, 2001.
PCT/EP01/05736 International Preliminary Examination Report dated Jan. 14, 2002.

 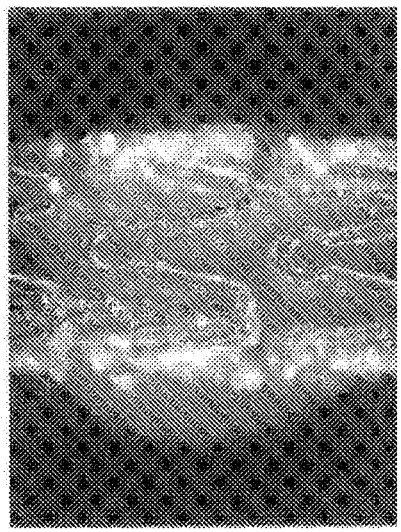
Drug-Polymer coated coronary stent (a) immediately after deposition, (b) after annealing in a dense carbon dioxide environment at 40°C
FIG. 3

Optical Microscopy of Rapamycin/PEVA/PBMA Coated Stents
(a) Powder coated before sintering
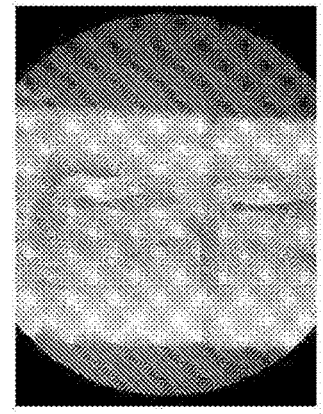
Outside Surface
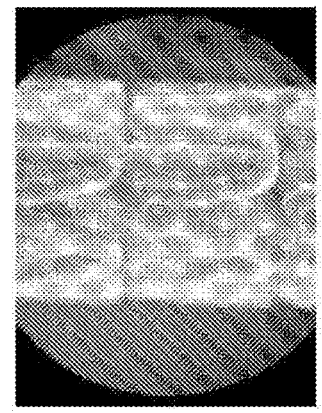
Edge Surface
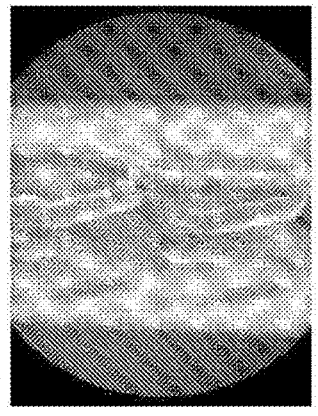
Inside Surface
(b) Powder coated after sintering
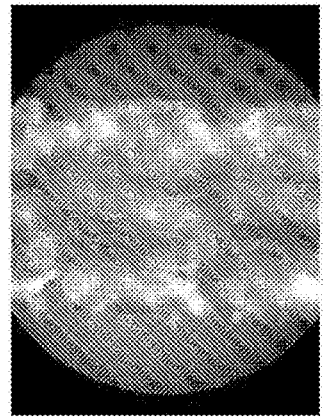
Outside Surface
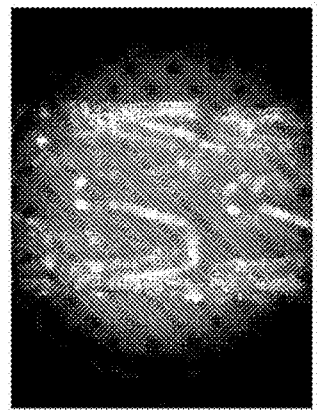
Edge Surface
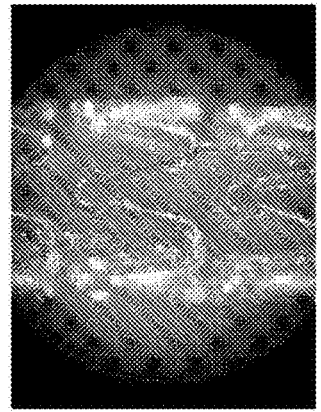
Inside Surface
FIG. 4

Optical Microscopy of Rapamycin/PEVA/PBMA Coated Stents
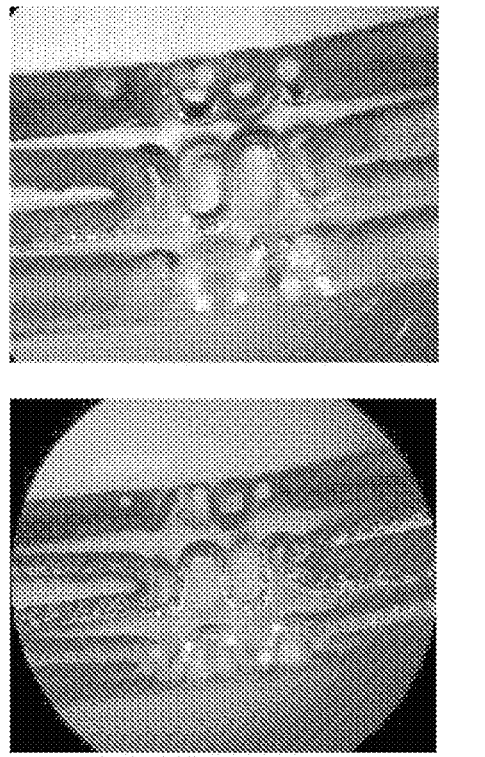
(b) Powder coated after sintering
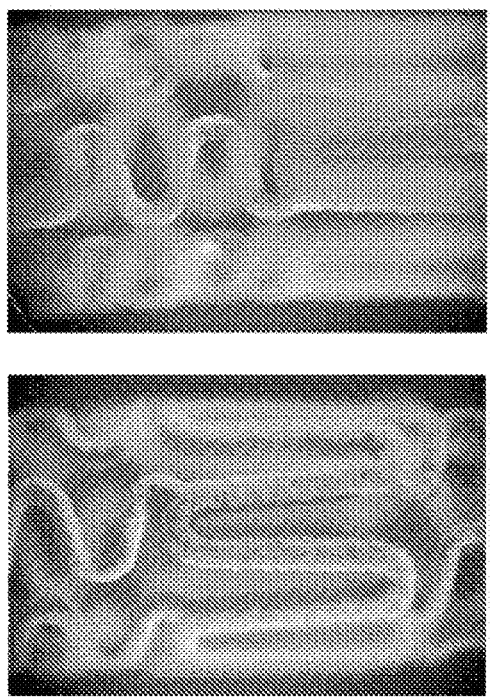
(a) Powder coated before sintering
FIG. 5

Optical Microscopy of Rapamycin/PEVA/PBMA Coated Stents After Sintering at 100X magnification Scanning Electron Microscope Images of Rapamycin/PEVA/PBMA Coated Stent (FIB Cross-sections)

(a) x7000 magnification   (b) x20000 magnification

Four cross-sectional thicknesses measured:
(1) 10.355μM; (2) 10.412μM; (3) 10.043μM; (4) 10.157μM UV-Vis & FT-IR Quantification of Rapamycin, PEVA and PBMA Coating Components; mean concentrations (3 stents each); 6 cell by 8mm parylene coated (b) PEVA Quantification Using FT-IR Standard Method (c) PBMA Quantification
Using FT-IR Standard Method Development of Novel Drug Eluting Coating for a Dual Drug Eluting Stent

Target Product

Multi-drug Delivery Platform

- Strong, resilient & flexible
- Anti-restenosis: 'limus or taxol
- Anti-thrombosis: heparin or analog
- Known and well characterized bioabsorbable polymers
- Simple automated high-volume manufacturing

Clinical Attributes

- Minimize potential for thrombosis
  - Eliminate thrombogenic polymers
  - Eliminate potential for residual drug(s) that could inhibit healing
- Optimized delivery of multiple drug therapies
  - Early-stage (restenosis)
  - Late-stage (thrombosis)
- Adherent coating so as to be able to access torturous lesions without the risk of the coating being compromised

FIG. 19

COATINGS CONTAINING MULTIPLE DRUGS

CROSS-REFERENCE

The present application is a continuation application of U.S. patent application Ser. No. 16/223,552, filed on Dec. 18, 2018, which is a continuation of U.S. patent application Ser. No. 15/591,287, filed on May 10, 2017, which is a continuation of U.S. patent application Ser. No. 14/969,884, filed on Dec. 15, 2015 (now U.S. Pat. No. 9,737,645), which is a continuation of U.S. patent application Ser. No. 14/473,741, filed on Aug. 29, 2014, now U.S. Pat. No. 9,415,142, the disclosures of which are hereby incorporated by reference, which claims the benefit of U.S. application Ser. No. 12/298,459, filed Mar. 16, 2009, now U.S. Pat. No. 8,852,625, which was filed pursuant to 35 U.S.C. § 371 as a United States National Phase Application of International Application No. PCT/US2007/010227, filed Apr. 26, 2007, which claims the benefit of U.S. Provisional Application Nos. 60/912,394 filed Apr. 17, 2007; 60/745,731 filed Apr. 26, 2006; and 60/745,733 filed Apr. 26, 2006, all of which are incorporated herein by reference in their entirety.

BACKGROUND OF THE INVENTION

The present invention relates to methods for depositing a coating comprising a polymer and a pharmaceutical or biological agent in powder form onto a substrate.

It is often beneficial to provide coatings onto substrates, such that the surfaces of such substrates have desired properties or effects.

For example, it is useful to coat biomedical implants to provide for the localized delivery of pharmaceutical or biological agents to target specific locations within the body, for therapeutic or prophylactic benefit. One area of particular interest is that of drug eluting stents (DES) that has recently been reviewed by Ong and Serruys in Nat. Clin. Pract. Cardiovasc. Med., (Dec 2005), Vol 2, No 12, 647. Typically such pharmaceutical or biological agents are co-deposited with a polymer. Such localized delivery of these agents avoids the problems of systemic administration, which may be accompanied by unwanted effects on other parts of the body, or because administration to the afflicted body part requires a high concentration of pharmaceutical or biological agent that may not be achievable by systemic administration. The coating may provide for controlled release, including long-term or sustained release, of a pharmaceutical or biological agent. Additionally, biomedical implants may be coated with materials to provide beneficial surface properties, such as enhanced biocompatibility or lubriciousness.

Conventionally, coatings have been applied by processes such as dipping, spraying, vapor deposition, plasma polymerization, and electro-deposition. Although these processes have been used to produce satisfactory coatings, there are drawbacks associated therewith. For example it is often difficult to achieve coatings of uniform thicknesses and prevent the occurrence of defects (e.g. bare spots). Also, in many processes, multiple coating steps are frequently necessary, usually requiring drying between or after the coating steps.

Another disadvantage of most conventional methods is that many pharmaceutical or biological agents, once deposited onto a substrate, suffer from poor bioavailability, reduced shelf life, low in vivo stability or uncontrollable elution rates, often attributable to poor control of the morphology and/or secondary structure of the agent. Pharmaceutical agents present significant morphology control challenges using existing spray coating techniques, which conventionally involve a solution containing the pharmaceutical agents being spayed onto a substrate. As the solvent evaporates the agents are typically left in an amorphous state. Lack of or low degree of crystallinity of the spray coated agent can lead to decreased shelf life and too rapid drug elution. Biological agents typically rely, at least in part, on their secondary, tertiary and/or quaternary structures for their activity. While the use of conventional solvent-based spray coating techniques may successfully result in the deposition of a biological agent upon a substrate, it will often result in the loss of at least some of the secondary, tertiary and/or quaternary structure of the agent and therefore a corresponding loss in activity. For example, many proteins lose activity when formulated in carrier matrices as a result of the processing methods.

Conventional solvent-based spray coating processes are also hampered by inefficiencies related to collection of the coating constituents onto the substrate and the consistency of the final coating. As the size of the substrate decreases, and as the mechanical complexity increases, it grows increasingly difficult to uniformly coat all surfaces of a substrate.

What is needed is a cost-effective method for depositing inert polymers and pharmaceutical or biological agents onto a substrate, where the collection process is efficient, the coating produced is conformal, substantially defect-free and uniform, the composition of the coating can be regulated and the morphology and/or secondary structure of the pharmaceutical or biological agents can be controlled. The method would thus permit structural and morphological preservation of the agents deposited during the coating process.

SUMMARY OF THE INVENTION

A first aspect of the invention provides methods for depositing a coating comprising a polymer and pharmaceutical agent on a substrate, comprising discharging at least one pharmaceutical agent in a therapeutically desirable morphology in dry powder form through a first orifice; discharging at least one polymer in dry powder form through a second orifice; depositing the polymer and/or pharmaceutical particles onto said substrate, wherein an electrical potential is maintained between the substrate and the pharmaceutical and/or polymer particles, thereby forming said coating; and sintering said coating under conditions that do not substantially modify the morphology of said pharmaceutical agent.

Although the size, resistivity and moisture content of the polymer and pharmaceutical agent may vary widely based on the conditions used, desired particle sizes are typically in the range of 0.01 µm-2500 µm, and more preferably in the range of 0.01 µm-100 µm, resistivity is typically in the range of from about 106 Ωm to about 1024 Ωm and moisture content is less than 5% by weight. In one embodiment of the invention the molecular weight range of the polymer is from about 5,000 a.u. to about 100,000 a.u. In other embodiments, the first and second orifices are provided as one single orifice wherein the pharmaceutical agent and polymer may be mixed together prior to discharging. In yet other embodiments the pharmaceutical agent and polymer particles may be discharged simultaneously or in succession. In another embodiment of the invention the method further comprises discharging a third dry powder comprising a second pharmaceutical agent whereby a coating comprising at least two different pharmaceutical agents is deposited on said substrate. In some embodiments, the therapeutically desirable morphology of said pharmaceutical agent is crystalline or semi-crystalline, wherein preferably at least 50% of said pharmaceutical agent in powder form is crystalline or semicrystalline. In certain other embodiments of the invention the pharmaceutical agent is prepared by milling, jet-milling, granulation, spray drying, crystallizing or fluidizing and in a preferred embodiment the therapeutically desirable morphology is not substantially changed after the step of sintering the coating. In a further embodiment the pharmaceutical agent and/or the polymer becomes electrostatically charged prior to deposition, and the substrate may be electrically grounded. In a preferred embodiment, the substrate is electrostatically charged. In some embodiments the polymer and pharmaceutical agent are discharged using a gas based propellant, which typically comprises carbon dioxide, nitrous oxide, hydrofluorocarbons, chlorofluorocarbons, helium, nitrogen, compressed air, argon, or volatile hydrocarbons with a vapor pressure greater than 750 Torr at 20° C., and is preferably carbon dioxide. In one embodiment of the invention the pharmaceutical agent comprises at least one drug, which may be selected from Sirolimus, Tacrolimus, Everolimus, Zotarolimus, and Taxol. In another embodiment of the invention the ratio of pharmaceutical agent to polymer is from about 1:50 to about 5:1. In some embodiments, the amount of pharmaceutical agent will depend on the particular agent being employed, the type of substrate, and the medical condition being treated. Typically, the amount of pharmaceutical agent is about 0.001 percent to about 70 percent, more typically about 0.001 percent to about 50 percent, most typically about 0.001 percent to about 20 percent by weight of the polymer/pharmaceutical agent combination. In other embodiments, however, the present invention permits "high load" formulation where the coating composition comprises at least 50, 60, 70 or 80 percent by weight of the pharmaceutical agent, combined with not more than 50, 40, 30 or 20 percent by weight of polymer composition.

Another aspect of the invention provides methods for depositing a coating comprising an active biological agent and a polymer on a substrate, comprising discharging at least one active biological agent through a first orifice; discharging at least one polymer in dry powder form through a second orifice; depositing the active biological agent and/or polymer particles onto said substrate, wherein an electrical potential is maintained between the substrate and the active biological agent and/or polymer particles, thereby forming said coating; and sintering said coating under conditions that do not substantially modify the activity of said biological agent.

In some embodiments the activity of the active biological agent is of therapeutic or prophylactic value and may be influenced by its secondary, tertiary or quaternary structure. In a preferred embodiment of the invention, the active biological agent possesses a secondary, tertiary or quaternary structure which is not substantially changed after sintering. In one embodiment of the invention the active biological agent is a peptide, protein, enzyme, nucleic acid, antisense nucleic acid, antimicrobial, vitamin, hormone, steroid, lipid, polysaccharide or carbohydrate, and may further comprise a stabilizing agent. Most preferably the active biological agent is a peptide, protein or enzyme. In other embodiments, the active biological agent is provided as a dry powder Although the size, resistivity and moisture content of the active biological agent and polymer may vary widely based on the conditions used, desired particle sizes are typically in the range of 0.01 μm-2500 μm, and more preferably in the range of 0.01 μm-100 μm, resistivity is typically in the range of from about 106 Ωm to about 1024 Ωm and moisture content is less than 5% by weight. In one embodiment of the invention the molecular weight range of the polymer is from about 5,000 a.u. to about 100,000 a.u. In other embodiments, the first and second orifices are provided as one single orifice wherein the pharmaceutical agent and polymer may be mixed together prior to discharging. In yet other embodiments the pharmaceutical agent and polymer particles may be discharged simultaneously or in succession. In another embodiment of the invention the method further comprises discharging a second active biological agent whereby a coating comprising at least two different biological agents is deposited on said substrate. In a further embodiment the biological agent and/or the polymer becomes electrostatically charged prior to deposition, and the substrate may be electrically grounded. In a preferred embodiment, the substrate is electrostatically charged. In some embodiments the polymer and biological agent are discharged using a gas based propellant, which typically, comprises carbon dioxide, nitrous oxide, hydrofluorocarbons, chlorofluorocarbons, helium, nitrogen, compressed air or volatile hydrocarbons with a vapor pressure greater than 750 Torr at 20° C., and is preferably carbon dioxide. In another embodiment of the invention the ratio of biological agent to polymer is from about 1:50 to about 5:1. In some embodiments, the amount of biological agent will depend on the particular agent being employed, the type of substrate, and the medical condition being treated. Typically, the amount of biological agent is about 0.001 percent to about 70 percent, more typically about 0.001 percent to about 50 percent, most typically about 0.001 percent to about 20 percent by weight of the polymer/biological agent combination. In other embodiments, however, the present invention permits "high load" formulation where the coating composition comprises at least 50, 60, 70 or 80 percent by weight of the biological agent, combined with not more than 50, 40, 30 or 20 percent by weight of polymer composition.

Yet another aspect of the invention provides methods for depositing a coating comprising a polymer and a pharmaceutical agent on a substrate, comprising discharging at least one pharmaceutical agent in a therapeutically desirable morphology in dry powder form through a first orifice; forming a supercritical or near supercritical fluid mixture that includes at least one supercritical fluid solvent and at least one polymer and discharging said supercritical or near supercritical fluid solution through a second orifice under conditions sufficient to form solid particles of the polymer; depositing the polymer and/or pharmaceutical particles onto said substrate, wherein an electrical potential is maintained between the substrate and the pharmaceutical and/or polymer particles, thereby forming said coating and sintering said coating under conditions that do not substantially modify the morphology of said solid pharmaceutical particles.

Although the size, resistivity and moisture content of the pharmaceutical agent may vary widely based on the conditions used, desired particle sizes are typically in the range of 0.01 μm-2500 μm, and more preferably in the range of 0.01 μm-100 μm, resistivity is typically in the range of from about 106 Ωm to about 1024 Ωm and moisture content is less than 5% by weight. In one embodiment of the invention, the molecular weight range of the polymer is from about 5,000 a.u. to about 100,000 a.u. In one embodiment of the invention the pharmaceutical and polymer particles are discharged simultaneously, while in another embodiment of the invention they are discharged in succession. In another embodiment of the invention the method further comprises discharging a second dry powder comprising a second pharmaceutical agent whereby a coating comprising at least two different pharmaceutical agents is deposited on said substrate. In some embodiments, the therapeutically desirable morphology of said pharmaceutical agent is crystalline or semi-crystalline, wherein preferably at least 50% of said pharmaceutical agent in powder form is crystalline or semicrystalline. In certain other embodiments of the invention the pharmaceutical agent is prepared by milling, jet-milling, granulation, spray drying, crystallizing or fluidizing and in a preferred embodiment the therapeutically desirable morphology is not substantially changed after the step of sintering the coating. In a further embodiment the pharmaceutical agent and/or the polymer becomes electrostatically charged prior to deposition, and the substrate may be electrically grounded. In a preferred embodiment, the substrate is electrostatically charged. In some embodiments the pharmaceutical agent is discharged using a gas based propellant, which typically comprises carbon dioxide, nitrous oxide, hydrofluorocarbons, chlorofluorocarbons, helium, nitrogen, compressed air or volatile hydrocarbons with a vapor pressure greater than 750 Torr at 20° C., and is preferably carbon dioxide. In one embodiment of the invention the pharmaceutical agent comprises at least one drug, which may be selected from [list]. In another embodiment of the invention the ratio of pharmaceutical agent to polymer is from about 1:50 to about 5:1. In some embodiments, the amount of pharmaceutical agent will depend on the particular agent being employed, the type of substrate, and the medical condition being treated. Typically, the amount of pharmaceutical agent is about 0.001 percent to about 70 percent, more typically about 0.001 percent to about 50 percent, most typically about 0.001 percent to about 20 percent by weight of the polymer/pharmaceutical agent combination. In other embodiments, however, the present invention permits "high load" formulation where the coating composition comprises at least 50, 60, 70 or 80 percent by weight of the pharmaceutical agent, combined with not more than 50, 40, 30 or 20 percent by weight of polymer composition.

A further aspect of the invention provides methods for depositing a coating comprising an active biological agent and a polymer on a substrate, comprising discharging at least one active biological agent through a first orifice; forming a supercritical or near supercritical fluid mixture that includes at least one supercritical fluid solvent and at least one polymer and discharging said supercritical or near supercritical fluid solution through a second orifice under conditions sufficient to form solid particles of the polymer; depositing the active biological agent and/or polymer particles onto said substrate, wherein an electrical potential is maintained between the substrate and the active biological agent and/or polymer particles, thereby forming said coating and sintering said coating under conditions that do not substantially modify the activity of said biological agent.

In some embodiments the activity of the active biological agent is of therapeutic or prophylactic value and may be influenced by its secondary, tertiary or quaternary structure. In a preferred embodiment of the invention, the active biological agent possesses a secondary, tertiary or quaternary structure which is not substantially changed after sintering. In one embodiment of the invention the active biological agent is a peptide, protein, enzyme, nucleic acid, antisense nucleic acid, antimicrobial, vitamin, hormone, steroid, lipid, polysaccharide or carbohydrate, and may further comprise a stabilizing agent. Most preferably the active biological agent is a peptide, protein or enzyme. In other embodiments, the active biological agent is provided as a dry powder. Although the size, resistivity and moisture content of the active biological agent may vary widely based on the conditions used, desired particle sizes are typically in the range of 0.01 μm-2500 μm, and more preferably in the range of 0.01 μm-100 μm, resistivity is typically in the range of from about 106 Ωm to about 1024 Ωm and moisture content is less than 5% by weight. In one embodiment of the invention the molecular weight range of the polymer is from about 5,000 a.u. to about 100,000 a.u. In one embodiment of the invention the biological agent and polymer particles are discharged simultaneously, while in another embodiment of the invention they are discharged in succession. In another embodiment of the invention the method further comprises discharging second active biological agent whereby a coating comprising at least two different biological agents is deposited on said substrate. In a further embodiment the biological agent and/or the polymer becomes electrostatically charged prior to deposition, and the substrate may be electrically grounded. In a preferred embodiment, the substrate is electrostatically charged. In some embodiments the biological agent is discharged using a gas based propellant, which typically comprises carbon dioxide, nitrous oxide, hydrofluorocarbons, chlorofluorocarbons, helium, nitrogen, compressed air or volatile hydrocarbons with a vapor pressure greater than 750 Torr at 20° C., and is preferably carbon dioxide. In another embodiment of the invention the ratio of biological agent to polymer is from about 1:50 to about 5:1. In some embodiments, the amount of biological agent will depend on the particular agent being employed, the type of substrate, and the medical condition being treated. Typically, the amount of biological agent is about 0.001 percent to about 70 percent, more typically about 0.001 percent to about 50 percent, most typically about 0.001 percent to about 20 percent by weight of the polymer/biological agent combination. In other embodiments, however, the present invention permits "high load" formulation where the coating composition comprises at least 50, 60, 70 or 80 percent by weight of the biological agent, combined with not more than 50, 40, 30 or 20 percent by weight of polymer composition.

Each of the above methods may be carried out from about 0° C. to about 80° C. and from about 0.1 atmospheres to about 73 atmospheres, in either open or closed vessel. In some embodiments, the substrate is a biomedical implant which may be a stent, electrode, catheter, lead, implantable pacemaker or cardioverter housing, joint, screw, rod, ophthalmic implant, prosthetic or shunt.

In some embodiments of the invention the thickness of said coating is from about 1 to about 100 μm, preferably about 10 μm, and the variation in the thickness along said coating is within 0.5 μm, within 0.25 μm, within 0.1 μm or within 10% of the total thickness of said coating, within 5% of the total thickness of said coating, or within 2.5% of the total thickness of said coating. In other embodiments, the XRD pattern of said pharmaceutical agent or active biological agent comprises at least two, at least five and preferably at least ten of the same peaks after the coating process, as compared to the XRD pattern of said pharmaceutical agent or active biological agent prior to the coating process. In yet other embodiments, the pharmaceutical agent or active biological agent is positioned at a selected distance from top of said coating. In further embodiments, the pharmaceutical agent or active biological agent is positioned at about midway between the top of said coating and the substrate surface. In other embodiments of the invention the variability in the amount of pharmaceutical agent or active biological agent deposited on said substrate is 20% or less, 15% or less, 10% or less, 5% or less, for a batch of substrates coated at the same time. Preferably the variability is 5% or less. In yet other embodiments of the invention, the methods further comprise depositing a top layer on said coating wherein said top layer is a polymer film. In some embodiments, the polymer film has a thickness of 0.5 to 10 microns, and can be deposited by a RESS or SEDS process. In yet other embodiments, the polymer film is formed by depositing a single polymer and can be formed by depositing substantially pure PBMA.

The invention further relates to the use of a supercritical solution comprising a second fluid in its supercritical state.

In some embodiments, the addition of a second fluid in its supercritical state is to act as a flammability suppressor. In other embodiments, a second fluid is used, wherein said second fluid has critical parameters lower than the first fluid's critical parameters, and therefore lowers the critical properties of the mixture/solution enabling access to the mixture supercritical state.

In some embodiments the supercritical solution comprises isobutylene. In other embodiments, the supercritical fluid comprises isobutylene and carbon dioxide as a second fluid.

Other embodiments of the invention provide a way to dissolve two polymers in a supercritical solvent. In some embodiments said two polymers are PEVA and PBMA. In other embodiments, a supercritical solution comprising two polymers is used to create a RESS spray of the polymers generating ~10 to 100 nm particles of each polymer. In further embodiments, PEVA and PBMA are dissolved in a supercritical solvent that further comprises CO2 to act as a fire suppressor in the event of an ignition source causing a fire.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3. Drug-Polymer coated coronary stent (a) immediately after deposition, (b) after annealing in a dense carbon dioxide environment at 40° C.; the photographs correspond to the experiment discussed in conjunction with Example 10.

FIG. 4. 40× Magnified Images of Rapamycin/PEVA/PBMA Coated Stents, Obtained From an Optical Microscope with Back and Side Lighting, Showing the Outside, Edge and Inside Surfaces, (a) before and (b) after sintering, as discussed in example 10.

FIG. 5. 40× Magnified Images of Rapamycin/PEVA/PBMA Coated S tents, Obtained From an Optical Microscope with Back and Side Lighting, Showing the Outside and Inside Surfaces, (a) before and (b) after sintering, as discussed in example 10.

FIGS. 18-24 illustrate particular embodiments of the invention

DETAILED DESCRIPTION OF THE INVENTION

Figure 1:
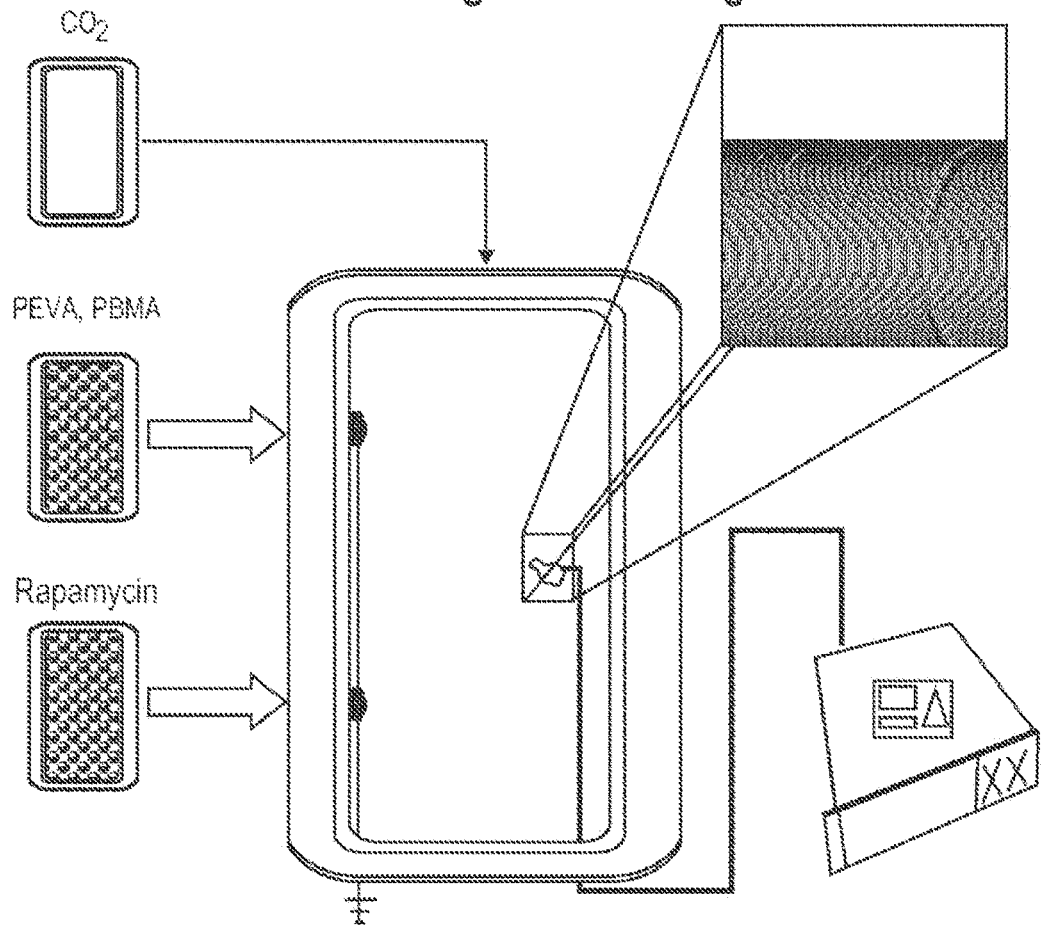
FIG. 1. Schematic Representation of the Coating and Sintering Process Apparatus, as discussed in example 9.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

Applicants specifically intend that all United States patent references cited herein be incorporated herein by reference in their entirety.

The present invention provides a cost-effective, efficient method for depositing a combination of an inert polymer or polymers and a pharmaceutical or biological agent or agents, onto parts or all surfaces of a substrate, to form a coating that is of a pre-determined, desired thickness, conformal, substantially defect-free, and uniform and the composition of the coating can be regulated. In particular, the present invention addresses the problem of existing coating processes, which do not allow for structural and morphological preservation of the agents deposited during the coating process.

The first aspect of the invention entails the deposition of the pharmaceutical or biological agents as dry powders, using electrostatic capture to attract the powder particles to the substrate. Dry powder spraying is well known in the art, and dry powder spraying coupled with electrostatic capture has been described, for example in U.S. Pat. No. 5,470,603 6,319,541 or 6,372,246. The deposition of the polymer can be performed in any number of standard procedures, as the morphology of the polymer, so long as it provides coatings possessing the desired properties (e.g. thickness, conformity, defect-free, uniformity etc), is of less importance. The function of the polymer is primarily one of inert carrier matrix for the active components of the coating.

The second step of the coating process involves taking the substrates that have been coated with pharmaceutical or biological agents and polymers and subjecting them to a sintering process that takes place under benign conditions, which do not affect the structural and morphological integrity of the pharmaceutical and biological agents. The sintering process as used in the current invention refers to the process by which the co-deposited pharmaceutical agent or biological agent-polymer matrix, becomes fused and adherent to the substrate by treatment of the coated substrate with a compressed gas, compressed liquid, or supercritical fluid that is a non-solvent for the polymers, the pharmaceutical agents and the biological agents, but a plasticizing agent for the polymer. The sintering process takes place under conditions (e.g. mild temperatures), and using benign fluids (e.g. supercritical carbon dioxide) which will not affect the structural and morphological integrity of the pharmaceutical and biological agents.

One aspect of the invention is the combination of two or more of the dry powder, RESS and SEDS spraying techniques. In all aspects of the invention a pharmaceutical or biological agent is deposited onto a substrate by dry powder spraying.

A specific aspect of the invention involves the dry powder spraying of a pharmaceutical agent, in a preferred particle size and morphology, into the same capture vessel as a polymer that is also dry powder sprayed, whereby the spraying of the agent and the polymer is sequential or simultaneous.

Another specific aspect of the invention involves the dry powder spraying of an active biological agent, in a preferred particle size and possessing a particular activity, into the same capture vessel as a polymer that is also dry powder sprayed, whereby the spraying of the agent and the polymer is sequential or simultaneous.

Yet another aspect of the invention involves the dry powder spraying of a pharmaceutical agent, in a preferred particle size and morphology, into the same capture vessel as a polymer that is sequentially or simultaneously sprayed by the RESS spray process.

Yet another aspect of the invention involves the dry powder spraying of an active biological agent, in a preferred particle size and possessing a particular activity, into the same capture vessel as a polymer that is sequentially or simultaneously sprayed by the RESS spray process.

Yet another aspect of the invention involves the dry powder spraying of a pharmaceutical agent, in a preferred particle size and morphology, into the same capture vessel as a polymer that is sequentially or simultaneously sprayed by the SEDS spray process.

Yet another aspect of the invention involves the dry powder spraying of an active biological agent, in a preferred particle size and possessing a particular activity, into the same capture vessel as a polymer that is sequentially or simultaneously sprayed by the SEDS spray process.

Any combination of the above six processes is contemplated by this aspect of the invention.

In further aspects of the invention the substrates that have been coated with pharmaceutical or biological agents and polymers, as described in the above embodiments are then subjected to a sintering process. The sintering process takes place under benign conditions, which do not affect the structural and morphological integrity of the pharmaceutical and biological agents, and refers to a process by which the co-deposited pharmaceutical agent or biological agent-polymer matrix, becomes fused and adherent to the substrate. This is achieved by treating the coated substrate with a compressed gas, compressed liquid or supercritical fluid that is a non-solvent for the polymers, the pharmaceutical agents and the biological agents, but a plasticizing agent for the polymer. The sintering process takes place under conditions (e.g. mild temperatures), and using benign fluids (e.g. supercritical carbon dioxide) which will not affect the structural and morphological integrity of the pharmaceutical and biological agents. Other sintering processes, which do not affect the structural and morphological integrity of the pharmaceutical and biological agents may also be contemplated by the present invention.

Definitions

As used in the present specification, the following words and phrases are generally intended to have the meanings as set forth below, except to the extent that the context in which they are used indicates otherwise.

"Substrate" as used herein, refers to any surface upon which it is desirable to deposit a coating comprising a polymer and a pharmaceutical or biological agent, wherein the coating process does not substantially modify the morphology of the pharmaceutical agent or the activity of the biological agent. Biomedical implants are of particular interest for the present invention; however the present invention is not intended to be restricted to this class of substrates. Those of skill in the art will appreciate alternate substrates that could benefit from the coating process described herein, such as pharmaceutical tablet cores, as part of an assay apparatus or as components in a diagnostic kit (e.g. a test strip).

"Biomedical implant" as used herein refers to any implant for insertion into the body of a human or animal subject, including but not limited to stents (e.g., vascular stents), electrodes, catheters, leads, implantable pacemaker, cardioverter or defibrillator housings, joints, screws, rods, ophthalmic implants, femoral pins, bone plates, grafts, anastomotic devices, perivascular wraps, sutures, staples, shunts for hydrocephalus, dialysis grafts, colostomy bag attachment devices, ear drainage tubes, leads for pace makers and implantable cardioverters and defibrillators, vertebral disks, bone pins, suture anchors, hemostatic barriers, clamps, screws, plates, clips, vascular implants, tissue adhesives and sealants, tissue scaffolds, various types of dressings (e.g., wound dressings), bone substitutes, intraluminal devices, vascular supports, etc.

The implants may be formed from any suitable material, including but not limited to organic polymers (including stable or inert polymers and biodegradable polymers), metals, inorganic materials such as silicon, and composites thereof, including layered structures with a core of one material and one or more coatings of a different material. However, the invention contemplates the use of electrostatic capture in conjunction with substrate having low conductivity or which non-conductive. To enhance electrostatic capture when a non-conductive substrate is employed, the substrate is processed while maintaining a strong electrical field in the vicinity of the substrate.

Subjects into which biomedical implants of the invention may be applied or inserted include both human subjects (including male and female subjects and infant, juvenile, adolescent, adult and geriatric subjects) as well as animal subjects (including but not limited to dog, cat, horse, monkey, etc.) for veterinary purposes.

In a preferred embodiment the biomedical implant is an expandable intraluminal vascular graft or stent (e.g., comprising a wire mesh tube) that can be expanded within a blood vessel by an angioplasty balloon associated with a catheter to dilate and expand the lumen of a blood vessel, such as described in U.S. Pat. No. 4,733,665 to Palmaz.

"Pharmaceutical agent" as used herein refers to any of a variety of drugs or pharmaceutical compounds that can be used as active agents to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the pharmaceutical agents of the invention may also comprise two or more drugs or pharmaceutical compounds. Pharmaceutical agents, include but are not limited to antirestenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals, chemotherapeutic agents and amino acids. Examples of suitable active ingredients are acarbose, antigens, beta-receptor blockers, non-steroidal antiinflammatory drugs {NSAIDs], cardiac glycosides, acetylsalicylic acid, virustatics, aclarubicin, acyclovir, cisplatin, actinomycin, alpha- and beta-sympatomimetics, (dmeprazole, allopurinol, alprostadil, prostaglandins, amantadine, ambroxol, amlodipine, methotrexate, S-aminosalicylic acid [sic], amitriptyline, amoxicillin, anastrozole, atenolol, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, ciclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxorubizin, doxylamine, dapiprazole, benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafinil, orlistat, peptide antibiotics, phenytoin, riluzoles, risedronate, sildenafil, topiramate, macrolide antibiotics, oestrogen and oestrogen derivatives, progestogen and progestogen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, roxatidine, roxithromycin, ruscogenin, rutoside and rutoside derivatives, sabadilla, salbutamol, salmeterol, scopolamine, selegiline, sertaconazole, sertindole, sertralion, silicates, sildenafil, simvastatin, sitosterol, sotalol, spaglumic acid, sparfloxacin, spectinomycin, spiramycin, sprapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tetracyclins, teryzoline, theobromine, theophylline, butizine, thiamazole, phenothiazines, thiotepa, tiagabine, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, antioestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobuterol, tyramine, tyrothricin, urapidil, ursodeoxycholic acid, chenodeoxycholic acid, valaciclovir, valproic acid, vancomycin, vecuronium chloride, Viagra, venlafaxine, verapamil, vidarabine, vigabatrin, viloazine, vinblastine, vincamine, vincristine, vindesine, vinorelbine, vinpocetine, viquidil, warfarin, xantinol nicotinate, xipamide, zafirlukast, zalcitabine, zidovudine, zolmitriptan, zolpidem, zoplicone, zotipine and the like. In some non-limiting examples, the pharmaceutical agent is rapamycin, a rapamycin analogue such as for example, zatarolimus, tacrolimus, or everolimus, estradiol, lantrunculin D, cytochalasin A, NO, dexamethasone, paclitaxel, and angiopeptin. See, e.g., U.S. Pat. No. 6,897,205; see also U.S. Pat. Nos. 6,838,528; 6,497,729 Examples of therapeutic agents employed in conjunction with the invention include, rapamycin, 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3 S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin 40-O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1', 2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), and 40-epi-(N1-tetrazolyl)-rapamycin (zotarolimus).

The active ingredients may, if desired, also be used in the form of their pharmaceutically acceptable salts or derivatives (meaning salts which retain the biological effectiveness and properties of the compounds of this invention and which are not biologically or otherwise undesirable), and in the case of chiral active ingredients it is possible to employ both optically active isomers and racemates or mixtures of diastereoisomers.

"Stability" as used herein in refers to the stability of the drug in a polymer coating deposited on a substrate in its final product form (e.g., stability of the drug in a coated stent). The term stability will define 5% or less degradation of the drug in the final product form.

"Active biological agent" as used herein refers to a substance, originally produced by living organisms, that can be used to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the active biological agents of the invention may also comprise two or more active biological agents or an active biological agent combined with a pharmaceutical agent, a stabilizing agent or chemical or biological entity. Although the active biological agent may have been originally produced by living organisms, those of the present invention may also have been synthetically prepared, or by methods combining biological isolation and synthetic modification. By way of a non-limiting example, a nucleic acid could be isolated form from a biological source, or prepared by traditional techniques, known to those skilled in the art of nucleic acid synthesis. Furthermore, the nucleic acid may be further modified to contain non-naturally occurring moieties. Non-limiting examples of active biological agents include peptides, proteins, enzymes, glycoproteins, nucleic acids (including deoxyribonucleotide or ribonucleotide polymers in either single or double stranded form, and unless otherwise limited, encompasses known analogues of natural nucleotides that hybridize to nucleic acids in a manner similar to naturally occurring nucleotides), antisense nucleic acids, fatty acids, antimicrobials, vitamins, hormones, steroids, lipids, polysaccharides, carbohydrates and the like. They further include, but are not limited to, anti-restenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals and chemotherapeutic agents. Preferably, the active biological agent is a peptide, protein or enzyme, including derivatives and analogs of natural peptides, proteins and enzymes.

"Activity" as used herein refers to the ability of a pharmaceutical or active biological agent to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). Thus the activity of a pharmaceutical or active biological agent should be of therapeutic or prophylactic value.

"Secondary, tertiary and quaternary structure" as used herein are defined as follows. The active biological agents of the present invention will typically possess some degree of secondary, tertiary and/or quaternary structure, upon which the activity of the agent depends. As an illustrative, non-limiting example, proteins possess secondary, tertiary and quaternary structure. Secondary structure refers to the spatial arrangement of amino acid residues that are near one another in the linear sequence. The α-helix and the β-strand are elements of secondary structure. Tertiary structure refers to the spatial arrangement of amino acid residues that are far apart in the linear sequence and to the pattern of disulfide bonds. Proteins containing more than one polypeptide chain exhibit an additional level of structural organization. Each polypeptide chain in such a protein is called a subunit. Quaternary structure refers to the spatial arrangement of subunits and the nature of their contacts. For example hemoglobin consists of two α and two β chains. It is well known that protein function arises from its conformation or three dimensional arrangement of atoms (a stretched out polypeptide chain is devoid of activity). Thus one aspect of the present invention is to manipulate active biological agents, while being careful to maintain their conformation, so as not to lose their therapeutic activity.

"Polymer" as used herein, refers to a series of repeating monomeric units that have been cross-linked or polymerized. Any suitable polymer can be used to carry out the present invention. It is possible that the polymers of the invention may also comprise two, three, four or more different polymers. In some embodiments, of the invention only one polymer is used. In some preferred embodiments a combination of two polymers are used. Combinations of polymers can be in varying ratios, to provide coatings with differing properties. Those of skill in the art of polymer chemistry will be familiar with the different properties of polymeric compounds. Examples of polymers that may be used in the present invention include, but are not limited to polycarboxylic acids, cellulosic polymers, proteins, polypeptides, polyvinylpyrrolidone, maleic anhydride polymers, polyamides, polyvinyl alcohols, polyethylene oxides, glycosaminoglycans, polysaccharides, polyesters, bacterial polyesters (PHB, PHV), polyurethanes, polystyrenes, copolymers, silicones, polyorthoesters, polyanhydrides, copolymers of vinyl monomers, polycarbonates, polyethylenes, polypropylenes, polylactic acids, polyglycolic acids, polycaprolactones, polyhydroxybutyrate valerates, polyacrylamides, polyethers, polyurethane dispersions, polyacrylates, acrylic latex dispersions, polyacrylic acid, mixtures and copolymers thereof. The polymers of the present invention may be natural or synthetic in origin, including gelatin, chitosan, dextrin, cyclodextrin, Poly(urethanes), Poly(siloxanes) or silicones, Poly(acrylates) such as poly(methyl methacrylate), poly(butyl methacrylate), and Poly(2-hydroxy ethyl methacrylate), Poly(vinyl alcohol) Poly(olefins) such as poly(ethylene), poly(isoprene), halogenated polymers such as Poly(tetrafluoroethylene)—and derivatives and copolymers such as those commonly sold as Teflon® products, Poly(vinylidine fluoride), Poly(vinyl acetate), Poly (vinyl pyrrolidone), Poly(acrylic acid), Polyacrylamide, Poly(ethylene-co-vinyl acetate), Poly(ethylene glycol), Poly (propylene glycol), Poly(methacrylic acid), Poly(dimethyl)-siloxane, Polyethyene terephthalate, Polyethylene-vinyl acetate copolymer (PEVA), Ethylene vinyl alcohol (EVAL), Ethylene vinyl acetate (EVA), Poly(styrene-b-isobutylene-b-styrene) (SIBBS), Phosophorycholine (PC), styrene-isobutylene, fluorinated polymers, polyxylenes (PARYLENE), tyrosine based polycarbonates, tyrosine based polyarylates, poly(trimethylene carbonate), hexafluoropropylene, vinylidene fluoride, butyl methacrylate, hexyl methacrylate, vinyl pyrrolidinone, vinyl acetate, etc. Suitable polymers also include absorbable and/or resorbable polymers including the following, combinations, copolymers and derivatives of the following: Polylactides (PLA), Polyglycolides (PGA), Poly(lactide-co-glycolides) (PLGA), Polyanhydrides, Polyorthoesters, Poly(N-(2-hydroxypropyl) methacrylamide), Poly(l-aspartamide), Polyhydro-butyrate/-valerate copolymer, Polyethyleneoxide/polybutylene terephthalate copolymer, etc.

"Therapeutically desirable morphology" as used herein refers to the gross form and structure of the pharmaceutical agent, once deposited on the substrate, so as to provide for optimal conditions of ex vivo storage, in vivo preservation and/or in vivo release. Such optimal conditions may include, but are not limited to increased shelf life, increased in vivo stability, good biocompatibility, good bioavailability or modified release rates. Typically, for the present invention, the desired morphology of a pharmaceutical agent would be crystalline or semi-crystalline, although this may vary widely depending on many factors including, but not limited to, the nature of the pharmaceutical agent, the disease to be treated/prevented, the intended storage conditions for the substrate prior to use or the location within the body of any biomedical implant. Preferably at least 10%, 20%, 30%, 40%, 50%, 60%, 70%, 80%, 90% or 100% of the pharmaceutical agent is in crystalline or semi-crystalline form.

"Stabilizing agent" as used herein refers to any substance that maintains or enhances the stability of the biological agent. Ideally these stabilizing agents are classified as Generally Regarded As Safe (GRAS) materials by the US Food and Drug Administration (FDA). Examples of stabilizing agents include, but are not limited to carrier proteins, such as albumin, gelatin, metals or inorganic salts. Pharmaceutically acceptable excipient that may be present can further be found in the relevant literature, for example in the Handbook of Pharmaceutical Additives: An International Guide to More Than 6000 Products by Trade Name, Chemical, Function, and Manufacturer; Michael and Irene Ash (Eds.); Gower Publishing Ltd.; Aldershot, Hampshire, England, 1995.

"Compressed fluid" as used herein refers to a fluid of appreciable density (e.g., >0.2 g/cc) that is a gas at standard temperature and pressure. "Supercritical fluid", "near-critical fluid", "near-supercritical fluid", "critical fluid", "densified fluid" or "densified gas" as used herein refers to a compressed fluid under conditions wherein the temperature is at least 80% of the critical temperature of the fluid and the pressure is at least 50% of the critical pressure of the fluid.

Examples of substances that demonstrate supercritical or near critical behavior suitable for the present invention include, but are not limited to carbon dioxide, isobutylene, ammonia, water, methanol, ethanol, ethane, propane, butane, pentane, dimethyl ether, xenon, sulfur hexafluoride, halogenated and partially halogenated materials such as chlorofluorocarbons, hydrochlorofluorocarbons, hydrofluorocarbons, perfluorocarbons (such as perfluoromethane and perfuoropropane, chloroform, trichloro-fluoromethane, dichloro-difluoromethane, dichloro-tetrafluoroethane) and mixtures thereof.

"Sintering" as used herein refers to the process by which parts of the matrix or the entire polymer matrix becomes continuous (e.g., formation of a continuous polymer film). As discussed below, the sintering process is controlled to produce a fully conformal continuous matrix (complete sintering) or to produce regions or domains of continuous coating while producing voids (discontinuities) in the matrix. As well, the sintering process is controlled such that some phase separation is obtained between polymer different polymers (e.g., polymers A and B) and/or to produce phase separation between discrete polymer particles. Through the sintering process, the adhesions properties of the coating are improved to reduce flaking of detachment of the coating from the substrate during manipulation in use. As described below, in some embodiments, the sintering process is controlled to provide incomplete sintering of the polymer matrix. In embodiments involving incomplete sintering, a polymer matrix is formed with continuous domains, and voids, gaps, cavities, pores, channels or, interstices that provide space for sequestering a therapeutic agent which is released under controlled conditions. Depending on the nature of the polymer, the size of polymer particles and/or other polymer properties, a compressed gas, a densified gas, a near critical fluid or a super-critical fluid may be employed. In one example, carbon dioxide is used to treat a substrate that has been coated with a polymer and a drug, using dry powder and RESS electrostatic coating processes. In another example, isobutylene is employed in the sintering process. In other examples a mixture of carbon dioxide and isobutylene is employed.

When an amorphous material is heated to a temperature above its glass transition temperature, or when a crystalline material is heated to a temperature above a phase transition temperature, the molecules comprising the material are more mobile, which in turn means that they are more active and thus more prone to reactions such as oxidation. However, when an amorphous material is maintained at a temperature below its glass transition temperature, its molecules are substantially immobilized and thus less prone to reactions. Likewise, when a crystalline material is maintained at a temperature below its phase transition temperature, its molecules are substantially immobilized and thus less prone to reactions. Accordingly, processing drug components at mild conditions, such as the deposition and sintering conditions described herein, minimizes cross-reactions and degradation of the drug component. One type of reaction that is minimized by the processes of the invention relates to the ability to avoid conventional solvents which in turn minimizes autoxidation of drug, whether in amorphous, semi-crystalline, or crystalline form, by reducing exposure thereof to free radicals, residual solvents and autoxidation initiators.

""Rapid Expansion of Supercritical Solutions" or "RESS" as used herein involves the dissolution of a polymer into a compressed fluid, typically a supercritical fluid, followed by rapid expansion into a chamber at lower pressure, typically near atmospheric conditions. The rapid expansion of the supercritical fluid solution through a small opening, with its accompanying decrease in density, reduces the dissolution capacity of the fluid and results in the nucleation and growth of polymer particles. The atmosphere of the chamber is maintained in an electrically neutral state by maintaining an isolating "cloud" of gas in the chamber. Carbon dioxide or other appropriate gas is employed to prevent electrical charge is transferred from the substrate to the surrounding environment.

"Bulk properties" properties of a coating including a pharmaceutical or a biological agent that can be enhanced through the methods of the invention include for example: adhesion, smoothness, conformality, thickness, and compositional mixing.

"Solution Enhanced Dispersion of Supercritical Solutions" or "SEDS" as used herein involves a spray process for the generation of polymer particles, which are formed when a compressed fluid (e.g. supercritical fluid, preferably supercritical $CO_2$) is used as a diluent to a vehicle in which a polymer dissolved, (one that can dissolve both the polymer and the compressed gas). The mixing of the compressed fluid diluent with the polymer-containing solution may be achieved by encounter of a first stream containing the polymer solution and a second stream containing the diluent compressed fluid, for example, within one co-axial spray nozzle or by the use of multiple spray nozzles or by the use of multiple fluid streams co-entering into a mixing zone. The solvent in the polymer solution may be one compound or a mixture of two or more ingredients and may be or comprise an alcohol (including diols, triols, etc.), ether, amine, ketone, carbonate, or alkanes, or hydrocarbon (aliphatic or aromatic) or may be a mixture of compounds, such as mixtures of alkanes, or mixtures of one or more alkanes in combination with additional compounds such as one or more alcohols. (e.g., from 0 or 0.1 to 5% of a Ci to C15 alcohol, including diols, triols, etc.). See for example U.S. Pat. No. 6,669,785. The solvent may optionally contain a surfactant, as also described in (for example) U.S. Pat. No. 6,669,785.

In one embodiment of the SEDS process, a first stream of fluid comprising a polymer dissolved in a common solvent is co-sprayed with a second stream of compressed fluid. Polymer particles are produced as the second stream acts as a diluent that weakens the solvent in the polymer solution of the first stream. The now combined streams of fluid, along with the polymer particles, flow into a collection vessel. In another embodiment of the SEDS process, a first stream of fluid comprising a drug dissolved in a common solvent is co-sprayed with a second stream of compressed fluid. Drug particles are produced as the second stream acts as a diluent that weakens the solvent in the drug solution of the first stream. The now combined streams of fluid, along with the drug particles, flow out into a collection vessel. Control of particle size, particle size distribution, and morphology is achieved by tailoring the following process variables: temperature, pressure, solvent composition of the first stream, flow-rate of the first stream, flow-rate of the second stream, composition of the second stream (where soluble additives may be added to the compressed gas), and conditions of the capture vessel. Typically the capture vessel contains a fluid phase that is at least five to ten times (5-10×) atmospheric pressure.

"Electrostatically charged" or "electrical potential" or "electrostatic capture" as used herein refers to the collection of the spray-produced particles upon a substrate that has a different electrostatic potential than the sprayed particles. Thus, the substrate is at an attractive electronic potential with respect to the particles exiting, which results in the capture of the particles upon the substrate. i.e. the substrate and particles are oppositely charged, and the particles transport through the fluid medium of the capture vessel onto the surface of the substrate is enhanced via electrostatic attraction. This may be achieved by charging the particles and grounding the substrate or conversely charging the substrate and grounding the particles, or by some other process, which would be easily envisaged by one of skill in the art of electrostatic capture.

"Open vessel" as used herein refers to a vessel open to the outside atmosphere, and thus at substantially the same temperature and pressure as the outside atmosphere.

"Closed vessel" as used herein refers to a vessel sealed from the outside atmosphere, and thus may be at significantly different temperatures and pressures to the outside atmosphere.

EXAMPLES

The following examples are given to enable those skilled in the art to more clearly understand and to practice the present invention. They should not be considered as limiting the scope of the invention, but merely as being illustrative and representative thereof.

Example 1. Dry Powder Rapamycin Coating on an Electrically Charged 316 Stainless Steel Coupon A 1 cm×2 cm stainless steel metal coupon serving as a target substrate for rapamycin coating was placed in a vessel and attached to a high voltage electrode. The vessel (V), of approximately 1500 cm$^3$ volume, was equipped with two separate nozzles through which rapamycin or polymers could be selectively introduced into the vessel. Both nozzles were grounded. Additionally, the vessel (V) was equipped with a separate port was available for purging the vessel. Upstream of one nozzle (D) was a small pressure vessel (PV) approximately 5 cm$^3$ in volume with three ports to be used as inlets and outlets. Each port was equipped with a valve which could be actuated opened or closed. One port, port (1) used as an inlet, was an addition port for the dry powdered rapamycin. Port (2), also an inlet was used to feed pressurized gas, liquid, or supercritical fluid into PV. Port (3), used as an outlet, was used to connect the pressure vessel (PV) with nozzle (D) contained in the primary vessel (V) with the target coupon. Dry powdered rapamycin obtained from LC Laboratories in a predominantly crystalline solid state, 50 mg milled to an average particle size of approximately 3 microns, was loaded into (PV) through port (1) then port (1) was actuated to the closed position. Gaseous carbon dioxide was then added to (PV) to a pressure of 400 to 600 psig at 20° C. through port (2), then port (2) was closed to the source gas. The metal coupon was then charged to 40 kV using a Glassman Series EL high-voltage power source. Port (3) was then actuated open allowing for the expansion of the pressurized carbon dioxide and rapamycin powder into the vessel (V) while the coupon remained charged. After approximately 60-seconds the voltage was eliminated and the coupon was isolated. Upon visual inspection of the coupon using an optical microscope it was determined that the entire surface area of the coupon, other than a small portion masked by the voltage lead, was covered in a relatively even distribution of powdered material. X-ray diffraction (XRD) confirmed that the powdered material was largely crystalline in nature as deposited on the metal coupon. UV-Vis and FTIR spectroscopy confirmed that the material deposited on the coupon was rapamycin.

Example 2. Dry Powder Rapamycin Coating on a 316-Stainless Steel Coupon with No Electrical Charge A coupon was coated in an identical fashion to what was described in Example 1. However, no voltage was applied to the coupon throughout the dry powder-coating run. After expansion of the carbon dioxide and the powdered rapamycin into vessel (V), and a period of roughly 60 seconds, the coupon was isolated and evaluated. The coupon was analyzed using an optical microscope and showed some dry powder material on much of the surface of the coupon. However, the coverage of drug on the surface was much lower than in example 1 and there was notably more variability in coverage at different locations on the coupon surface. The total powder coating was estimated to be about ⅓ the amount determined to be crystalline rapamycin in example 1.

Example 3. Polymer Coating on an Electrically Charged 316-Stainless Steel Coupon Using Rapid Expansion from a Liquefied Gas A coating apparatus as described in example 1 above was used in the foregoing example. In this example the second nozzle, nozzle (P), was used to feed precipitated polymer particles into vessel (V) to coat a 316-stainless steel coupon. Nozzle (P) was equipped with a heater and controller to minimize heat loss due to the expansion of liquefied gases. Upstream of nozzle (P) was a pressure vessel, (PV2), with approximately 25-cm3 internal volume. The pressure vessel (PV2) was equipped with multiple ports to be used for inlets, outlets, thermocouples, and pressure transducers. Additionally, (PV2) was equipped with a heater and a temperature controller. Each port was connected to the appropriate valves, metering valves, pressure regulators, or plugs to ensure adequate control of material into and out of the pressure vessel (PV2). One outlet from (PV2) was connected to a metering valve through pressure rated tubing which was then connected to nozzle (P) located in vessel (V). In the experiment, 75 mg of polyethylene-co-vinyl acetate (PEVA) obtained from Aldrich Chemical Company with approximately 33-weight percent vinyl acetate and 75 mg of poly (butyl methacrylate) (PBMA) also obtained from Aldrich Chemical Company were added to pressure vessel (PV2). Dichlorofluoromethane, 20.0 grams, was added to the pressure vessel (PV2) through a valve and inlet. Pressure vessel (PV2) was then heated to 40° C. bringing the pressure inside the isolated vessel to approximately 40 psig. Nozzle (P) was heated to 120° C. After sufficient time to dissolve the two polymers in the liquefied gas inside (PV2), the vessel (PV2) was over-pressurized with helium to approximately 200 psig using a source helium tank and a dual stage pressure regulator. See U.S. Pat. No. 6,905,555 for a description of Helium displacement art. A 1-cm×2-cm 316-stainless steel coupon was placed into vessel (V) and attached to an electrical lead. Nozzle (P) was attached to ground. The coupon was charged to 40 kV using a Glassman high-voltage power source at which point the metering valve was opened between (PV2) and nozzle (P) in pressure vessel (PV). Polymer dissolved in liquefied gas and over-pressurized with helium to 200 psig was fed at a constant pressure of 200 psig into vessel (V) maintained at atmospheric pressure through nozzle (P) at an approximate rate of 3.0 cm$^3$/min. After approximately 5 seconds, the metering valve was closed discontinuing the polymer-solvent feed. Vessel (V) was purged with gaseous $CO_2$ for 30 seconds to displace chlorofluorocarbon. After approximately 30 seconds, the metering valve was again opened for a period of approximately 5 seconds and then closed. This cycle was repeated about 4 times. After an additional 1-minute the applied voltage to the coupon was discontinued and the coupon was removed from pressure vessel (V). Upon inspection by optical microscope, a polymer coating was evident as evenly distributed on all non-masked surfaces of the coupon. Dissolution of the polymer mixture from the surface of the coupon followed by quantification using standardized quantitative FT-IR methods determined a composition of approximately 1:1 PEVA to PBMA on the coupon.

Example 4. Dual Coating of a Metal Coupon with Crystalline Rapamycin, and 1:1 Mixture of Polyethylene-Co-Vinyl Acetate (PEVA) and Poly(Butyl Methacrylate) (PBMA)

An apparatus described in example '1' and further described in example '3' was used in the foregoing example. In preparation for the coating experiment, 25 mg of crystalline powdered rapamycin with an average particle size of 3-microns was added to (PV) through port (1), then port (1) was closed. Then, (PV) was pressurized to 400-600 psig with gaseous carbon dioxide at 20° C. through port (2), prior to closing port (2). Next, 75 mg of polyethylene-co-vinyl acetate (PEVA) with approximately 33-weight percent vinyl acetate and 75 mg of poly(butyl methacrylate) (PBMA) were added to pressure vessel (PV2). Dichlorofluoromethane, 20.0 grams, was added to the pressure vessel (PV2) through a valve and inlet. Pressure vessel (PV2) was then heated to 40° C. bringing the pressure inside the isolated vessel (PV2) to approximately 40 psig. Nozzle (P) was heated to 120° C. After sufficient time to dissolve the two polymers in the liquefied gas, the vessel was over-pressurized with helium to approximately 200 psig using a source helium tank and a dual stage pressure regulator. A 1-cm×2-cm 316-stainless steel coupon was added to vessel (V) and connected to a high-voltage power lead. Both nozzles (D) and (P) were grounded. To begin, the coupon was charged to 40 kV after which port (3) connecting (PV) containing rapamycin to nozzle (D) was opened allowing expansion of carbon dioxide and ejection of rapamycin into vessel (V) maintained at ambient pressure. After closing port (3) and approximately 60-seconds, the metering valve connecting (PV2) with nozzle (P) inside vessel (V) was opened allowing for expansion of liquefied gas to a gas phase and introduction of precipitated polymer particles into vessel (V) while maintaining vessel (V) at ambient pressure. After approximately 5-seconds at a feed rate of approximately 3 cm$^3$/min., the metering valve was closed while the coupon remained charged. Port (1) was then opened and an additional 25-mg of powdered crystalline rapamycin was added to (PV), and then port (1) was closed. Pressure vessel (PV) was then pressurized with liquid carbon dioxide to 400-600 psig through port (2), after which port (2) was again closed. Maintaining the coupon at an applied voltage of 40 kV, port (3) was again opened to nozzle (D) allowing for the expansion of carbon dioxide to a gas and the ejection of the powdered crystalline drug into the vessel (V). After and additional 60-seconds, the metering valve between (PV2) and nozzle (P) was again opened allowing for the expansion of the liquefied solvent to a gas into vessel (V) and the precipitation of polymer particles also in vessel (V). The sequential addition of drug followed by polymer or polymer followed by drug as described above was repeated for a total of four (4) cycles after which the applied potential was removed from the coupon and the coupon was removed from the vessel. The coupon was then examined using an optical microscope. A consistent coating was visible on all surfaces of the coupon except where the coupon was masked by the electrical lead. The coating appeared conformal but opaque and somewhat granular at high magnification.

Example 5. Dual Coating of a Metal Coupon with Crystalline Rapamycin, and 1:1 Mixture of Polyethylene-Co-Vinyl Acetate (PEVA) and Poly(Butyl Methacrylate) (PBMA) Followed by Supercritical Carbon Dioxide Annealing or Gaseous Carbon Dioxide Annealing After inspection of the coupon created in example 4, the coated coupon was carefully placed in a pressure vessel that was pressurized with carbon dioxide to a pressure of 4500 psig and at a temperature of 60° C. This $CO_2$ sintering process was done to enhance the physical properties of the film on the coupon. The coupon remained in the vessel under these conditions for approximately 3 hours after which the supercritical $CO_2$ was slowly vented from the pressure vessel and then the coupon was removed and reexamined under an optical microscope. The coating was observed to be conformal, consistent, and semi-transparent as opposed to the opaque coating observed and reported in example 4 without dense carbon dioxide treatment. The coated coupon was then submitted for x-ray diffraction (XRD) analysis to confirm the presence of crystalline rapamycin in the polymer matrix. XRD confirmed the presence of crystalline rapamycin.

Example 6. Dual Coating of a Metal Cardiovascular Stent with Crystalline Rapamycin, and 1:1 Mixture of Polyethylene-Co-Vinyl Acetate (PEVA) and Poly (Butyl Methacrylate) (PBMA)

The apparatus described in examples 1, 3, and 4 above was used in the foregoing example. The metal stent used was a Tristar™ Coronary Stent of a nominal size of 3 mm by 13 mm. The stent was coated in an identical fashion to the coupon described in example 4 above. The stent was coated in an alternating fashion whereby the first coating layer of drug was followed by a thin layer of polymer. These two steps, called a drug/polymer cycle, were repeated 3-times so that the last applied coating layer was polymer. After completion of the coating step, the stent was removed from the vessel (V) and placed in a small pressure vessel where it was exposed to supercritical $CO_2$ as described above in example 4. After this low temperature annealing step, the stent was removed and examined using an optical microscope. The stent was then analyzed using a scanning electron microscope (SEM) equipped with a fast ion bombarding (FIB) device to provide cross-sectional analysis of the coated stent. The SEM micrograph at multiple locations on the stent indicated a completely conformal coating of between 6 and 15-microns in thickness. Evidence of rapamycin crystallites was also apparent in the micrographs.

Example 7. Layered Coating of a Cardiovascular Stent with an Anti-Restenosis Therapeutic and Polymer in Layers to Control Drug Elution Characteristics A cardiovascular stent is coated using the methods described in examples '5' and '6' above. The stent is coated in such as way that the drug and polymer are in alternating layers. The first application to the bare stent is a thin layer of a non-resorbing polymer, approximately 2-microns thick. The second layer is a therapeutic agent with anti-restenosis indication. Approximately 35 micrograms are added in this second layer. A third layer of polymer is added at approximately 2-microns thick, followed by a fourth drug layer which is composed of about 25 micrograms of the anti-restenosis agent. A fifth polymer layer, approximately 1-micron thick is added to stent, followed by the sixth layer that includes the therapeutic agent of approximately 15-micrograms. Finally, a last polymer layer is added to a thickness of about 2-microns. After the coating procedure, the stent is annealed using carbon dioxide as described in example 4 above. In this example a drug eluting stent (DES) is described with low initial drug "burst" properties by virtue of a "sequestered drug layering" process, not possible in conventional solvent-based coating processes. Additionally, by virtue of a higher concentration of drug at the stent 'inter-layer' the elution profile is expected to reach as sustained therapeutic release over a longer period of time.

Example 8. Layered Coating of a Cardiovascular Stent with an Anti-Restenosis Therapeutic and an Anti-Thrombotic Therapeutic in a Polymer Matrix A cardiovascular stent is coated as described in example 7 above. In this example, after a first polymer layer of approximately 2-microns thick, a drug with anti-thrombotic indication is added in a layer of less than 2-microns in thickness. A third layer consisting of the non-resorbing polymer is added to a thickness of about 4-microns. Next another drug layer is added, a different therapeutic, with an anti-restenosis indication. This layer contains approximately 100 micrograms of the anti-restenosis agent. Finally, a polymer layer approximately 2-microns in thickness is added to the stent. After coating the stent is treated as described in example 4 to anneal the coating using carbon dioxide.

Example 9. Coating of Stents with Rapamycin, Polyethylene-Co-Vinyl Acetate (PEVA) and Polybutyl Methacrylate (PBMA)

Figure 2:
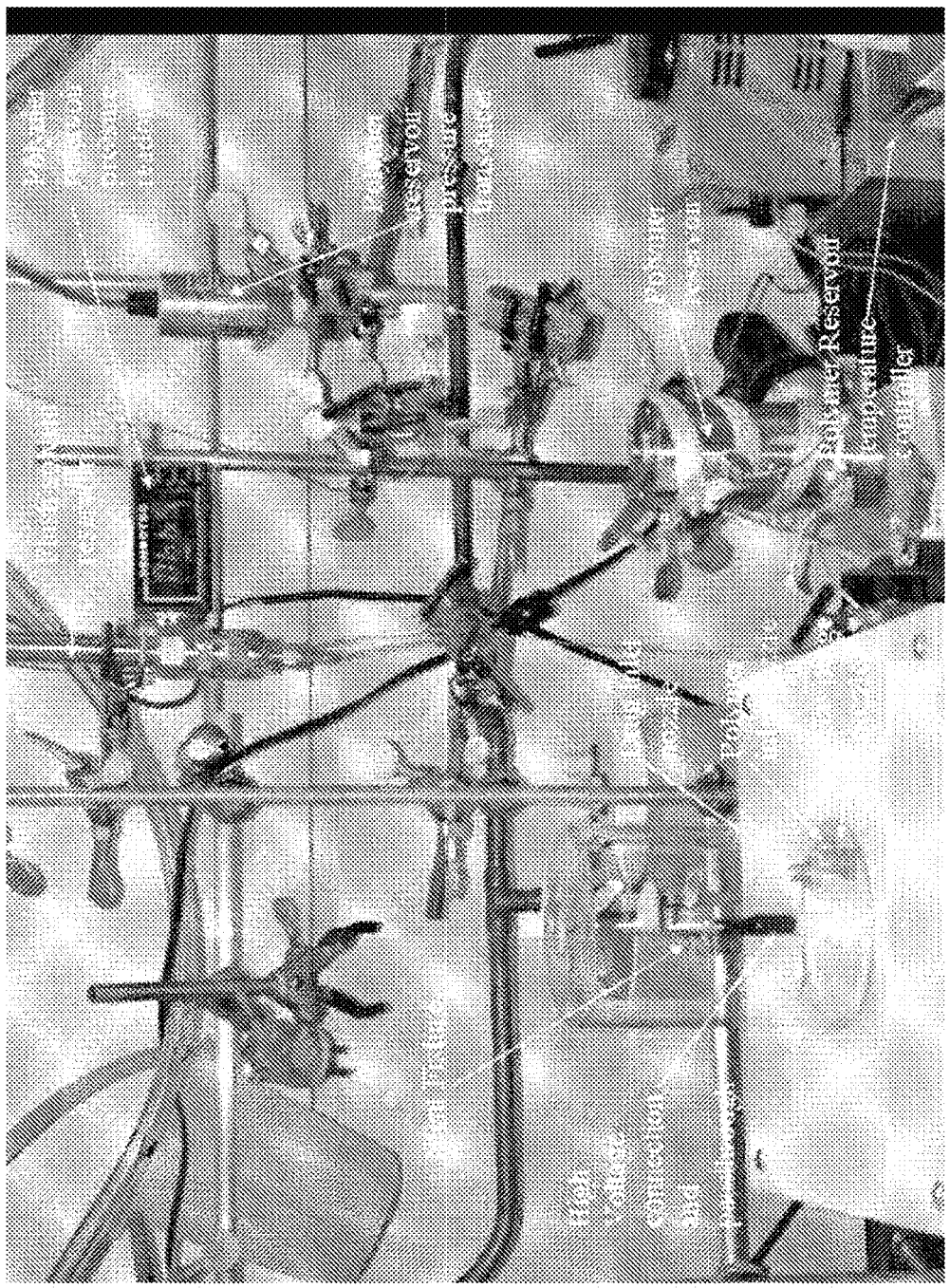
FIG. 2. Detailed images of the Coating and Sintering Process Apparatus, as discussed in example 9.
Figure 2:
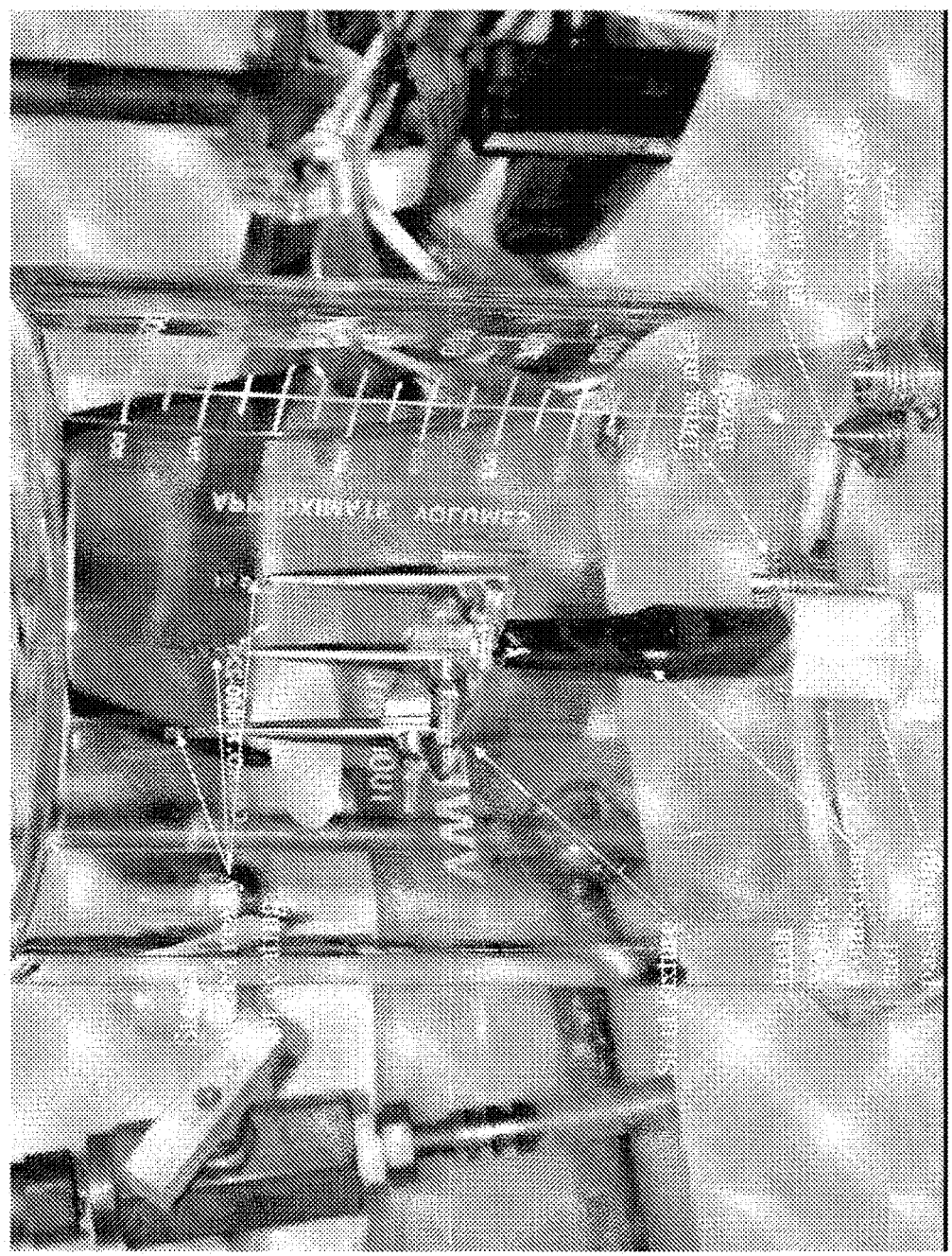
Figure 2:
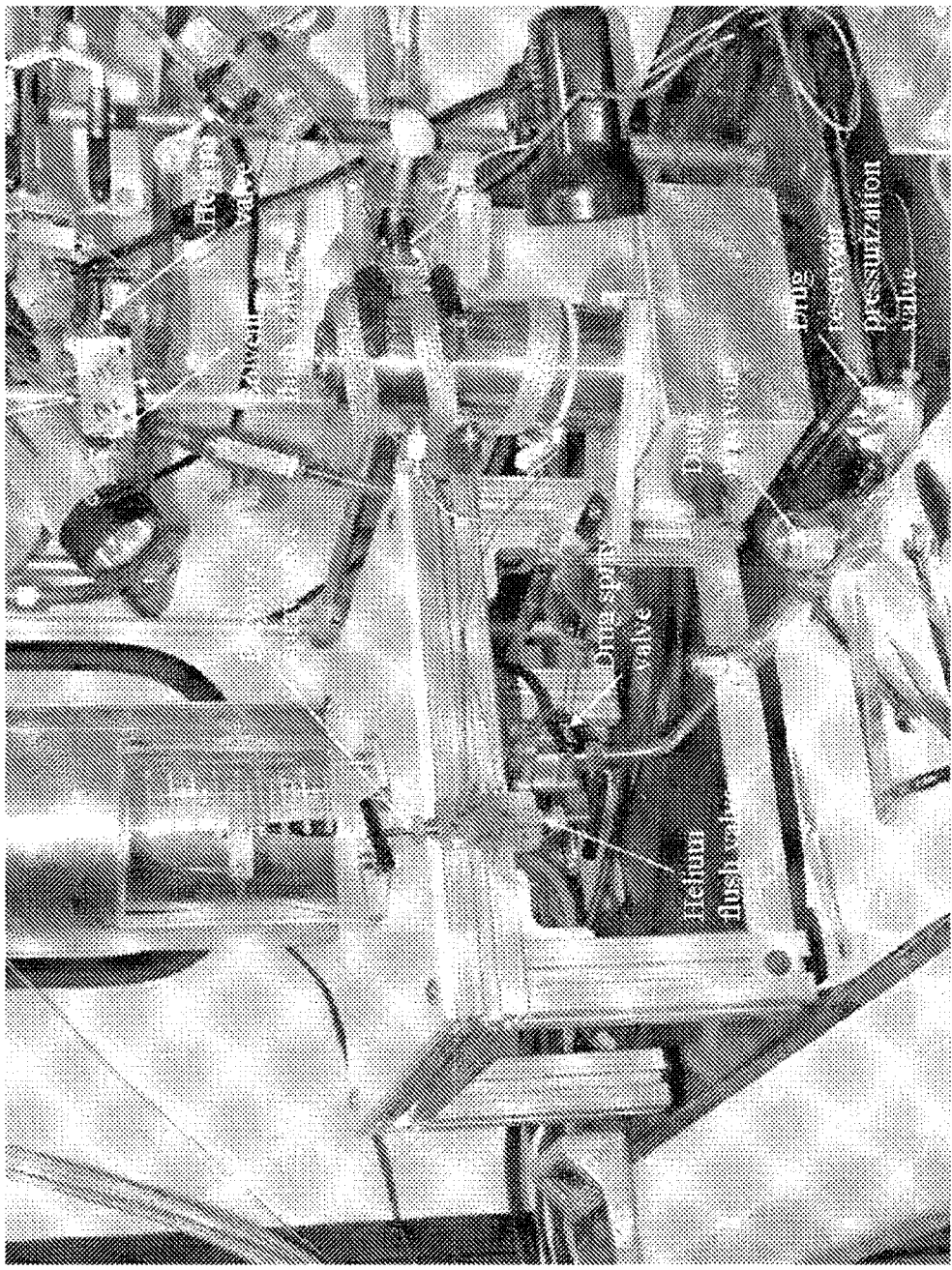

Micronized Rapamycin was purchased from LC Laboratories. PBMA (Mw=~237k) and PEVA (33% vinyl acetate content) were purchased from Aldrich Chemicals. Two kinds of stents were used: 3 mm TriStar® from Guidant and 6 cell×8-mm, BX Velocity® from Cordis. The stents were coated by dry electrostatic capture followed by supercritical fluid sintering, using 3 stents/coating run and 3 runs/data set. The coating apparatus is represented in FIG. 2. Analysis of the coated stents was performed by multiple techniques on both stents and coupons with relevant control experiments.

In this example a 1:1 ratio of PEVA and PBMA is dissolved in a Dichlorofluoromethane ($CCl_2FH$), which is a compressed gas solvent known to be in the class of "Freon" chemicals. The physical properties of this particular Freon are as follows:

BP=8.9 C
Tc=178.33 C
Pc=751.47 psig
Dc=0.526014 g/cc

A solution was formed by mixing 30 mg of the combined polymers per gram dichlorofluoromethane. The solution was then maintained at 60° C. at vapor pressure (approx 28 psig) until the solution was ready to spray. The solution was then pressurized by adding an immiscible gas to the top of the vessel—typically Helium. Adding Helium compressed the Freon+polymer solution up to 700 (+/−50 psig), which resulted in a compressed fluid. The polymer+Freon solution was then pushed through a nozzle having an inner diameter of 0.005" by continuous addition of Helium into the vessel. The solvent (dichlorofluoromethane) is rapidly vaporized coming out of the nozzle (which is heated to 120 C), as it's boiling point is significantly below room temperature.

The Drug is deposited by dry powder spray coating. Between 10-30 mg of drug are charged into a small volume of tubing, which is then pressurized with gaseous $CO_2$ to 400 psig. The mixture flows through a nozzle having an inner diameter of 0.187" into the coating vessel where the stents are held. During electrostatic deposition, the stent is charged and the nozzles are grounded. FIGS. 1 and 2 show the apparatus used for the coating and sintering process.

Example 10. Optical Microscopy Analysis of Rapamycin/PEVA/PBM Coated Stents

Figure 6:
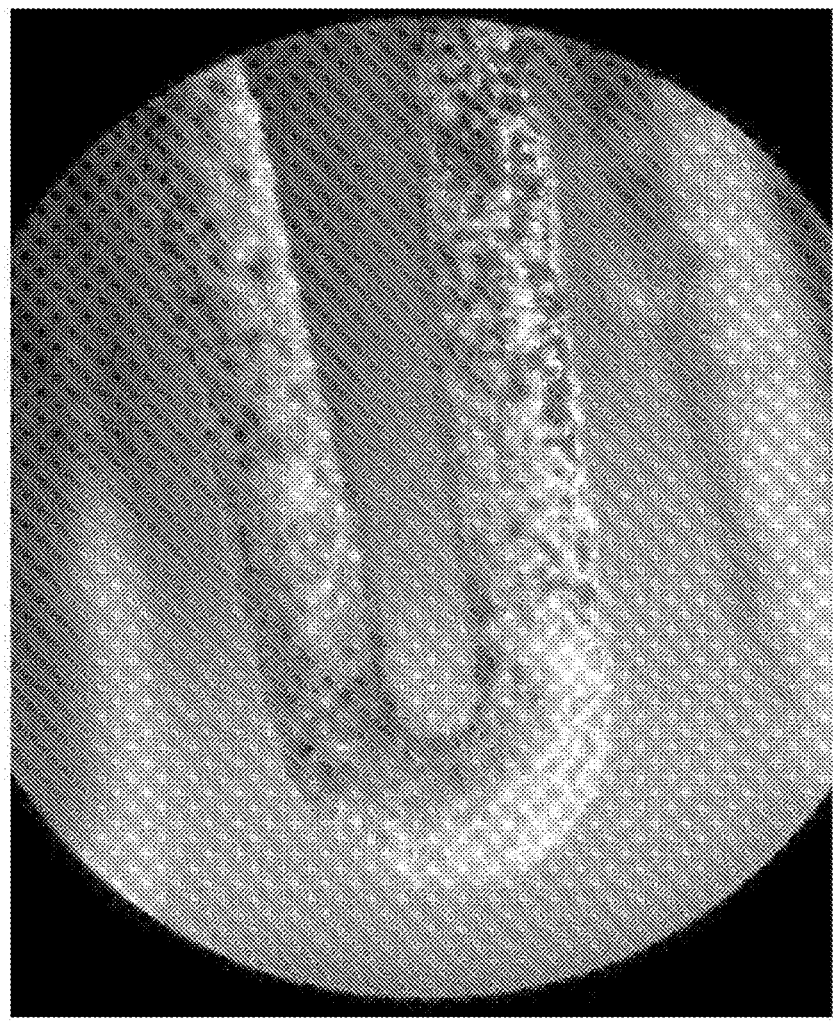
FIG. 6. 100× Magnified Image of a Rapamycin/PEVA/PBMA Coated Stent, Obtained From an Optical Microscope. Crystalline drug is clearly visible embedded within a highly uniform polymer coating, as discussed in example 10.

The stents produced in example 9 were examined by optical microscopy, at 40× magnification with back and side lighting. This method was used to provide a coarse qualitative representation of coating uniformity and to generally demonstrate the utility of the low-temperature $CO_2$ annealing step. The resulting photos shown in FIG. 3, demonstrate the differences in appearance (a) before and (b) after annealing in dense carbon dioxide at 40° C. Photos of the outside, edge and inside surfaces are presented in FIG. 4 (a), prior to sintering, which clearly shows nanoparticle deposition equally on all surfaces of the stent, and 4(b) after sintering, with the film showing a smooth and optically transparent polymer. FIG. 5 shows additional 40× magnified images of Rapamycin/PEVA/PBMA coated stents, showing the outside and inside surfaces, (a) before sintering, further demonstrating the nanoparticle deposition equally on all surfaces of the stent and (b) after sintering, showing a smooth and optically transparent polymer film. FIG. 6 shows a 100× magnified mages of Rapamycin/PEVA/PBMA Coated Stents. Crystalline drug is clearly visible embedded within a highly uniform polymer coating.

Figure 7:
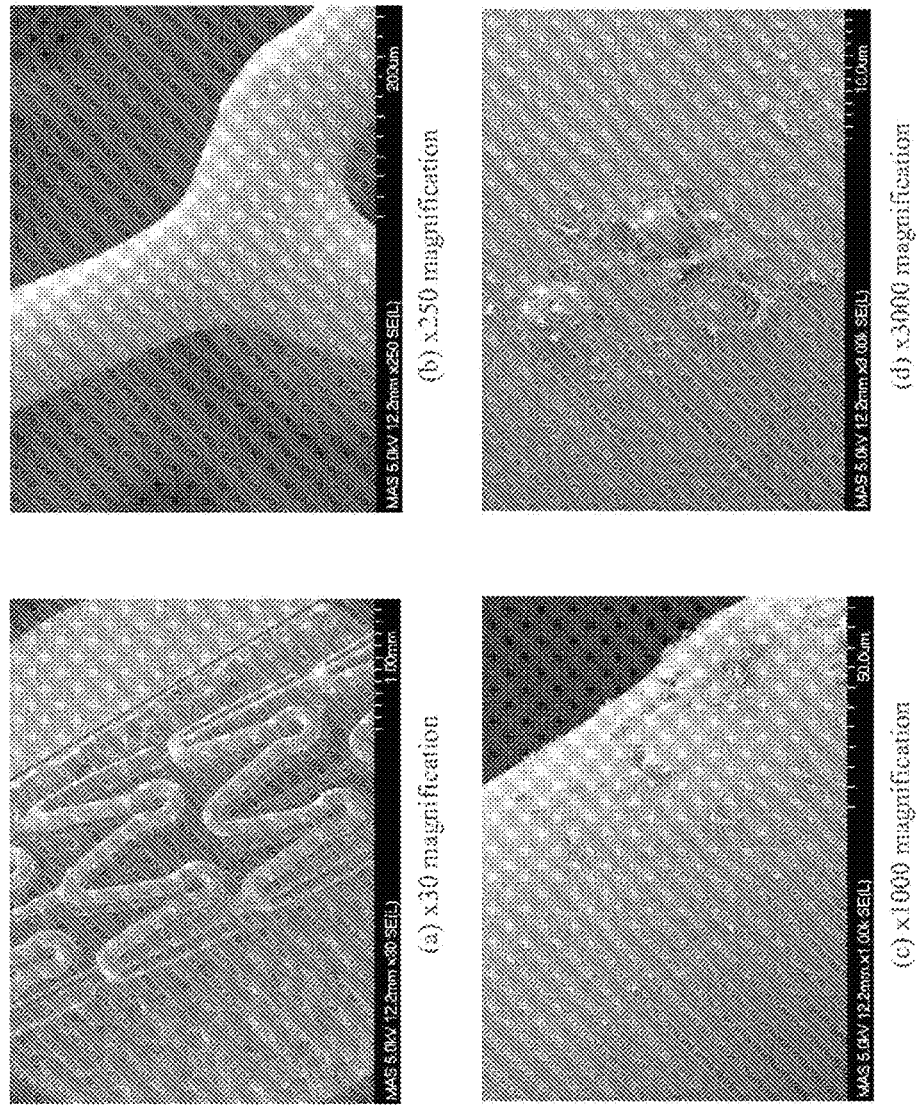
FIG. 7. Scanning Electron Microscope Images of Rapamycin/PEVA/PBMA Coated Stents, at (a) ×30 magnification, (b) ×250 magnification, (c) ×1000 magnification and (d) ×3000 magnification, as discussed in example 11.

Example 11. Scanning Electron Microscopy Analysis of Rapamycin/PEVA/PBM Coated Stents The stents produced in example 9 were examined by scanning electron microscopy, and the resulting images presented in FIGS. 7 at (a) ×30 magnification, (b) ×250 magnification, (c) ×1000 magnification and (d) ×3000 magnification. Clearly the nanoparticles have been sintered to an even and conformal film, with a surface topology of less than 5 microns, and demonstrate clear evidence of embedded crystalline rapamycin.

Figure 8:
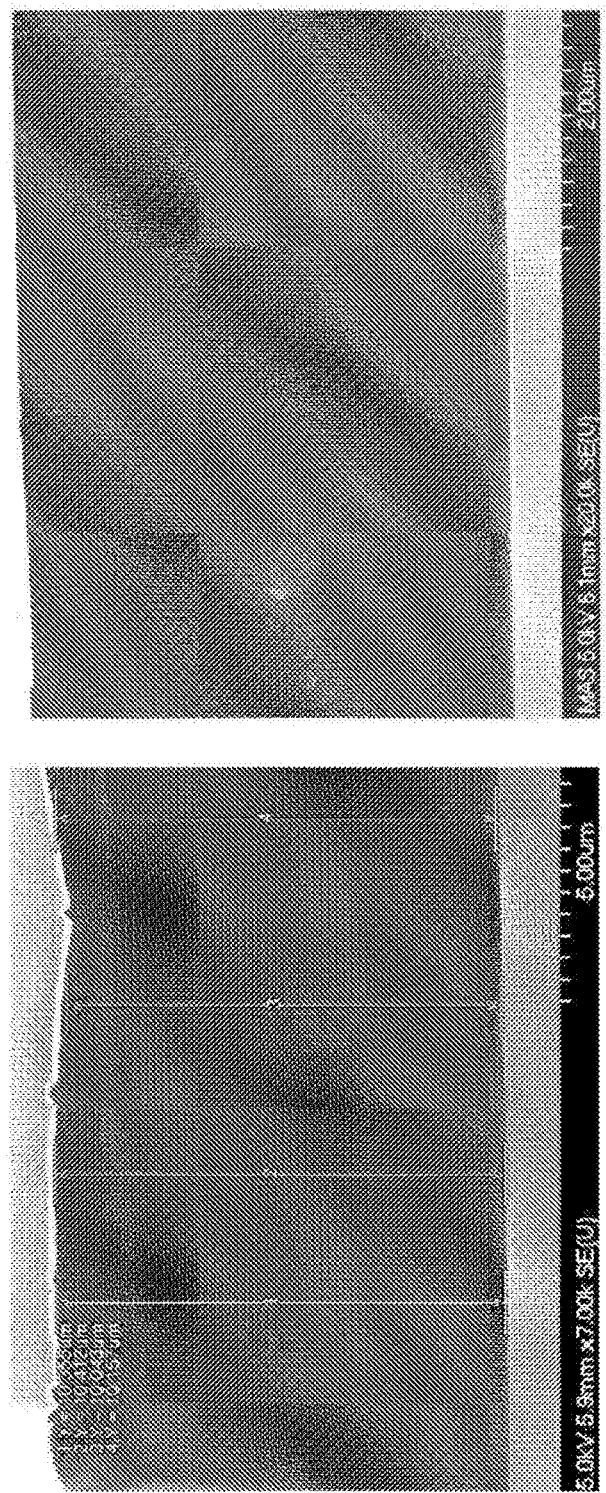
FIG. 8. Cross-sectional Scanning Electron Microscope Images of Rapamycin/PEVA/PBMA Coated Stents at (a) ×7000 magnification and (b) ×20000 magnification. Four cross-sectional thicknesses measured: (1) 10.355 µM; (2) 10.412 µM; (3) 10.043 µM and (4) 10.157 µM, providing a calculated average thickness of 10.242 µM±2%, also discussed in example 11.

Cross-sectional (FIB) images were also acquired and are shown in FIG. 8(a) at 7000× and (b) 20000× magnification. An even coating of consistent thickness is visible. Four cross-sectional thicknesses were measured: (1) 10.355 µM, (2) 10.412 µM, (3) 10.043 µM and (4) 10.157 µM, to give an average thickness of 10.242 µM, with only 2% (±0.2 µM) variation.

Figure 9:
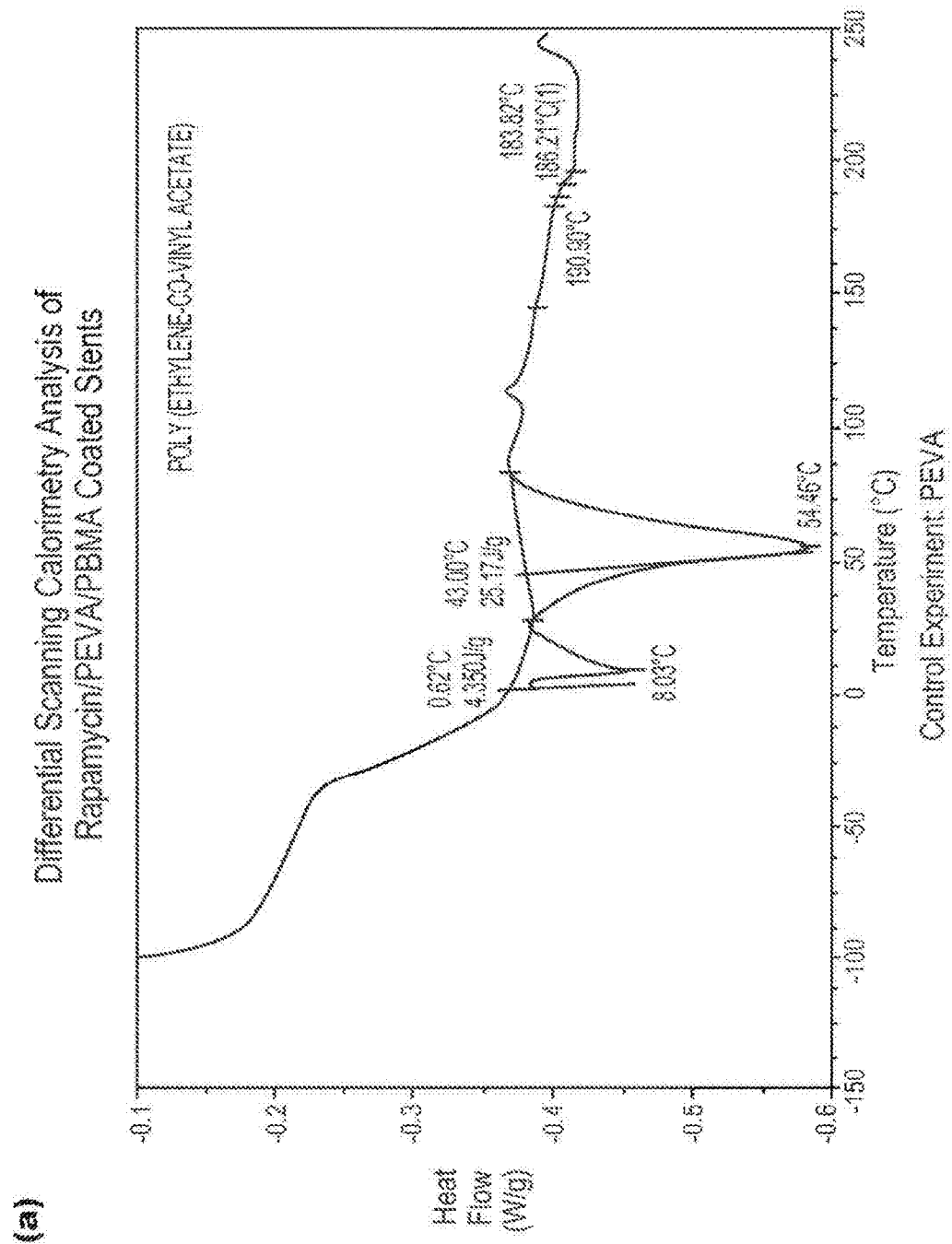
FIG. 9. Differential Scanning calorimetry (DSC) of (a) PEVA Control, (b) PBMA Control, (c) Rapamycin Control and (d) Coated Rapamycin, PEVA, PBMA Mixture. The Rapamycin crystalline melt at 185-200° C. is indicated in (c) and (d), as discussed in example 12.
Figure 9:
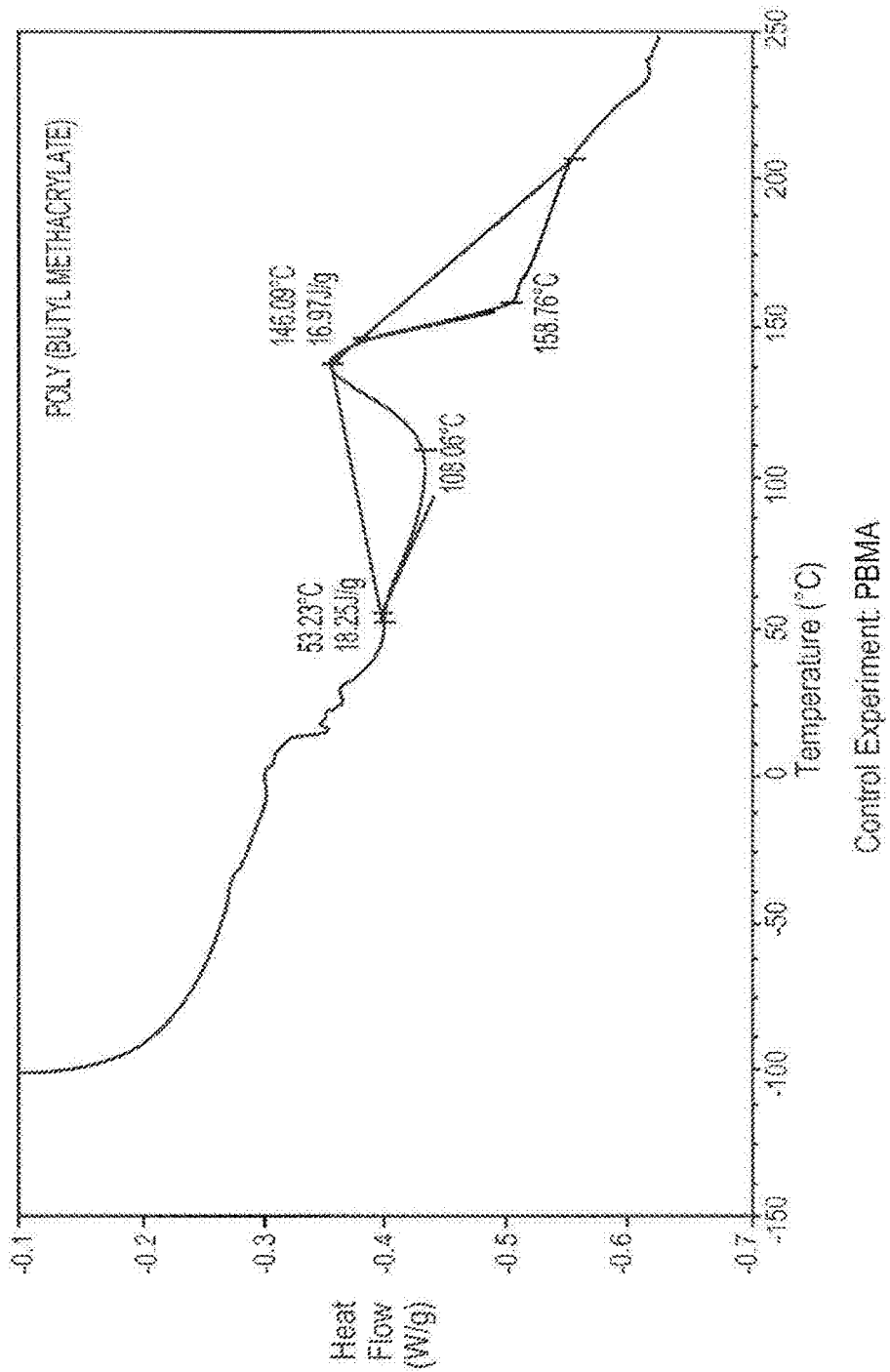
Figure 9:
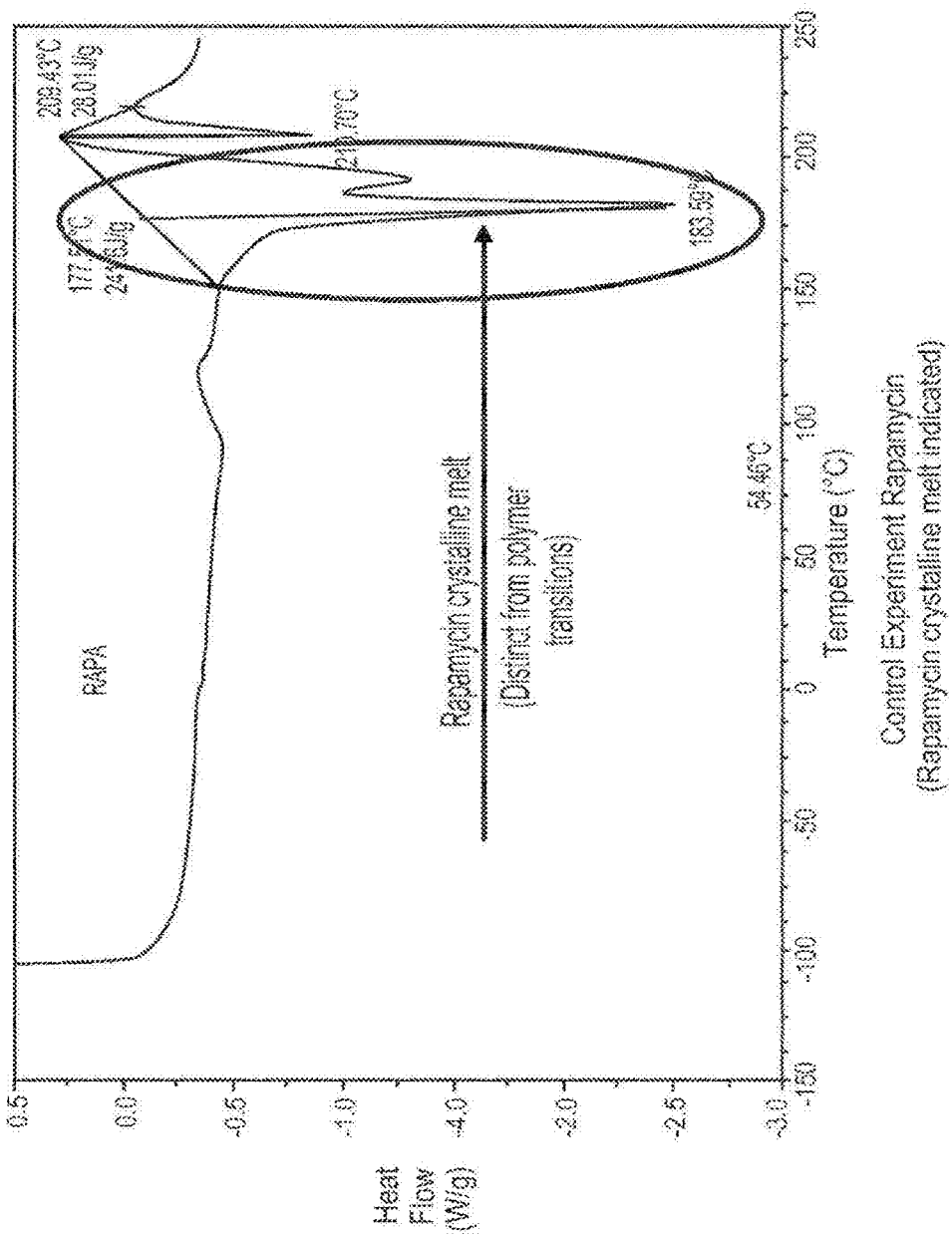
Figure 9:
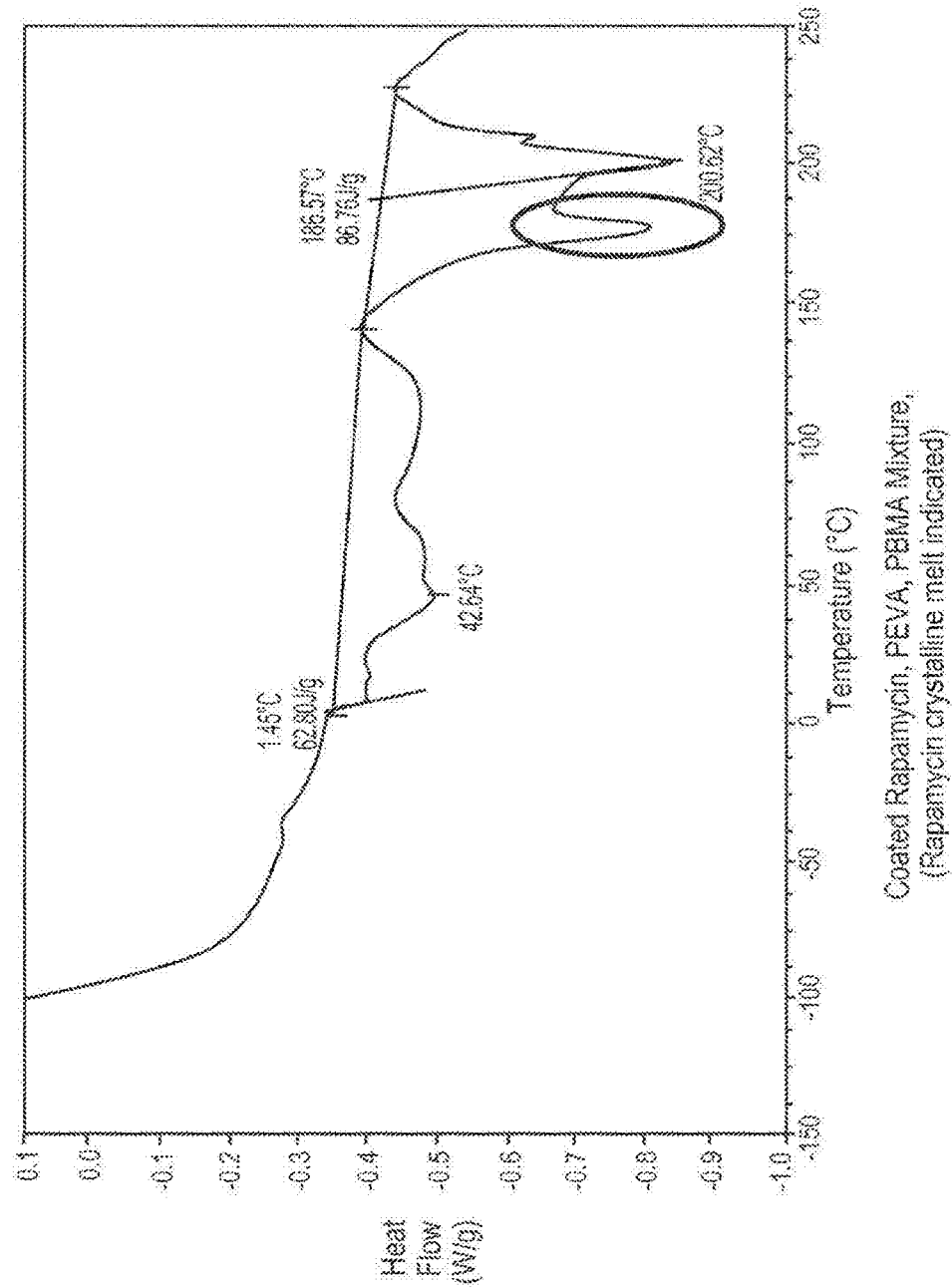

Example 12. Differential Scanning Calorimetry (DSC) of Rapamycin/PEVA/PBM Coated Stents The stents produced in example 9 were examined by Differential Scanning calorimetry (DSC). Control analyses s of PEVA only, PBMA only and Rapamycin only are shown in FIGS. 9 (a), (b) and (c) respectively. The DSC of the Rapamycin, PEVA and PBMA coated stent is shown in FIG.

9 (d). The rapamycin crystalline melt is clearly visible at 185-200° C. and distinct from those of the polymers.

Example 13. X-Ray Diffraction (XRD) of Rapamycin/PEVA/PBM Coated Stents

Figure 10:
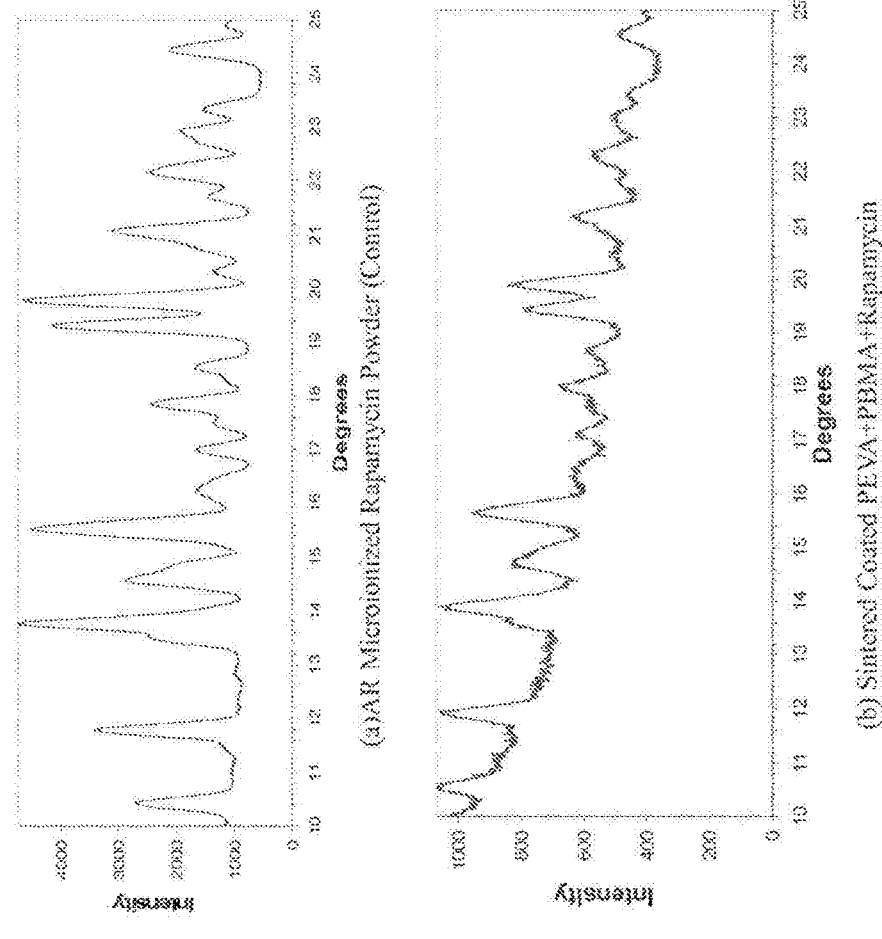
FIG. 10. X-Ray Diffraction of (a) Microionized Rapamycin Powder (Control) and (b) Coated Sintered Rapamycin/PEVA/PBMA Stents, as discussed in example 13.

The stents produced in example 9 were examined by X-Ray Diffraction (XRD). The control spectrum of micro-ionized Rapamycin powder is shown in FIG. 10 (a). The XRD of the Rapamycin, PEVA and PBMA coated, sintered stent is shown in FIG. 10 (b), showing that the Rapamycin remains crystalline (~64%) throughout the coating and sintering process.

Example 14. Confocal Raman Analysis of Rapamycin/PEVA/PBM Coated Stents

Figure 11:
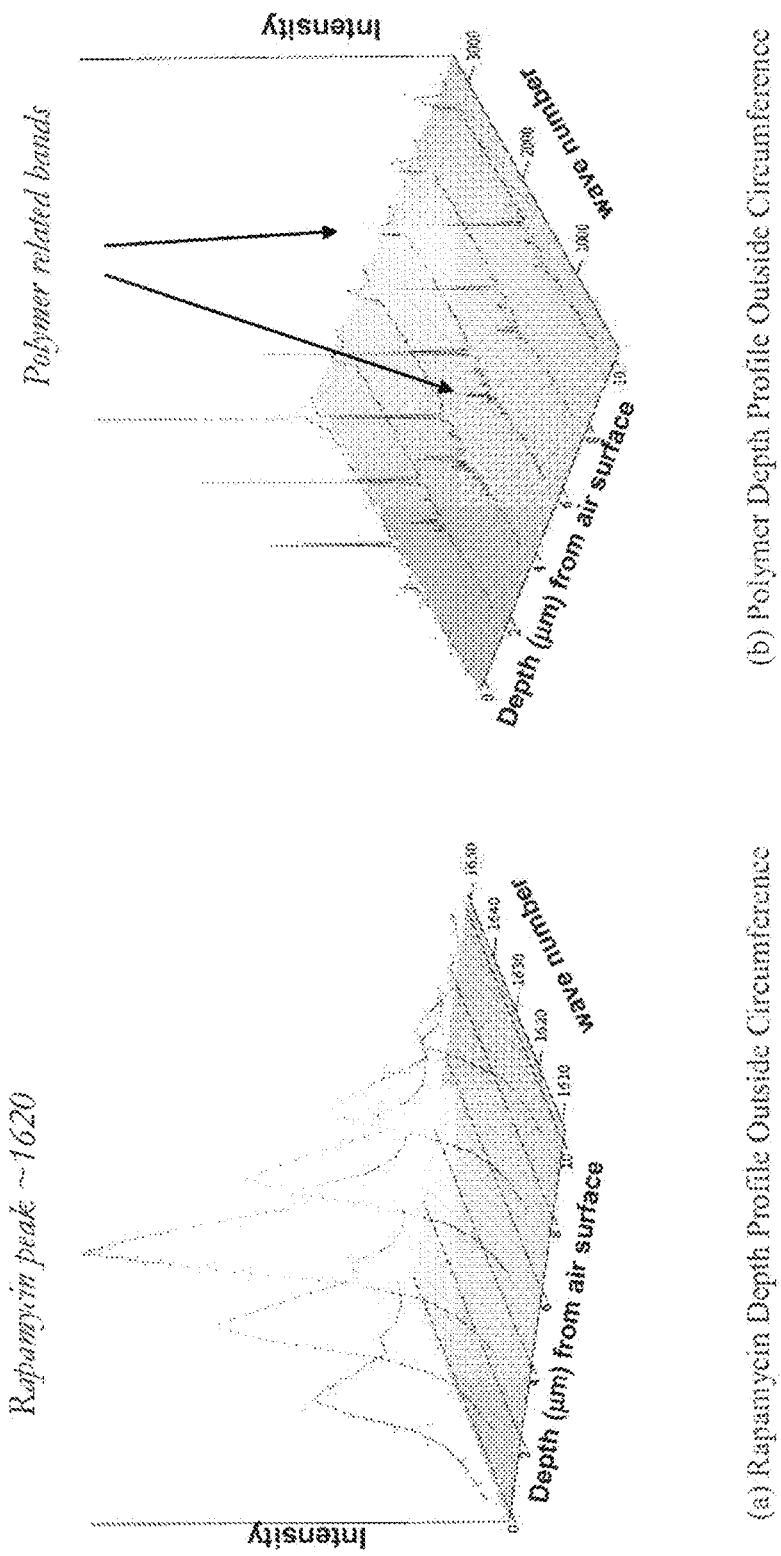
FIG. 11. Confocal Raman Analysis of Rapamycin/PEVA/PBMA Coated Stents (i.e. Depth Profiling from Coating Surface to Metal Stent), highlighting (a) Rapamycin Depth Profile Outside Circumference and (b) Polymer Depth Profile Outside Circumference, as discussed in example 14.

The stents produced in example 9 were examined by Confocal Raman Analysis, to provide depth profiling from the coating surface down to the metal stent. FIG. 11 (a) shows the Rapamycin depth profile outside circumference (Rapamycin peak at ~1620) and 11 (b) shows the polymer depth profile outside circumference, clearly demonstrating that the drug is distributed throughout polymer coated stents. The highest drug content appears in the center of the polymer coating (~4 µM from the air surface), which is controllable, via the coating and sintering conditions used. In certain embodiments of the invention, the drug would be close to the air surface of the coating. In other embodiments, the drug would be closer to the metal stent. In other embodiments, more than one drug would be deposited in the coating, wherein one drug would be closer to the air surface and another drug would be closer to the metal surface. In yet other embodiments, the drugs would be distributed together throughout the coating.

Figure 12:
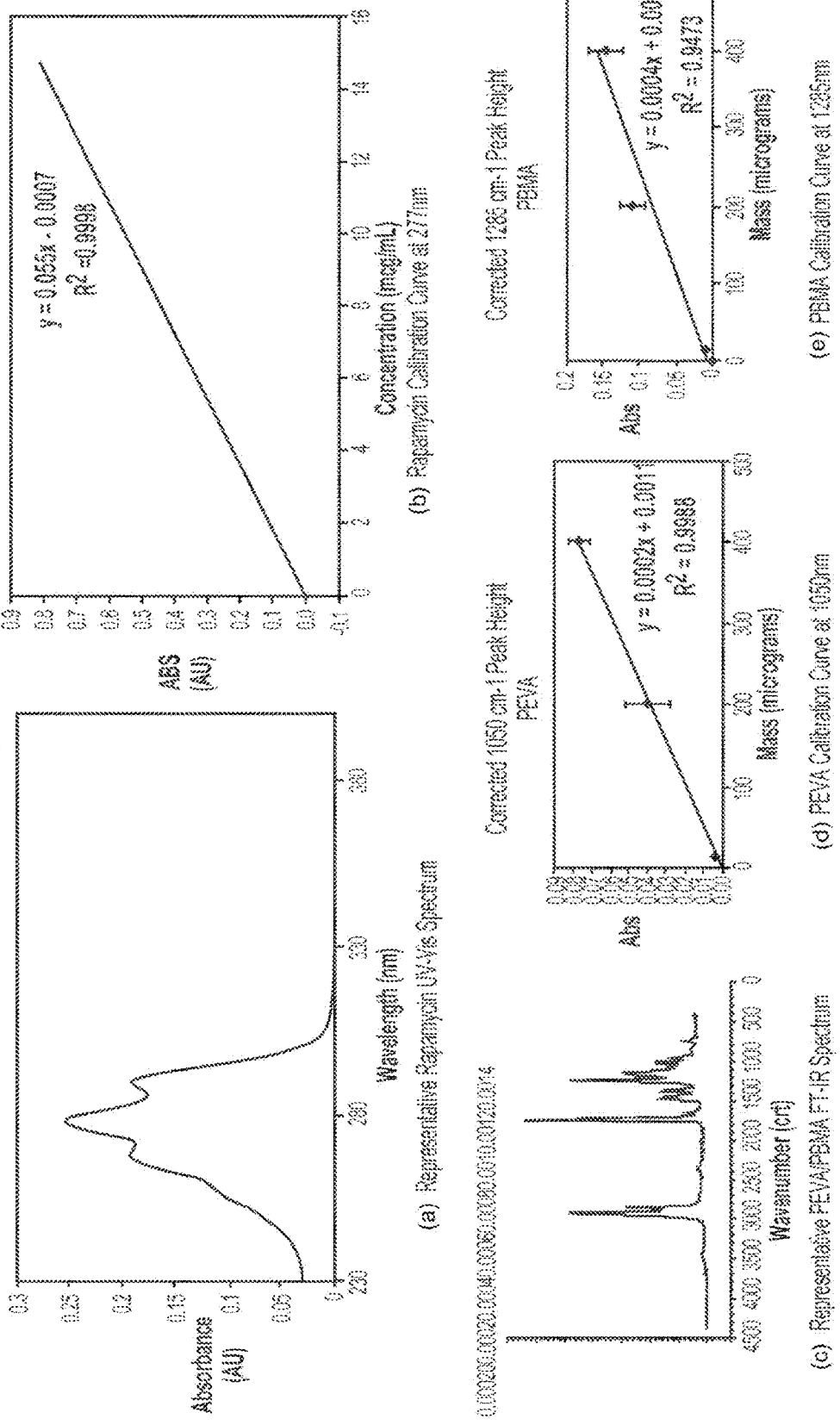
FIG. 12. (a) Rapamycin UV-Vis Spectrum and (b) Calibration Curve at 277 nm, (c) PEVA/PBMA FT-IR Spectrum, (d) PEVA Calibration Curve at 1050 nm and (e) PBMA Calibration Curve at 1285 nm.
Figure 13:
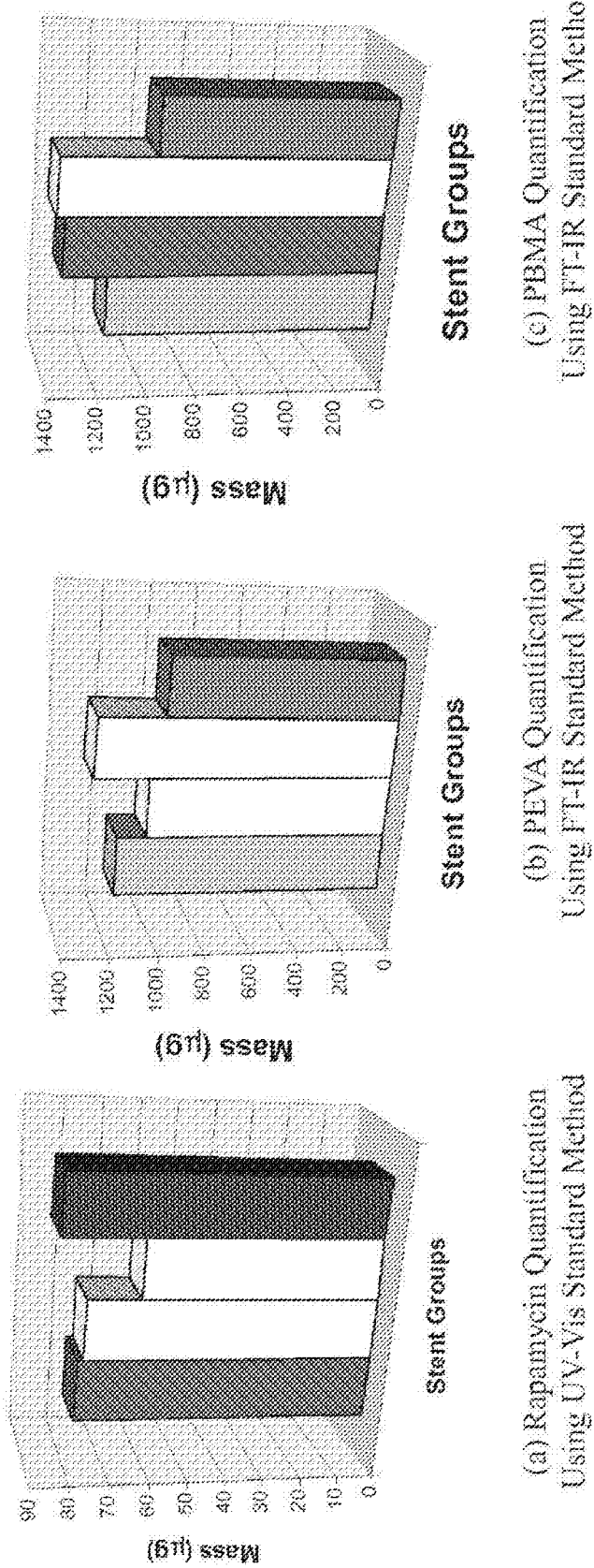
FIG. 13. Quantification of Coating Components, (mean concentrations (3 stents each); 4 cell by 8 mm parylene coated). (a) Rapamycin Quantification (74±11 µg) Using UV-Vis Method; (b) PEVA (1060±190 µg) and (c) PBMA (1110±198 µg) Quantification Using FT-IR Method, as discussed in example 15.

Example 15. UV-Vis and FT-IR Analysis of Rapamycin/PEVA/PBM Coated Stents for Quantification of Coating Components A UV-VIS method was developed and used to quantitatively determine the mass of rapamycin coated onto the stents with poly(ethylene-co-vinyl acetate) (PEVA) and poly(butyl methacrylate) (PBMA). The UV-Vis spectrum of Rapamycin is shown in FIG. 12 (a) and a Rapamycin calibration curve was obtained, $\lambda@$ 277 nm in ethanol, as shown in FIG. 12 (b). Rapamycin was dissolved from the coated stent in ethanol, and the drug concentration and mass calculated. An average mass of 74±11 µg Rapamycin was loaded onto the stents. The results in FIG. 13 (a) show a consistent drug coating: (+/−) 15% stent-to-stent, (+/−) 12% run-to-run, (mean concentrations (3 stents each); 4 cell by 8 mm parylene coated).

An FT-IR method was developed and used to quantitatively determine the mass of PEVA and PBMA coated onto stents with rapamycin. The FT-IR spectra of PEVA and PBMA is shown in FIG. 12 (c) and calibration curves were obtained using Beer's Law for PEVA $\lambda@$~1050 cm$^{-1}$ and PBMA $\lambda@$~1285 cm$^{-1}$, as shown in FIGS. 12(d) and (e), respectively. The polymers were dissolved from the coated stent in methylene chloride, and the polymer concentrations and the masses calculated accordingly. An average mass of 1060±190 µg PEVA and 1110±198 µg PBMA was loaded onto the stents. The results in FIGS. 13 (b) and (c) show a consistent polymer coating: (+/−) 18% stent-to-stent, (+/−) 15% run-to-run, (mean concentrations (3 stents each); 4 cell by 8 mm parylene coated).

Figure 14:
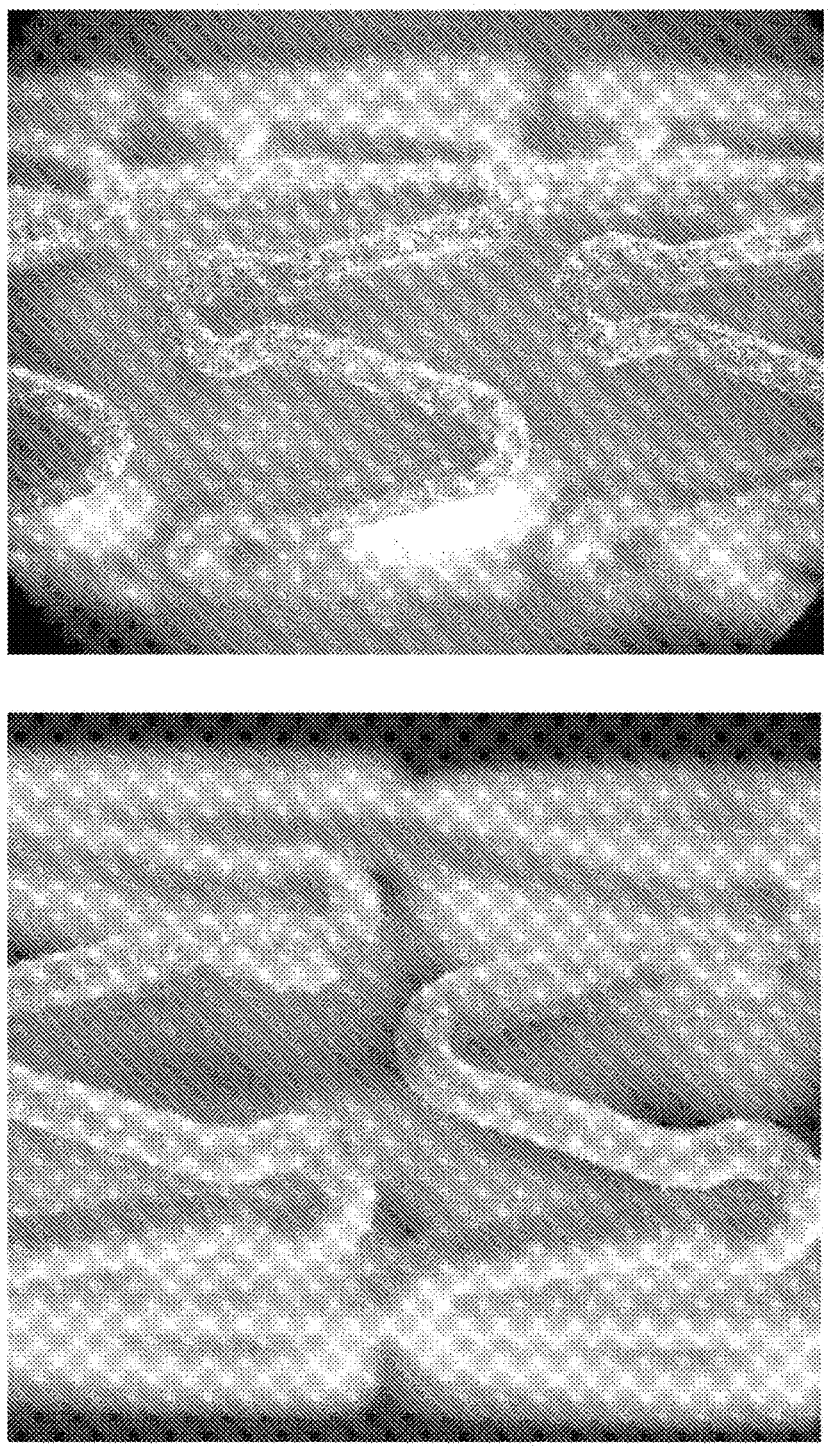
FIG. 14. Optical Microscopy Showing the Outside Surface of a 3 mm Guidant TriStar® Stent Coated with Paclitaxel-polymer composite, as discussed in example 16.
Figure 15:
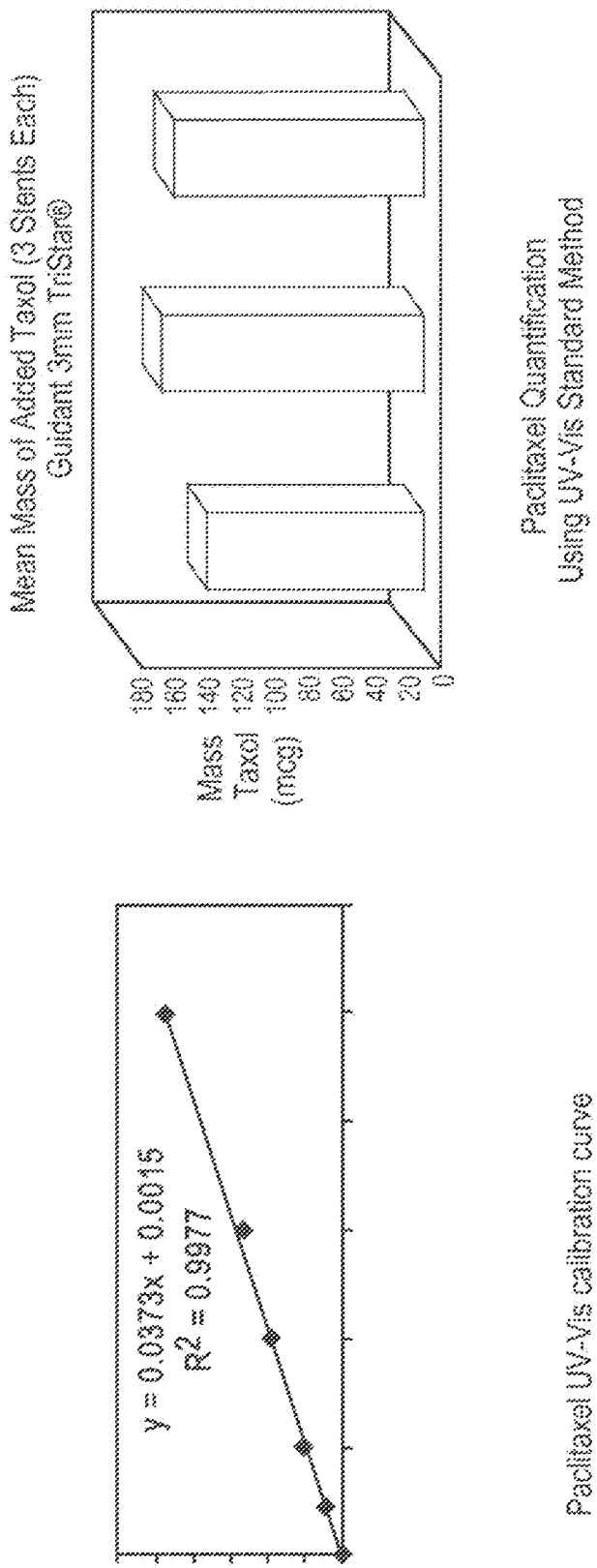
FIG. 15. Paclitaxel Quantification After Coating on a 3 mm Guidant TriStar® Stent with Paclitaxel/PEVA/PMBA composite, as discussed in example 16. (a) Calibration Curve at 228 nm in ethanol Using UV-Vis Standard Method and (b) Quantification (148±14 µg) Using UV-Vis Method FIG. 16. Quantification of Coating Components, (mean concentrations (3 stents each); 6 cell by 8 mm parylene coated). (a) Rapamycin Quantification (81±3 µg) Using UV-Vis Method; (b) PEVA (391±69 µg) and (c) PBMA (268±64 µg) Quantification Using FT-IR Method, as discussed in example 17.

Example 16. Coating of Stents with Paclitaxel/PEVA/PMBA 3 mm Guidant TriStar® Stents were coated with a Paclitaxel/PEVA/PMBA composite, by processes of the invention, as described herein. The coated stents were examined by optical microscopy, and photos of the outside surface of the stent (a) prior to sintering and (b) after sintering are shown in FIG. 14. FIG. 15 (a) represents the UV-Vis calibration curve developed for Paclitaxel, $\lambda@$228 nm in ethanol, using the methods of example 15, as described above. Rapamycin was dissolved from the coated stent in ethanol, and the drug concentration and mass calculated, to give an average mass of 148±14 µg loaded Rapamycin, as shown in FIG. 15 (b).

Figure 16:
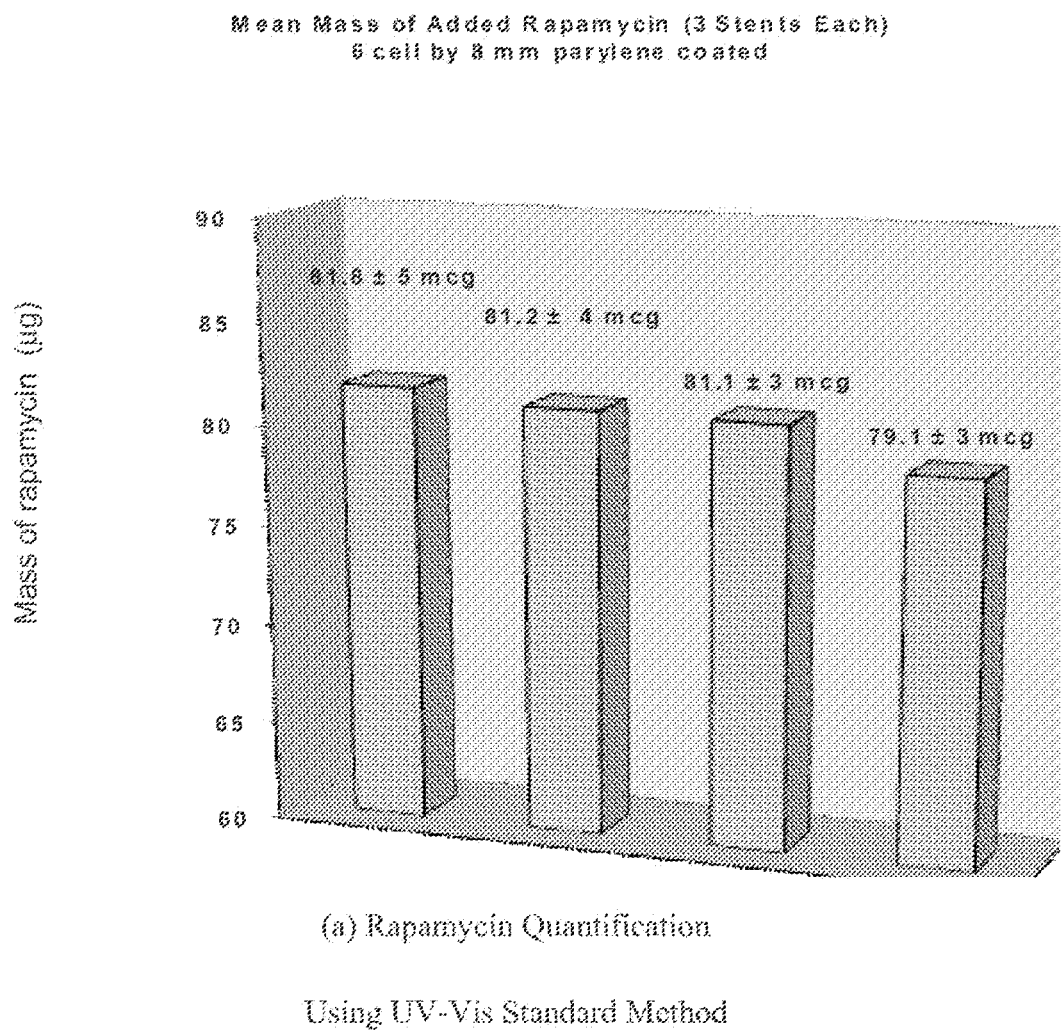
Figure 16:
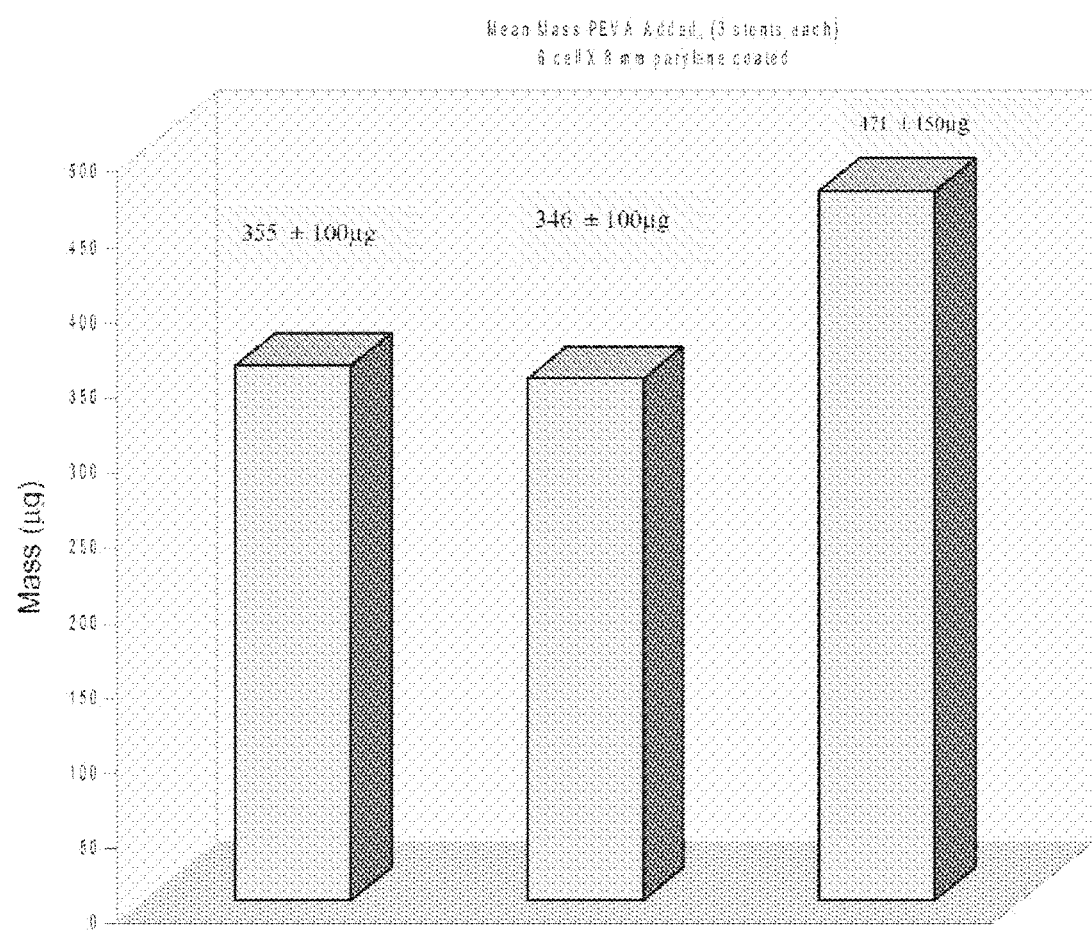
Figure 16:
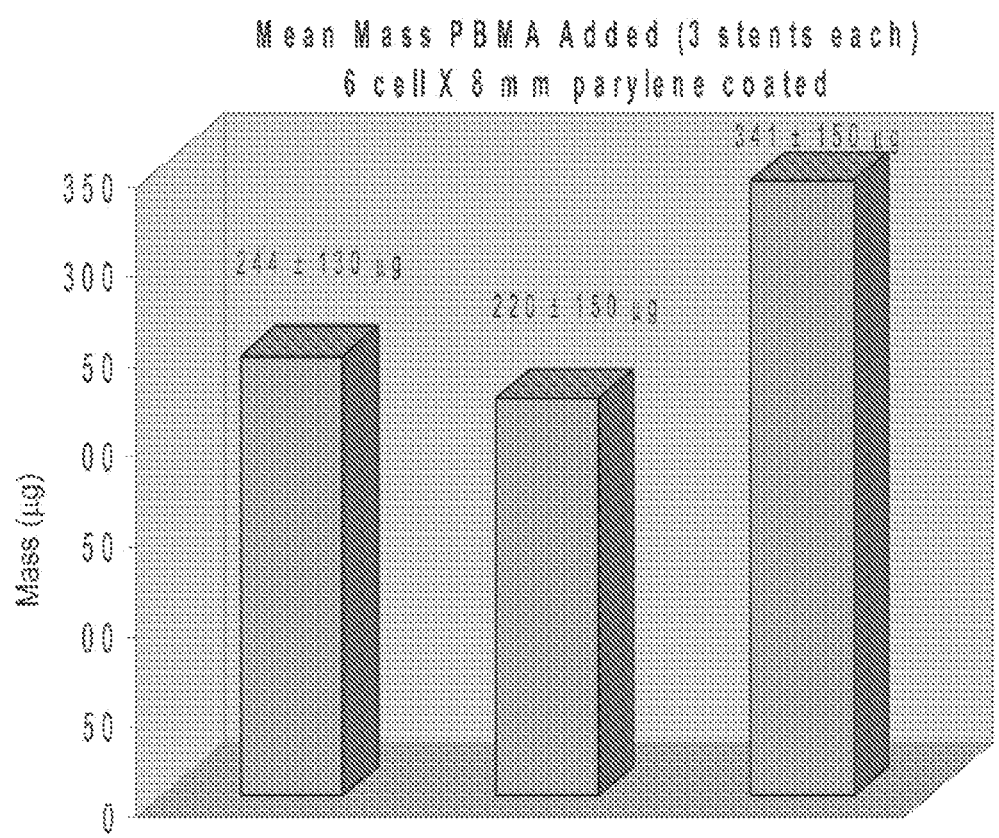
Figure 17:
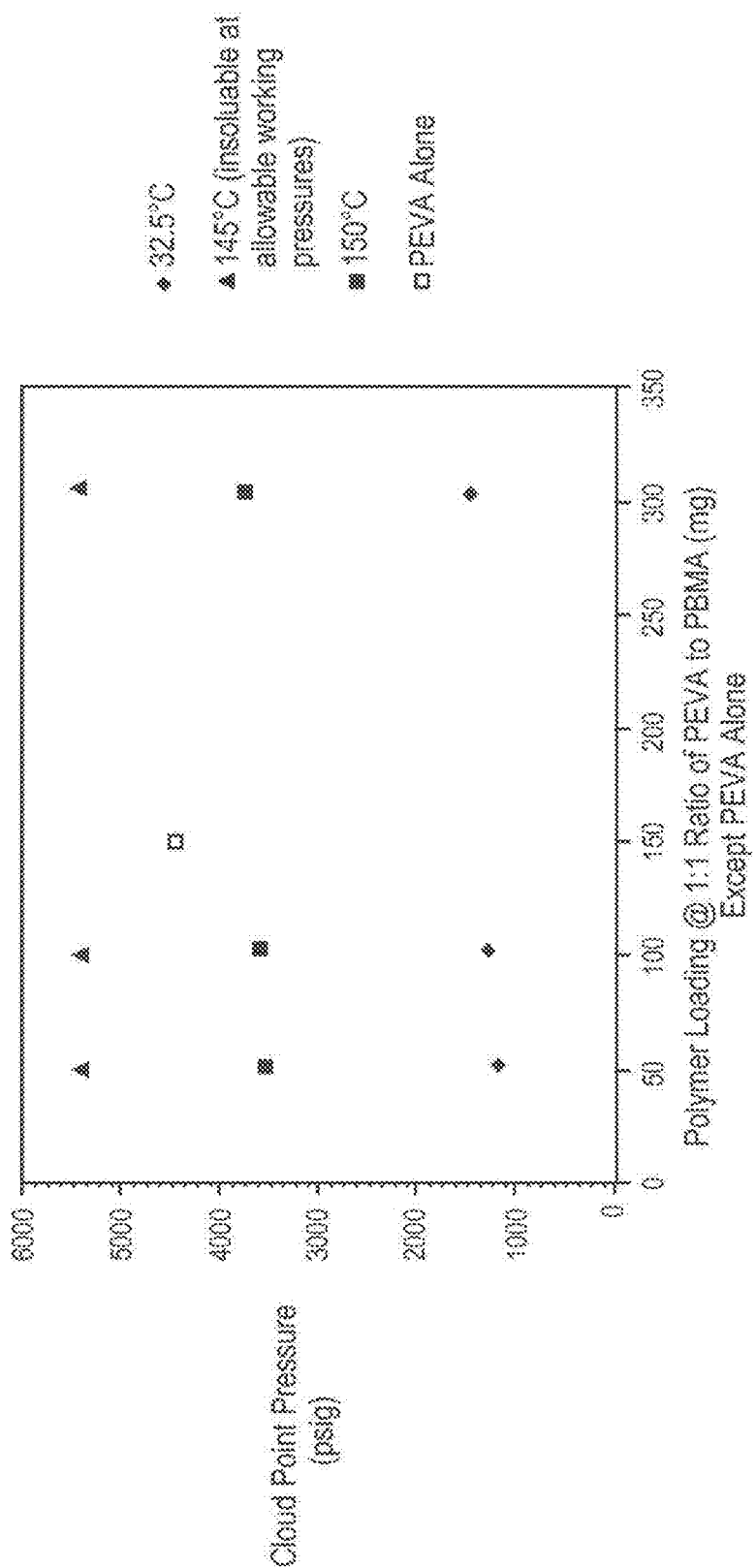
FIG. 17. Cloud point isotherms for polyethylene-co-vinyl acetate (PEVA) and poly(butyl methacrylate) (PMBA) combined as discussed in examples 19, 20, 21 and 22.
Figure 18:
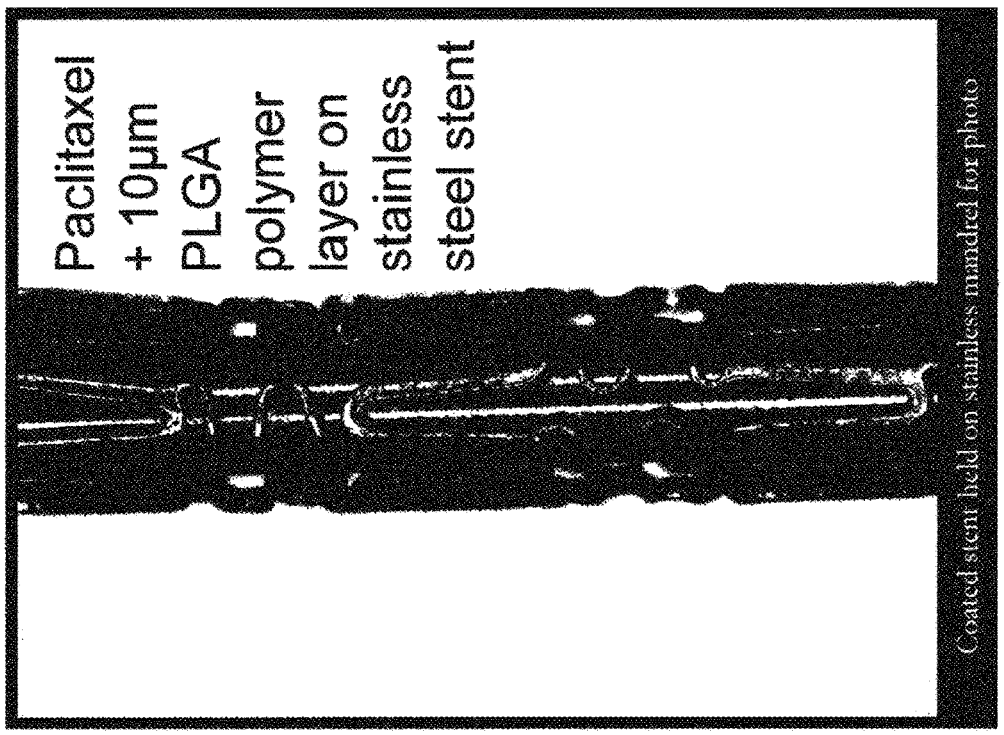
Figure 20:
Figure 21:
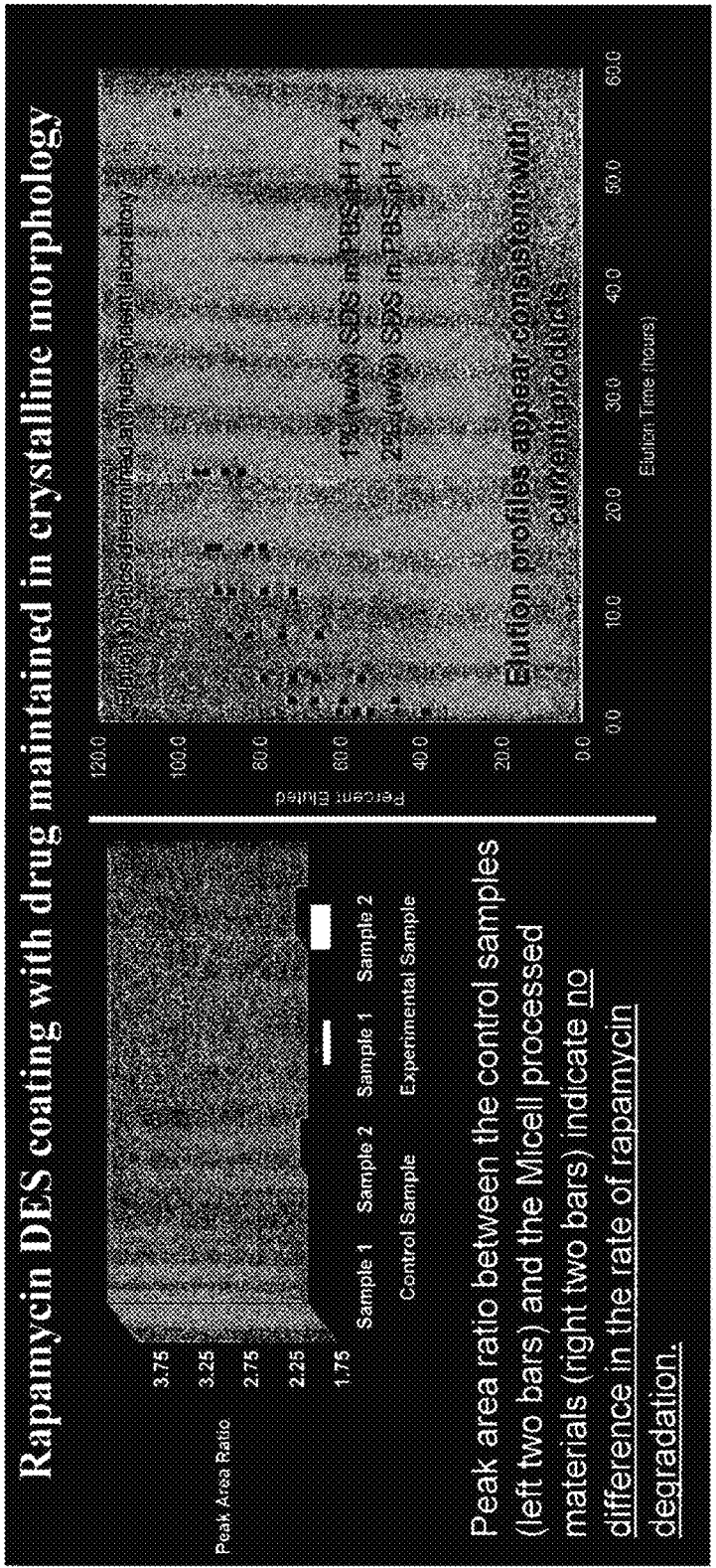
Figure 22:
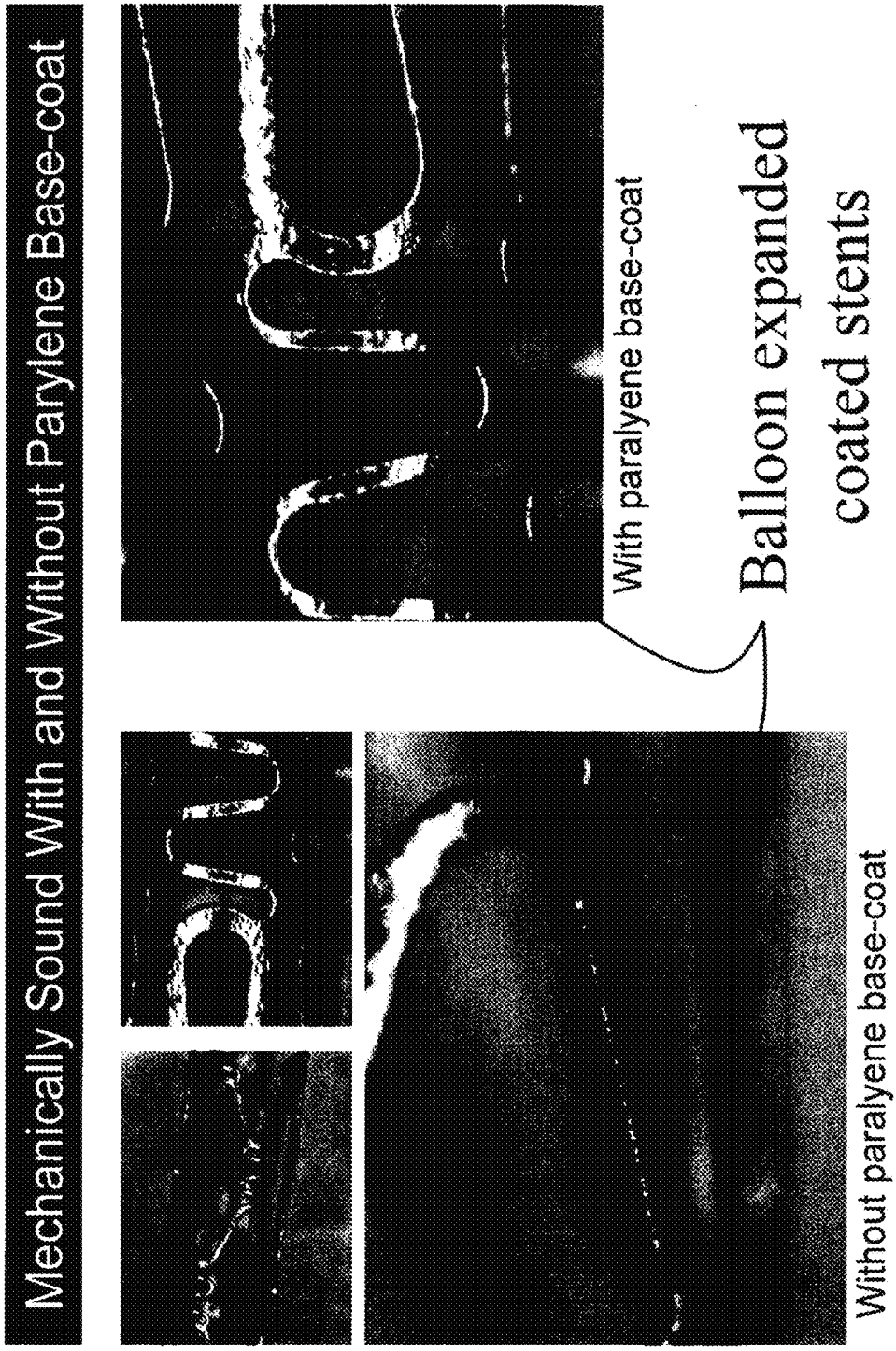
Figure 23:
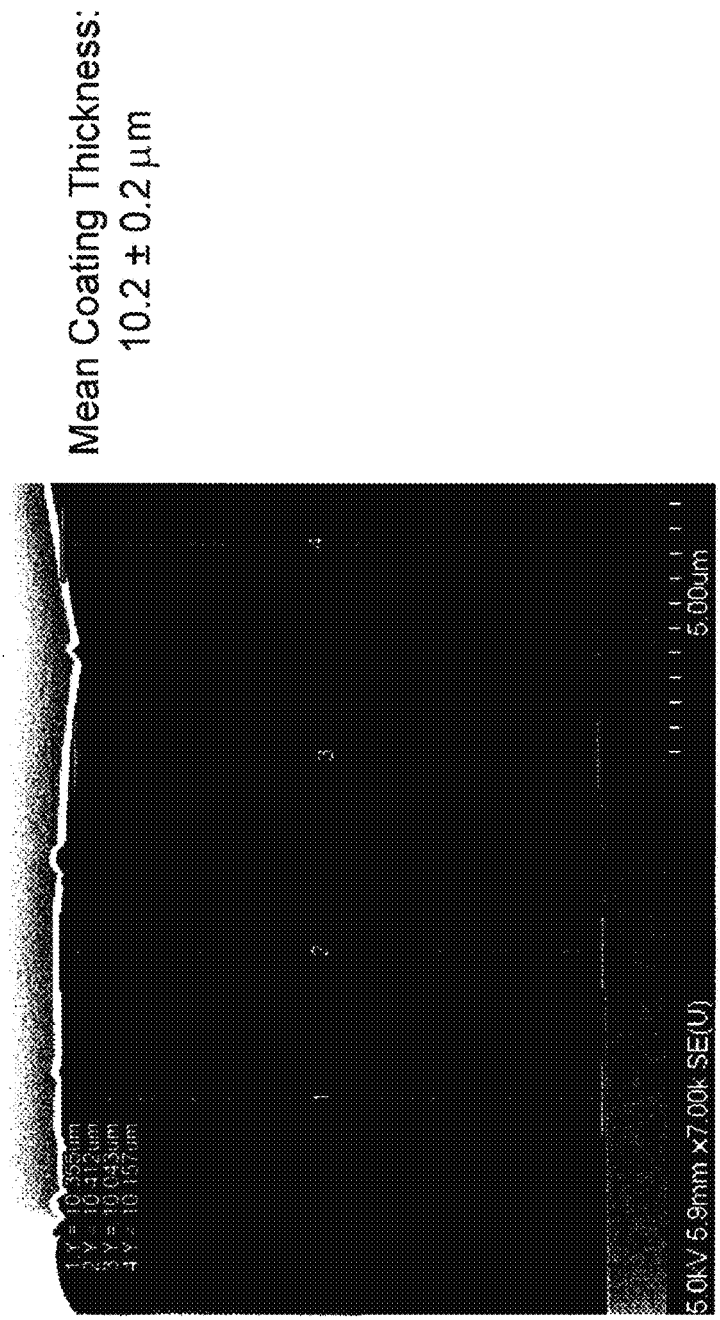

Example 17. UV-Vis and FT-IR Analysis of Rapamycin/PEVA/PBM Coated Stents for Quantification of Coating Components The UV-VIS and FT-IR methods, described in example 15, were used to determine the quantities of Rapamycin, PEVA and PBMA respectively, from stents coated with Rapamycin, PEVA and PBMA by processes of the invention, as described herein. The component quantifications are shown in FIG. 16 and calculated; (a) an average mass of 81±3 µg Rapamycin was loaded onto the stents, (b) an average mass of 391±69 µg PEVA and (c) 268±64 µg PBMA was loaded onto the stents.

Example 18. Coating of Stents with Rapamycin or Paclitaxel, Polyethylene-Co-Vinyl Acetate (PEVA) and Polybutyl Methacrylate (PBMA)

A 25 mL stainless steel reservoir is charged with 150.0±0.1 mg of poly(ethylene co-vinyl acetate) (PEVA) and 150.0±0.1 mg of poly(butyl methacrylate) (PBMA) to which is transferred 20.0±0.3 grams of dichlorofluoromethane. The pressure rises in the reservoir to approximately 28 psig. The reservoir is heated to 60° C. after transferring dichlorofluoromethane to the reservoir. The reservoir is then pressurized with helium until the pressure reaches 700±30 psig. Helium acts as a piston to push out the dichlorofluoromethane-polymer solution. The reservoir is isolated from the system by appropriate valving. A second stainless steel reservoir with volume of 15±1 mL is charged with 13 mg of drug compound (rapamycin or Paclitaxel). This reservoir is pressurized to 400±5 psig with carbon dioxide gas. The temperature of the drug reservoir is room temperature. The reservoir is isolated from the system by appropriate valving. A third reservoir is charged with tetrahydrofuran or dichloromethane solvent so that the polymer nozzle can be flushed between polymer sprays. This reservoir is also pressurized with helium to 700 psig and isolated from the system by appropriate valving. The polymer spray nozzle is heated to 120±2° C. while the drug spray nozzle remains at room temperature. Stents are loaded into the stent fixture and attached to a high voltage source via an alligator clamp. The alligator clamp enters the coating chamber via an electrically insulated pass through. Carbon dioxide gas is admitted into the coating vessel at 8 psig for a period of 5 minutes through a third gas flush nozzle to remove air and moisture to eliminate arcing between the nozzles and components held at high potential. After flushing the coating chamber with carbon dioxide gas, a potential of 35 kV is applied to the stents via a high voltage generator. This potential is maintained during each coating step of polymer and drug. The potential is removed when the polymer spray nozzle is flushed with tetrahydrofuran or dichloromethane. Polymer solution is sprayed for 7 secs from the polymer solution reservoir into the coating chamber. The applied potential is turned off and the polymer nozzle is removed from the coating chamber and flushed with solvent for 2 minutes and then flushed with helium gas for approximately one minute until all solvent is removed from the nozzle. The coating chamber is flushed with carbon dioxide gas during the nozzle solvent flush to flush out dichlorofluoromethane gas. The polymer spray nozzle is placed back in the coating chamber and the carbon dioxide gas flush is stopped. A 35 kV potential is applied to the stents and the drug compound is rapidly sprayed into the coating chamber by opening appropriate valving. After one minute of rest time, polymer spray commences for another seven seconds. The process can be repeated with any number of cycles.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The various analytical methods developed to examine the coated stents and the results they generated are summarized in the table below:

Example 19. Preparation of Supercritical Solution Comprising, Polyethylene-Co-Vinyl Acetate (PEVA) and Polybutyl Methacrylate (PBMA) in Isobutylene 75 mg of PEVA and 75 mg of PBMA are placed in a 25 mL view cell. The view cell is heated to 150° C.

Isobutylene is added to a pressure of 3000 psig. Under these conditions, a clear solution is produced.

Example 20. Preparation of Supercritical Solution Comprising Polyethylene-Co-Vinyl Acetate (PEVA) and Polybutyl Methacrylate (PBMA) in Isobutylene 150 mg of PEVA and 150 mg of PBMA are placed in a 25 mL view cell. The view cell is heated to 150° C.

Isobutylene is added to a pressure of 4000 psig. Under these conditions, a clear solution is produced.

Example 21. Preparation of Supercritical Solution Comprising Polyethylene-Co-Vinyl Acetate (PEVA) and Polybutyl Methacrylate (PBMA) in Isobutylene and $CO_2$ 75 mg of PEVA and 75 mg of PBMA are placed in a 25 mL view cell and the cell is heated to 150° C.

Isobutylene is added to a pressure of 4000 psig, to produce a clear solution.

10 (v/v %) CO2 is added. The addition of $CO_2$ at this volume percent does not precipitate the dissolved polymer.

| Analytical Method | To Provide | Result |
| --- | --- | --- |
| Optical microscope | Visible images of the stents. Empirical survey of coating uniformity | Nanoparticles deposited evenly on all surfaces of stent Sintering to conformal film (with visual evidence of crystalline drug) |
| SEM | Top-down and cross-sectional images (electron micrographs) at various magnifications. Gross estimates of coating uniformity and thickness | Very smooth and conformal films at high magnification 10.2 ± 0.3 μm well-sintered films via cross-sectional analysis |
| X-ray diffraction (XRD) | Quantitative indication of drug morphology in coated films on proxy substrates | +65% crystalline rapamycin on proxy samples |
| Differential Scanning Calorimetry (DSC) | Qualitative evidence of crystalline rapamycin from proxy substrates (crystalline melt) | Demonstrated rapamycin crystalline melt (185-200° C.) |
| Confocal Raman | Compositional data (drug, polymer A, Polymer B) at various depths in the film on the coated stents (i.e. surface, 2 μm deep, 4-μm deep, etc.) | Drug distributed throughout polymer coated stents |
| UV-Vis Spectroscopy | Quantitative compositional information for drug loading on 'sacrificial' coated stents, BL method | 74 ± 11 μg drug loaded onto stents, run-to-run control within 12% deviation |
| FT-IR spectroscopy | Quantitative compositional information for loading of both polymers on 'sacrificial' coated stents, BL method | 1060 ± 190 μg PEVA loaded onto stents 1110 ± 198 μg PBMA loaded onto stents |

Example 22. Preparation of Supercritical Solution Comprising Polyethylene-Co-Vinyl Acetate (PEVA) and Polybutyl Methacrylate (PBMA) in Isobutylene and $CO_2$ 150 mg of PEVA and 150 mg of PBMA are placed in a 25 mL view cell and the cell is heated to 150° C.

Isobutylene is added to a pressure of 4000 psig, to produce a clear solution.

10 (v/v %) CO2 is added. The addition of CO2 at this volume percent does not precipitate the dissolved polymer; however addition of $CO_2$ at higher volume fraction leads to polymer precipitation, under these conditions.

Example 23

This example illustrates how the present invention provides a method for optimal design of therapeutic profiles using both anti-restenosis and anti-thrombotic compounds to address both short and long-term safety of drug-eluting stents. This approach which includes multi-drug formulations in biodegradable polymers has the potential to provide improved benefits for both patients and clinicians. The example illustrates an embodiment of the invention to deliver drug-eluting stents by maintaining morphology of therapeutic compounds and providing manufacturing processes that apply discrete and independent therapies within a single, multi-therapy coating under these conditions.

As discussed above, many processes for spray coating stents require that drug and polymer be dissolved in solvent or mutual solvent before spray coating can occur. The present invention provides a method to spray coat stents with drug(s) and polymer(s) in independent steps under conditions that do not require dissolved drug and separates drug and polymer spraying into individual steps. This capability allows discrete placement of drug within a polymer matrix and makes possible placing more than one drug on a single medical device with or without an intervening polymer layer. Discrete deposition and elution of a dual drug coated drug eluting stent using the present invention is summarized below.

Methods: Taxol (98% purity) was purchased from Toronto Research Chemicals. Heparin was purchased from Polysciences, Inc. Polyethylene-co-vinyl acetate (33% w/w vinyl acetate) and Polybutylmethacrylate were purchased from Sigma-Aldrich and used without further purification. All solvents unless otherwise noted were supplied by Sigma-Aldrich and were spectrophotometric grade and used without further purification. Three stents manufactured to requested specifications (Burpee Materials Technology, L.L.C.) were coated simultaneously. Polymer was applied to stents using an electrostatic rapid expansion of a supercritical solution method (RESS) as described above while Heparin and Taxol were applied to stents using a dry powder coating method also described above. Heparin was deposited prior to depositing Taxol with an intervening polymer layer. Heparin was analyzed by UV-Vis spectrophotometry (Ocean Optics) and quantified using the Beer-Lambert relationship using an Azure A assay while Taxol was determined directly from the elution medium at 227 nm. Coated stents were removed from the coating chamber and sintered at 30° C. and approximately 4 bar using the sintering method described above. Taxol drug elution from the polymer matrix was completed by eluting stents in phosphate buffered saline at pH 7.4 with added tween 20 (0.05% w/w) in a thermostatically controlled temperature bath held at 37° C. An aqueous media was used to elute heparin from the polymer matrix. Because of surfactant interference with the azure A assay, heparin elution was quantitatively determined separately from Taxol.

Figure 24:
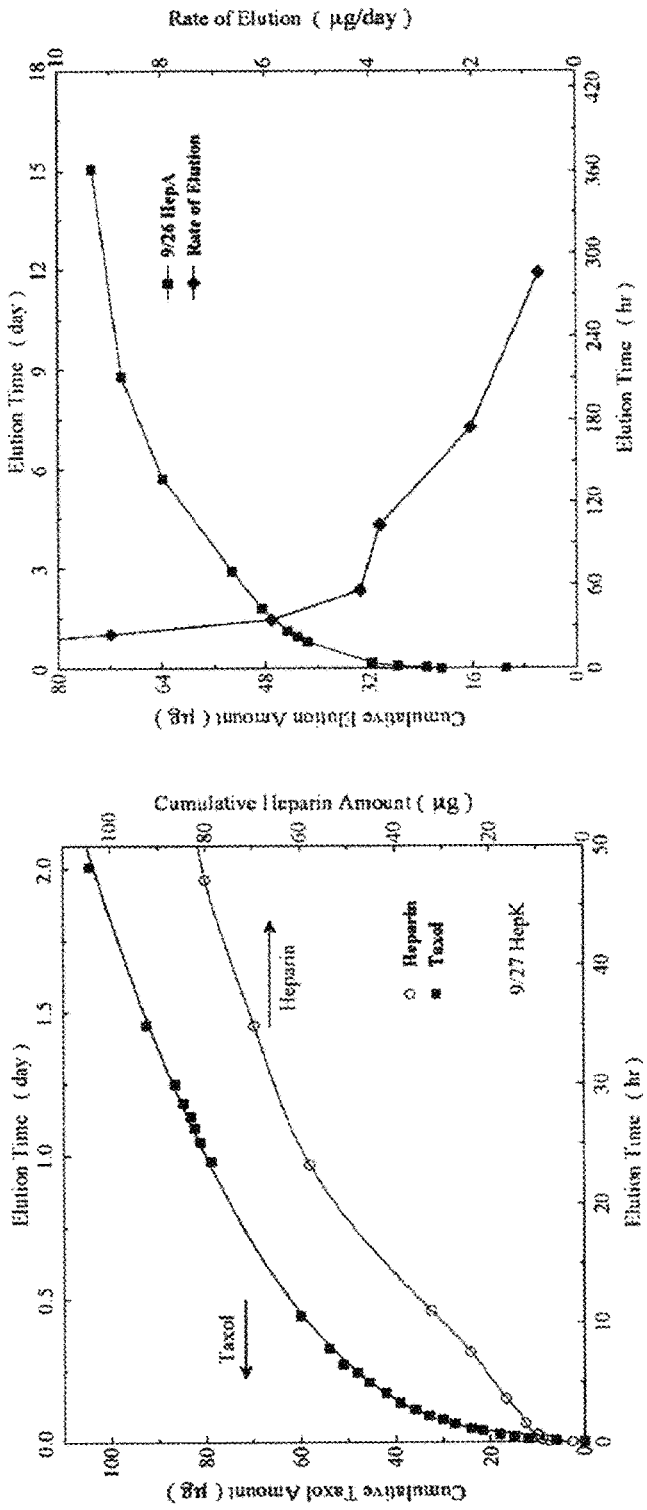

Results: Heparin was loaded on the stent at 70 micrograms and Taxol was loaded on the stent at 78 micrograms. The total polymer mass deposited on the stent was 2.1 milligrams. Heparin and Taxol elution was monitored for 15 days. FIG. 24 shows the cumulative mass of heparin eluted as well as the elution rate. The ability of azure A to continue to bind to heparin suggests that no chemical reaction between heparin and Taxol occurs.

In summary, in certain embodiments, the present invention provides a method for coating drug-eluting stents. Polymer(s) and drug(s) are applied in a controlled, low-temperature, solvent-free process. In one embodiment Rapamycin, PBMA and PEVA are applied to provide a conformal, consistent coating at target Rapamycin loading, in a 1:1 mixture of PBMA:PEVA, at a thickness of ~1004, containing zero residual solvent. The Rapamycin is deposited in crystalline morphology (+50%). The Rapamycin/PEVA/PBMA film is applied using a dry process, wherein the drug and polymer content is highly controllable, and easily adaptable for different drugs, different (resorbable and permanent) polymers, multiple drugs on a single stent, and provides for a high degree of stent-to-stent precision. The absence of traditional solvents during deposition enables control over drug content at variable film depths.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for depositing a coating on a substrate, comprising the steps of:
   a. providing a substrate;
   b. depositing at least one polymer layer onto said substrate;
   c. depositing at least one pharmaceutical layer comprising a pharmaceutical agent onto said substrate without use of a solvent; and
   d. sintering said at least one polymer layer so as to produce a polymer film adhered to said substrate under conditions that do not substantially modify a morphology of said pharmaceutical agent, wherein said pharmaceutical agent comprises a morphology that is crystalline or semi-crystalline.

2. The method of claim 1, wherein said at least one polymer layers comprises a bioabsorbable polymer.

3. The method of claim 1, wherein said at least one polymer layer is selected from PLA, PLGA, PGA and Poly(dioxanone).

4. The method of claim 1 comprising depositing 3 or more layers as follows:
   a first polymer layer;
   the first polymer layer comprising said pharmaceutical agent which is a first pharmaceutical agent;
   a second polymer layer;
   the second polymer layer comprising a second pharmaceutical agent; and
   a third polymer layer.

5. The method of claim 1 comprising depositing 4 or more layers as follows:
- a first polymer layer;
- a first pharmaceutical layer comprising a first pharmaceutical agent;
- a second polymer layer; and
- a second pharmaceutical layer comprising a second pharmaceutical agent.

6. The method of claim 1 comprising depositing 4 or more layers as follows:
- a first pharmaceutical layer comprising a first pharmaceutical agent;
- a first polymer layer;
- a second pharmaceutical layer comprising a second pharmaceutical agent; and
- a second polymer layer.

7. The method of claim 1 comprising depositing 3 or more layers as follows:
- a first pharmaceutical layer comprising a first pharmaceutical agent;
- a polymer layer; and
- a second pharmaceutical layer comprising a second pharmaceutical agent.

8. The method of claim 1 wherein depositing the at least one polymer layer and depositing the at least one pharmaceutical layer comprises alternating layers of the pharmaceutical layer, or the polymer layer including the pharmaceutical agent, and the polymer layer without the pharmaceutical agent.

9. The method of claim 8, wherein the pharmaceutical agent layers are substantially free of polymer and the polymer layers are substantially free of pharmaceutical agent.

10. The method of claim 1, comprising depositing 5, 10, 20, 50, or 100 layers.

11. The method of claim 4, wherein said first pharmaceutical agent has an elution profile that is slower than the elution profile of the second pharmaceutical agent.

12. The method of claim 11, wherein the second pharmaceutical agent achieves 100% elution in about 5 days to about 20 days and the first pharmaceutical agent achieves 100% elution in about 120 days to about 180 days.

13. The method of claim 4, wherein said first pharmaceutical agent is an anti-thrombogenic agent and said second pharmaceutical agent is an anti-restenotic agent.

14. The method of claim 4, wherein said first pharmaceutical agent is heparin and said second pharmaceutical agent is taxol or a macrolide immunosuppressive drug.

15. The method of claim 2, wherein said bioabsorbably polymer is selected from PGA poly(glycolide), LPLA poly(l-lactide), DLPLA poly(dl-lactide), PCL poly(e-caprolactone)PDO, poly(dioxolane) PGA-TMC, 85/15 DLPLG p(dl-lacide-co-glycolide), 75/25 DLPLG, 65/35 DLPLG, 50/50 DLPLG, TMC poly(trimetylcarbonate), p(CPP:SA) poly(1,3-bis-p-(carboxyphenoxy)propane-co-sebacic acid).

16. The method of claim 1, wherein at least one of said pharmaceutical agents comprises a macrolide immunosuppressive drug.

17. The method of claim 16, wherein said macrolide immunosuppressive drug is at least 50% crystalline.

18. The method of claim 1, wherein said depositing at least one polymer layer comprises depositing polymer particles on said substrate by an RESS process.

19. The method of claim 1, wherein the at least one polymer layer is deposited in dry powder form.

20. The method of claim 1, wherein the at least one pharmaceutical layer is deposited in dry powder form.

* * * * *